US008517967B2

(12) United States Patent
Rosiello et al.

(10) Patent No.: US 8,517,967 B2
(45) Date of Patent: *Aug. 27, 2013

(54) METHODS OF USING AN APPARATUS FOR PROLONGING SURVIVAL OF PLATELETS USING CMP-SIALIC ACID, UDP-GALACTOSE OR BOTH

(75) Inventors: Keith Rosiello, Shrewsbury, MA (US); Henrik Clausen, Holte (DK)

(73) Assignee: Velico Medical, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/291,402

(22) Filed: Nov. 8, 2011

(65) Prior Publication Data
US 2012/0107791 A1    May 3, 2012

Related U.S. Application Data

(63) Continuation of application No. 11/574,857, filed as application No. PCT/US2005/031921 on Sep. 7, 2005, now Pat. No. 8,052,667.

(60) Provisional application No. 60/678,724, filed on May 6, 2005, provisional application No. 60/619,176, filed on Oct. 15, 2004, provisional application No. 60/607,600, filed on Sep. 7, 2004.

(51) Int. Cl.
*A61M 37/00* (2006.01)
*A61M 1/02* (2006.01)
*A61M 1/36* (2006.01)
*A61P 7/02* (2006.01)

(52) U.S. Cl.
USPC ....... 604/5.01; 604/6.01; 604/6.03; 604/6.07; 604/6.13; 604/6.15; 436/18; 424/93.72

(58) Field of Classification Search
USPC .............. 604/4.01, 5.01, 6.01, 6.03, 6.07, 604/6.13, 6.15, 403, 406, 408, 410, 416; 435/325, 366, 372, 374, 375
See application file for complete search history.

(56) References Cited

U.S. PATENT DOCUMENTS

| 4,344,936 | A | | 8/1982 | Soslau |
| 4,407,660 | A | * | 10/1983 | Nevens et al. ............ 604/6.04 |
| 4,432,750 | A | | 2/1984 | Estep et al. |
| 4,467,588 | A | | 8/1984 | Carveth et al. |

(Continued)

FOREIGN PATENT DOCUMENTS

| JP | H09-67270 | 8/1995 |
| WO | WO 98/41087 | 9/1998 |

(Continued)

OTHER PUBLICATIONS

Sialic Acid Related Products, Nacalai Tesque, Inc. Accessed Apr. 19, 2013. http://www.nacalai.co.jp/global/download/pdf/SialicAcids.pdf.*

(Continued)

*Primary Examiner* — Adam Marcetich
(74) *Attorney, Agent, or Firm* — Antoinette G Giugliano, PC

(57) ABSTRACT

The present invention provides modified platelets having a reduced platelet clearance and methods for reducing platelet clearance. Also provided are compositions for the preservation of platelets. The invention also provides methods for making a pharmaceutical composition containing the modified platelets and for administering the pharmaceutical composition to a mammal to mediate hemostasis.

17 Claims, 71 Drawing Sheets

IRDP – Individual Random Donor Platelets
PRDP – Pooled Random Donor Platelets
SDP – Single Donor Platelets

(56) References Cited

U.S. PATENT DOCUMENTS

| | | | |
|---|---|---|---|
| 4,610,684 A | 9/1986 | Knox et al. | |
| 4,701,267 A | 10/1987 | Watanabe et al. | |
| 4,915,848 A | 4/1990 | Carmen et al. | |
| 4,994,039 A | 2/1991 | Mattson | |
| 5,344,561 A | 9/1994 | Pall et al. | |
| 5,676,941 A | 10/1997 | Souza | |
| 5,876,676 A | 3/1999 | Stossel et al. | |
| 5,882,901 A * | 3/1999 | Venot et al. | 435/73 |
| 5,910,252 A | 6/1999 | Truitt et al. | |
| 5,919,614 A | 7/1999 | Livesey et al. | |
| 6,743,575 B2 | 6/2004 | Wiggins et al. | |
| 7,018,985 B1 | 3/2006 | Boyer et al. | |
| 7,037,428 B1 | 5/2006 | Robinson et al. | |
| 7,241,282 B2 | 7/2007 | Stossel et al. | |
| 7,645,609 B2 | 1/2010 | Follstad | |
| 7,858,295 B2 | 12/2010 | Stossel et al. | |
| 8,052,667 B2 * | 11/2011 | Rosiello et al. | 604/410 |
| 8,221,745 B2 * | 7/2012 | Rosiello et al. | 424/93.72 |
| 2002/0009705 A1 | 1/2002 | Lucas et al. | |
| 2002/0182581 A1 | 12/2002 | Cook et al. | |
| 2002/0193350 A1 | 12/2002 | Ellington et al. | |
| 2003/0104349 A1 | 6/2003 | Bischof et al. | |
| 2003/0176352 A1 | 9/2003 | Min et al. | |
| 2003/0224486 A1 * | 12/2003 | Carman et al. | 435/69.5 |
| 2004/0137557 A1 | 7/2004 | DeFrees et al. | |
| 2004/0185036 A1 * | 9/2004 | Stossel et al. | 424/94.61 |
| 2004/0236263 A1 * | 11/2004 | Van Waeg et al. | 604/5.01 |
| 2007/0087025 A1 * | 4/2007 | Fitzhugh et al. | 424/423 |
| 2007/0129282 A1 * | 6/2007 | Ahlem et al. | 514/2 |
| 2008/0199845 A1 | 8/2008 | Rosiello et al. | |
| 2009/0074737 A1 | 3/2009 | Rosiello et al. | |
| 2010/0160212 A1 | 6/2010 | Sheffer et al. | |
| 2011/0189151 A1 | 8/2011 | Stossel et al. | |

FOREIGN PATENT DOCUMENTS

| | | |
|---|---|---|
| WO | WO 02/16381 | 2/2002 |
| WO | WO 03/016469 | 2/2003 |
| WO | WO 03/090695 | 11/2003 |
| WO | WO 2004/043381 | 5/2004 |
| WO | WO 2006/044790 | 4/2006 |

OTHER PUBLICATIONS

Hartwig, et al., "Thrombin receptor ligation and activated Rac uncap actin filament barbed ends through phosphoinositide synthesis in permeabilized human platelets," *Cell*, 82:643-653, (1995).

Hartwig & DeSisto, "The cytoskeleton of the resting human blood platelet: Structure of the membrane skeleton and its attachment to actin filaments," *J. Cell Biol.*, 112:407-425, (1991).

Hartwig, et al., "D3 phosphoinositides and outside-in integrin signaling by GPIIb/IIIa mediate platelet actin assembly and filopodial extension induced by phorbol 12-myristate 13-acetate," *J. Biol. Chem.*, 271:32986-32993, (1996).

Kovacsovics & Hartwig, "Thrombin-induced GPIb-IX centralization on the platelet surface requires actin assembly and myosin H activation," *Blood*, 87:618-629, (1996).

Hoffmeister, et al., "The clearance mechanism of chilled blood platelets," *Cell*, 112:87-97, (2003).

Hoffmeister, et al., "Glycosylation Restores Survival of Chilled Blood Platelets," *Science*, 301:1531-1534, (2003).

Hoffmeister, et al., "Mechanisms of Cold-induced Platelet Actin Assembly," *J. Biol. Chem.*, 276:24751-24759, (2001).

Janmey & Stossel, "Gelsolin-polyphosphoinositide interaction. Full expression of gelsolin-inhibiting function by polyphosphoinositides in vesicular form and inactivation by dilution, aggregation, or masking of the inositol head group," *J. Biol. Chem.*, 254:4825-4831, (1989).

Liu, et al., "Combined biosynthetic pathway for de novo production of UDP-galactose: catalysis with multiple enzymes immobilized on agarose beads," *Chem. Biochem*, 3:348-355, (2002).

Stossel, et al., "Filamins as integrators of cell mechanics and signaling," *Nat. Rev. Mol. Cell. Biol.*, 2:138-145, (2001).

Arthur, et al., "Metabolites of Lactose Synthesis in Milk from Women During Established Lactation," *J. Pediatr. Gastroent. Nutr.*, 13:260-266, (1991).

Arthur, et al., "Metabolites of Lactose Synthesis in Milk from Diabetic and Nondiabetic Women During Lactogensis II," *J. Pediatr. Gastroent. Nutr.*, 19:100-108, (1994).

Raju, Shantha T., et al., "Glycoengineering of Therapeutic Glycoproteins: In Vitro Galactosylation and Sialylation of Glycoproteins with Terminal N-Acetylglucosamine and Galactose Residues," *Biochemistry*, 40:8868-8876, (2001).

Schlichter & Harker, "Preparation and storage of platelet concentrates II. Storage variables influencing platelet viability and function," *Brit. J. Haemat.*, 34:403-419, (1976).

Cui, Yun, et al.: "Study on the effect of UDP-Gal on platelets stored at low temperature by 51Cr tracing" XP002471055 retrieved from STN Database accession No. 2006: 171349.

Mester, L., et al.: "Role of sialic acid in the mechanism of platelet aggregation." XP002471056 retrieved from STN Database accession No. 1973: 544679.

Online Encyclopedia Article "Blood Bank" accessed Jan. 31, 2011, http://en.wikipedia.org/wiki/Blood_bank.

Hoffmeister, Karin M., et al., "Galactosylation Enables Prolonged Survival of Chilled Platelets in Mice," Nov. 16, 2003, Database accession No. PREV200400172516.

Berry, et al., "Endogenous synthesis of galactose in normal men and patients with hereditary galactosaemia," *Lancet*, 346:1073-1074, (1995).

Heilmann, et al., "Fluorescein derivatization of fibrinogen for flow cytometric analysis of fibrinogen binding to platelets," *Cytometry*, 17:287-293, (1994).

AAS & Gardener, "Survival of Blood Platelets with Chromium 51," *J Clin. Invest.*, 37:1257-1268, (1958).

Andre, et al., "CD40L stabilizes arterial thrombi by a beta3 integrin—dependent mechanism," *Nat Med*, 8:247-252, (2002).

Baker, et al., "A Simple, Fluorescent Method to Internally Label Platelets Suitable for Physiological Measurements," *Am. J. Hem*, 56:17-25, (1997).

Becker, et al., "Studies of Platelet Concentrates Stored at 22C and 4C," *Transfusion*, 13:61-68, (1973).

Berger, et al., "P-Selectin and platelet clearance," *Blood*, 92:4446-4452, (1998).

Bergmeier, et al., "Rhodocytin (aggretin) activates platelets lacking alpha2 beta1 integrin, glycoprotein VI, and the ligand-binding domain of glycoprotein Ibalpha," *J. Biol. Chem.*, 276:25121-25126, (2001).

Bergmeier, et al., "Structural and functional characterization of the mouse von Willebrand factor receptor GPib-IX with novel monoclonal antibodies," *Blood*, 95: 886-983, (2000).

Berman, et al., "A platelet alpha granule membrane protein that is associated with the plasma membrane after activation. Characterization and subcellular localization of platelet activation-dependent granule-external membrane protein," *J Clin Invest.*, 78:130-137, (1986).

Brown, et al., "Constitutive death of platelets leading to scavenger receptor-mediated phagocytosis. A caspase independent program," *J. Biol. Chem.*, 275:5987-5995, (2000).

Chernoff & Snyder, "The cellular and molecular basis of the platelet storage lesion: a symposium summery," *Transfusion*, 32:386-390, (1992).

Corbi, et al., "The human leukocyte adhesion glycoprotein Mac-1 (complement receptor type 3 CD11b) alpha subunit. Cloning, primary structure, and relation to the integrins, von Willebrand factor and factor B," *J. Biol. Chem.*, 263:12403-12411, (1988).

Coxon, et al., "A novel role for the [beta]2 integrin CDI Ib/CD18 in neutrophil apoptosis: a homeostatic mechanism in inflammation," *Immunity*, 5:653-666, (1996).

Denis, et al., "A mouse model of severe von Willebrand disease: defects in hemostasis and thrombosis," *Proc. Natl. Acad. Sci. USA*, 95:9524-9529, (1998).

Dumont, et al., "Platelet surface P-selectin measurements in platelet preparations: an international collaborative study. Biomedical Excellence for Safer Transfusion (BEST) Working Party of the International Society of Blood Transfusion (ISBT)," *Transfus. Med. Rev.*, 13:31-42, (1999).
Ellies, et al., "Sialyltransferase ST3GaI-IV operates as a dominant modifier of hemostasis by concealing asialoglycoprotein receptor ligands," *PNAS*, 99:10042-10047, (2002).
Endo, et al., "Large-scale production of CMP-NeuAc and sialylated oligosaccharides through bacterial coupling," *Appl. Microbiol. Biotechnol.*, 53:257-261, (2000).
Engelfriet, et al., "Bacterial contamination of blood components," *Vox Sang*, 78:59-67, (2000).
Faraday & Rosenfeld, "In vitro hypothermia enhances platelet GPIIb-IIIa activation and P-selectin expression," *Anesthesiology*, 88:1579-1585, (1998).
Greenberg & Jamieson, "The effects of various lectins of platelet aggregation and release," *Biochem. Biophys. Acta*, 345:231-242, (1974).
Jacobs, et al., "Don't bug me: the problem of bacterial contamination of blood components—challenges and solutions," *Transfusion*, 41:1331-1334, (2001).
Hoyer, et al., "Influence of dose on regeneration of murine hematopoietic stem cells after total body irradiation and 5-fluorouracil," *Oncology*, 49:166-174, (1992).
Jaremo, et al., "Correlation of light transmission changes to changes of platelet glycoprotein Ib during storage of platelet concentrates," *Thromb. Res.*, 69:467-477, (1993).
Josefsson, et al., "The macrophage alphaMbeta2 integrin alphaM lectin domain mediates the phagocytosis of chilled platelets," *J. Biol. Chem.*, 280:18025-18032, (2005).
Endo, et al., "Large-scale production of N-acetyllactosamine through bacterial coupling," *Carbohydr. Res.*, 316:179-183, (1999).
Korrel, et al., "Identification of a tetrasialylated monofucosylated tetraantennary N-linked carbohydrate chain in human platelet glycocalicin," *FEBS Lett.*, 228:321-326, (1988).
Lazarowski, et al., "Release of cellular UDP-glucose as a potential extracellular signaling molecule," *Mol. Pharmacol.*, 63:1190-1197, (2003).
Lok, et al., "Cloning and expression of murine thrombopoietin cDNA and stimulation of platelet production in vivo," *Nature*, 369:565-568, (1994).
Lopez, et al., "Cloning of the alpha chain of human platelet glycoprotein IB: a transmembrane protein with homology to leucine-rich alpha 2-glycoprotein," *Proc. Natl. Acad. Sci., USA*, 84:5615-5619, (1987).
MacPhee, et al., "Evidence for Kupffer cell migration along liver sinusoids, from high-resolution in vivo microscopy," *Am. J. Physiol.*, 263:17-23, (1992).
Michelson, et al., "In vivo tracking of platelets: circulation degranulated platelets rapidly lose surface P-selectin but continue to circulate and function," *Proc. Natl. Acad. Sci., USA*, 93:11877-11882, (1996).
Michelson, et al., "Platelet storage results in a redistribution of glycoprotein Ib molecules. Evidence for a large intraplatelet pool of glycoprotein Ib," *J. Clin. Invest.*, 81:1734-1740, (1988).
Mizoguchi, et al., "Galactose metabolites in blood from neonates with and without hypergalactosaemia detected by mass screening," *Eur. J. Pediatr.*, 159:851-853, (2000).
Morton, et al., "Integrin-alpha2beta1—independent activation of platelets by simple collagen-like peptides: collagen tertiary (triple-helical) and quaternary (polymeric) structures are sufficient alone for alpha2beta1—independent platelet reactivity," *Biochem J.*, 306:337-344, (1995).
Moshfegh, et al., "Fine structural and functional consequences of deglycosylation of the platelet adhesion receptor GPIb-IX (CD 42b)," *Biochem. Biophys. Res. Communic.*, 249:903-909, (1998).
Murphy, et al., "Hereditary thrombocytopenia with an intrinsic platelet defect," *N. Engl. J. Med.*, 281:857-862, (1969).
Ni, et al., "Increased thrombogensis and embolus formation in mice lacking glycoprotein V," *Blood*, 98:368-373, (2001).
Petty, et al., "Receptor-receptor interactions of complement receptor type 3 in neutrophil membranes," *J. Leukoc. Biol.*, 54:492-494, (1993).

Rendu & Lebret, "Interaction of wheat germ agglutinin with human platelets: a model for studying platelet response," *Thromb. Res.*, 36:447-456, (1984).
Ribeiro, et al., "Alterations of the levels of glycoproteins Ib-IX and IIb-IIIa in platelets stored at 22 degrees C," *Thromb. Res.*, 66:619-627, (1992).
Ross, "Regulation of the adhesion versus cytotoxic functions of the Mac-1/CR3/alphaMbeta2-integrin glycoprotein," *Critical Reviews in Immunology*, 20:197-222, (2000).
Sehgal, et al., "Lectin-like inhibition of immune complex receptor-mediated stimulation of neutrophils. Effects on cytosolic calcium release and superoxide production," *J. Immunol.*, 150:4571-4580, (1993).
Simon, et al., "Platelet glycoprotein ib[alpha] is a counterreceptor for the leukocyte integrin Mac-1 (CDI Ib/CD18),"*J. Exp. Med.*, 192:193-204, (2000).
Simon, et al., "Mac-1 (CDI Ib/CD18) and the urokinase receptor (CD87) from a functional unit on monocytic cells," *Blood*, 88:3185-3194, (1996).
Tablin, et al., "Membrane phase transition of intact human platelets: correlation with cold-induced activation," *J. Cell. Phys.*, 168:305-313, (1996).
Takeda, et al., "Morphologic alternation of hepatocytes and sinusoidal endothelial cells in rat fatty liver during cold preservation and the protective effect of hepatocyte growth factor," *Transplantation*, 67:820-828, (1999).
Thornton, et al., "Analysis of the sugar specificity and molecular location of the beta-glucan-binding lectin site of complement receptor type 3 (CD11b/CD18)," *J. Immunol.*, 156:1235-1246, (1996).
Titani, et al., "Amino acid sequence of the von Willebrand factor-binding domain of platelet membrane glycoprotein Ib," *Proc. Natl. Acad. Sci., USA*, 84:5610-5614, (1987).
Tsuji, et al., "The carbohydrate moiety of human platelet glycocalicin," *J. Biol. Chem.*, 258:6335-6339, (1983).
Valeri, et al., "Effect of thrombopoietin alone and a combination of cytochalasin B and ethylene glycol bis (beta-aminoethyl ether) N, N'-tetraacetic acid-AM on the survival and function of autologous baboon platelets stored at 4 degrees C for as long as 5 days," *Transfusion*, 44:865-870, (2004).
Von Adrian, "Immunology. T cell activation in six dimensions," *Science*, 296:1815-1817, (2002).
Von Adrian, "Intravital microscopy of the peripheral lymph node microcirculation in mice," *Microcirculation*, 3:287-300, (1996).
Ward, et al., "Mocargain, a novel cobra venom metalloproteinase, cleaves the platelet von Willebrandt factor receptor glycoprotein Ibalpha. Identification of the sulfated tyrosine/anionic sequence Tyr-276-Glu-282 of glycoprotein Ib [alpha] as a binding site for von Willebrandt factor and a-thrombin," *Biochemistry*, 35:4929-4938, (1996).
Ware, et al., "Generation and rescue of a murine model of platelet dysfunction: the Bernard-Soulier syndrome," *Proc. Natl. Acad. Sci., USA*, 97:2803-2808, (2000).
Wessels, et al., "Studies of group B streptococcal infection in mince deficient in complement component C3 or C4 demonstrate an essential role for complement in both innate and acquired immunity," *Proc. Natl. Acad. Sci., USA*, 92:11490-11494, (1995).
White & Krivit, "An ultrastructural basis for the shape changes induced in platelets by chilling," *Blood*, 30:625-635, (1967).
Winokur & Hartwig, "Mechanism of shape change in chilled human platelets," *Blood*, 55:1796-1804, (1995).
Xia, et al., "Generation of recombinant fragments of CD11b expressing the functional beta-glucan-binding lectin site of CR2(CD11b/CD18)," *J. Immunol.*, 162:7285-7293, (1999).
Yan, et al., "Critical role of Kupffer cell CR2(CDI Ib/CD18) in the clearance of IgM-opsonized erythrocytes or soluble P-glucan," *Immunopharamacology*, 46:39-54, (2000).

Yomtovian, et al., "A prospective microbiolgic surveillance program to detect and prevent the transfusion of bacterially contaminated platelets," *Transfusion*, 33:902-909, (1993).

Zucker & Borrelli, "Reversible alteration in platelet morphology produced by anticoagulants and by cold," *Blood*, 9:602-608, (1954).

Heidlas, et al., "Practical Enzyme-Based Syntheses of Uridine 5'-Diphosphogalactose and Uridine 5'-Diphospho-N-acetylgalactosamine on a Gram Scale," *J. Org. Chem.*, 57:152-157, (1992).

Szabados, et al., "Accelerated Uptake of 5-Hydroxytryptamine by Human Blood Platelets Enriched in a Sialic Acid," *Biochem. J.* 148:335-336, (1975).

* cited by examiner

STUDIES ON HUMAN PLATELET CONCENTRATES

✓ Platelets in platelet concentrates can be galactosylated.

✓ Galactosylation is stable during refrigeration storage and prevents phagocytosis by macrophages *in vitro*.

✓ Refrigeration preserves *in vitro* platelet functions during extended storage; galactosylation plus refigeration preserves some platelet functions better than refrigeration alone.

Fig. 34

METHODS OF USING AN APPARATUS FOR PROLONGING SURVIVAL OF PLATELETS USING CMP-SIALIC ACID, UDP-GALACTOSE OR BOTH

RELATED APPLICATIONS

This application is a continuation of U.S. patent application Ser. No. 11/574,857, filed Mar. 7, 2007 (371 date Dec. 31, 2007), which is the U.S. National stage of International Application No. PCT/US2005/031921, filed on Sep. 7, 2005, which claims the benefit of U.S. Provisional Application No. 60/678,724, filed May 6, 2005, U.S. Provisional Application No. 60/619,176, filed on Oct. 15, 2004, and U.S. Provisional Application No. 60/607,600, filed on Sep. 7, 2004. The entire teachings of the above applications are incorporated herein by reference.

FIELD OF THE INVENTION

The inventions relate to compositions and methods for reducing the clearance of platelets and prolonging the survival of platelets.

BACKGROUND OF THE INVENTION

Platelets are anucleate bone marrow-derived blood cells that protect injured mammals from blood loss by adhering to sites of vascular injury and by promoting the formation of plasma fibrin clots. Humans depleted of circulating platelets by bone marrow failure suffer from life threatening spontaneous bleeding, and less severe deficiencies of platelets contribute to bleeding complications following trauma or surgery.

A reduction in the number of circulating platelets to below ~70,000 per uL reportedly results in a prolongation of a standardized cutaneous bleeding time test, and the bleeding interval prolongs, extrapolating to near infinity as the platelet count falls to zero. Patients with platelet counts of less than 20,000 per uL are thought to be highly susceptible to spontaneous hemorrhage from mucosal surfaces, especially when the thrombocytopenia is caused by bone marrow failure and when the affected patients are ravaged with sepsis or other insults. The platelet deficiencies associated with bone marrow disorders such as a plastic anemia, acute and chronic leukemias, metastatic cancer but especially resulting from cancer treatment with ionizing radiation and chemotherapy represent a major public health problem. Thrombocytopenia associated with major surgery, injury and sepsis also eventuates in administration of significant numbers of platelet transfusions.

A major advance in medical care half a century ago was the development of platelet transfusions to correct such platelet deficiencies, and over 9 million platelet transfusions took place in the United States alone in 1999 (Jacobs et al., 2001). Platelets, however, unlike all other transplantable tissues, do not tolerate refrigeration, because they disappear rapidly from the circulation of recipients if subjected to even very short periods of chilling, and the cooling effect that shortens platelet survival is irreversible (Becker et al., 1973; Berger et al., 1998).

The resulting need to keep these cells at room temperature prior to transfusion has imposed a unique set of costly and complex logistical requirements for platelet storage. Because platelets are actively metabolic at room temperature, they require constant agitation in porous containers to allow for release of evolved $CO_2$ to prevent the toxic consequences of metabolic acidosis. Room temperature storage conditions result in macromolecular degradation and reduced hemostatic functions of platelets, a set of defects known as "the storage lesion" (Chernoff and Snyder, 1992). But the major problem with room-temperature storage, leading to its short (5-day) limitation, is the higher risk of bacterial infection. Bacterial contamination of blood components is currently the most frequent infectious complication of blood component use, exceeding by far that of viral agents (Engelfriet et al., 2000). In the USA, 3000-4500 cases yearly of bacterial sepsis occur because of bacterially contaminated blood components (Yomtovian et al., 1993).

The mechanism underlying the unique irreversible cold intolerance of platelets has been a mystery as has its physiological significance. Circulating platelets are smooth-surfaced discs that convert to complex shapes as they react to vascular injury. Over 40 years ago investigators noted that discoid platelets also change shape at refrigeration temperatures (Zucker and Borrelli, 1954). Subsequent evidence that a discoid shape was the best predictor of viability for platelets stored at room temperature (Schlichter and Harker, 1976) led to the conclusion that the cold-induced shape change per se was responsible for the rapid clearance of chilled platelets. Presumably irregularly-shaped platelets deformed by cooling became entrapped in the microcirculation.

Based on our studies linking signaling to the mechanisms leading to platelet shape changes induced by ligands (Hartwig et al., 1995), we predicted that chilling, by inhibiting calcium extrusion, could elevate calcium levels to a degree consistent with the activation of the protein gelsolin, which severs actin filaments and caps barbed ends of actin filaments. We also reasoned that a membrane lipid phase transition at low temperatures would cluster phosphoinositides. Phosphoinositide clustering uncaps actin filament barbed ends (Janmey and Stossel, 1989) to create nucleation sites for filament elongation. We produced experimental evidence for both mechanisms, documenting gelsolin activation, actin filament barbed end uncapping, and actin assembly in cooled platelets (Hoffmeister et al., 2001; Winokur and Hartwig, 1995). Others have reported spectroscopic changes in chilled platelets consistent with a membrane phase transition (Tablin et al., 1996). This information suggested a method for preserving the discoid shape of chilled platelets, using a cell-permeable calcium chelator to inhibit the calcium rise and cytochalasin B to prevent barbed end actin assembly. Although addition of these agents retained platelets in a discoid shape at 4° C. (Winokur and Hartwig, 1995), such platelets also clear rapidly from the circulation, as we report here. Therefore, the problem of the rapid clearance of chilled platelets remains, and methods of increasing circulation time as well as storage time for platelets are needed.

SUMMARY OF THE INVENTION

The present invention provides modified platelets having a reduced platelet clearance and methods for reducing platelet clearance. Also provided are compositions and methods for the preservation and storage of platelets, such as mammalian platelets, particularly human platelets. The invention also provides methods for making a pharmaceutical composition containing the modified platelets and for administering the pharmaceutical composition to a mammal to mediate hemostasis.

It has now been discovered that cooling of human platelets causes clustering of the von Willebrand factor (vWf) receptor complex α subunit (GP1bα) complexes on the platelet surface. The clustering of GP1bα complexes on the platelet surface elicits recognition by macrophage complement type three receptors (αMβ2, CR3) in vitro and in vivo. CR3 receptors recognize N-linked sugars with terminal βGlcNAc on the surface of platelets, which have formed GP1bα complexes, and phagocytose the platelets, clearing them from the circulation and resulting in a concomitant loss of hemostatic function.

Applicants have discovered that treatment of platelets with an effective amount of a glycan modifying agent such as N-acetylneuraminic acid (sialic acid), or certain nucleotide-sugar molecules, such as CMP-sialic acid or UDP-galactose leads to sialylation or glycation of the exposed βGlcNAc residues on GP1bα. Effective amounts of a glycan modifying agent range from about 1 micromolar to about 10 millimolar, about 1 micromolar to about 1 millimolar, and most preferably about 200 micromolar to about 600 micromolar of the glycan modifying agent. This has the functional effect of reducing platelet clearance, blocking platelet phagocytosis, increasing platelet circulation time, and increasing both platelet storage time and tolerance for temperature changes. Additionally, platelets removed from a mammal may be stored cold for extended periods, i.e., at 4 degrees C. for 24 hours, 2 days, 3 days, 5 days, 7 days, 12 days or 20 days or more, without significant loss of hemostatic function following transplantation. Cold storage provides an advantage that it inhibits the growth of contaminating microorganisms in the platelet preparation, important as platelets are typically given to cancer patients and other immunocompromised patients.

According to one aspect of the invention, methods for increasing the circulation time of a population of platelets is provided. The method comprises contacting an isolated population of platelets with at least one glycan modifying agent in an amount effective to reduce the clearance of the population of platelets. In some embodiments, the glycan modifying agent is selected from the group consisting UDP-galactose and UDP-galactose precursors. In some preferred embodiments, the glycan modifying agent is UDP-galactose.

In some embodiments, the method further comprises adding an enzyme that catalyzes the modification of a glycan moiety on the platelet. One example of an enzyme that catalyzes the modification of the glycan moiety is galactosyl transferase, particularly a beta-1-4-galactosyl transferase. Another example of an enzyme that catalyzes the modification of a glycan moiety is a sialyl transferase, which adds sialic acid to the terminal galactose on the glycan moiety of the platelet.

In one of the preferred embodiments, the glycan modifying agent is UDP-galactose and the enzyme that catalyzes the modification of the glycan moiety is galactosyl transferase. In certain aspects, the glycan modifying agent further includes a second chemical moiety, which is added to the glycan on the platelet in a directed manner. An example of this second chemical moiety is polyethylene glycol (PEG), which when coupled to the glycan modifying agent such as UDP-galactose as UDP-galactose-PEG, in the presence of an enzyme such as galactosyl transferase, will catalyze the addition of PEG to the platelet at the terminus of the glycan moiety. Thus in certain embodiments, the invention provides for compositions and methods for the targeted addition of compounds to the sugars and proteins of cells.

In some embodiments, the method for increasing the circulation time of a population of platelets further comprises chilling the population of platelets prior to, concurrently with, or after contacting the platelets with the at least one glycan modifying agent.

In some embodiments, the population of platelets retains substantially normal hemostatic activity.

In some embodiments, the step of contacting the population of platelets with at least one glycan modifying agent is performed in a platelet bag.

In some embodiments, the circulation time is increased by at least about 10%, 15%, 20%, 25%, 30%, 40%, 50%, 60%, 75%, 100%, 150%, 200%, 500% or more.

According to another aspect of the invention, a method for increasing the storage time of platelets is provided. The method comprises contacting an isolated population of platelets with an amount of at least one glycan modifying agent effective to reduce the clearance of the population of platelets, and storing the population of platelets. Effective amounts of a glycan modifying agent range from about 1 micromolar to about 1200 micromolar, and most preferably about 200 micromolar to about 600 micromolar of the glycan modifying agent. In certain aspects the platelet preparation is stored at cold temperatures, i.e., frozen or refrigerated.

In some embodiments, the glycan modifying agent is selected from the group consisting of: a sugar, a monosaccharide sugar, a nucleotide sugar, sialic acid, sialic acid precursors, CMP-sialic acid, UDP-galactose, and UDP-galactose precursors. In some embodiments, the glycan modifying agent is preferably UDP-galactose.

In some embodiments, the method further comprises adding an effective amount of an enzyme that catalyzes the addition of the glycan modifying agent to a glycan on the surface of the platelets. In one of the preferred embodiments, the glycan modifying agent is UDP-galactose and the enzyme that catalyzes the addition of the glycan modifying agent to a glycan on the surface of the platelets is galactosyl transferase, preferably a beta-1-4-galactosyl transferase. In another preferred embodiment, the glycan modifying agent is CMP-sialic acid and the enzyme that catalyzes the addition of the glycan modifying agent to a glycan on the surface of the platelets is sialyl transferase.

In some embodiments, the method further comprises chilling the population of platelets prior to, concurrently with, or after contacting the platelets with the at least one glycan modifying agent.

In some embodiments, the population of platelets retains substantially normal hemostatic activity when transplanted in a mammal. Prior to transplantation the glycan modifying agent is preferably diluted or reduced to concentrations of about 50 micromolar or less.

In certain embodiments, the step of contacting the population of platelets with at least one glycan modifying agent is performed during collection of whole blood or collection of the platelets. In certain embodiments, the glycan modifying agent is introduced into a platelet bag prior to, concurrently with, or after collection of the platelets.

The platelets are capable of being stored at reduced temperatures, for example, frozen, or chilled, and can be stored for extended periods of time, such as at least about 3 days, at least about 5 days, at least about 7 days, at least about 10 days, at least about 14 days, at least about 21 days, or at least about 28 days.

According to another aspect of the invention, a modified platelet is provided. The modified platelet comprises a plurality of modified glycan molecules on the surface of the platelet. The modified glycan molecules include sialic acid additions to the terminal sugar residues, or galactosylation of the terminal sugar residues.

In some embodiments, the modified glycan molecules are moieties of GP1bα molecules. The modified glycan molecules comprise sialic acid or at least one added sugar molecule. The added sugar may be a natural sugar or may be a non-natural sugar. Examples of added sugars include but are not limited to: nucleotide sugars such as UDP-galactose and UDP-galactose precursors. In one of the preferred embodiments, the added nucleotide sugar is CMP-sialic acid or UDP-galactose.

In another aspect, the invention provides a platelet composition comprising a plurality of modified platelets. In some embodiments, the platelet composition further comprises a storage medium. In some embodiments, the platelet composition further comprises a pharmaceutically acceptable carrier.

According to yet another aspect of the invention, a method for making a pharmaceutical composition for administration to a mammal is provided. The method comprises the steps of:

(a) contacting a population of platelets contained in a pharmaceutically-acceptable carrier with at least one glycan modifying agent to form a treated platelet preparation, (b) storing the treated platelet preparation, and (c) warming the treated platelet preparation.

In some embodiments, the step of warming the treated platelet preparation is performed by warming the platelets to 37° C.

In some embodiments, the step of contacting a population of platelets contained in a pharmaceutically-acceptable carrier with at least one glycan modifying agent comprises contacting the platelets with at least one glycan modifying agent, alone or in the presence of an enzyme that catalyzes the modification of a glycan moiety. The glycan modifying agent is preferably added at concentrations of about 1 micromolar to about 1200 micromolar, and most preferably about 200 micromolar to about 600 micromolar. In some embodiments, the method further comprises reducing the concentration of, or removing or neutralizing the glycan modifying agent or the enzyme in the platelet preparation. Methods of reducing the concentration of, removing or neutralizing the glycan modifying agent or enzyme include, for example, washing the platelet preparation or dilution of the platelet preparation. The glycan modifying agent is preferably diluted to about 50 micromolar or less prior to transplantation of the platelets into a human subject.

Examples of glycan modifying agents are listed above. In one of the preferred embodiments, the glycan modifying agent is CMP-sialic acid or UDP-galactose. In some embodiments, the method further comprises adding an exogenous enzyme that catalyzes the addition of the glycan modifying agent to a glycan moiety, such as a beta-1-4 galactosyl transferase.

In one of the preferred embodiments, the glycan modifying agent is UDP-galactose and the enzyme is galactosyl transferase.

In some embodiments, the population of platelets demonstrate substantially normal hemostatic activity, preferably after transplantation into a mammal.

In certain embodiments, the step of contacting the population of platelets with at least one glycan modifying agent is performed during the collection process on whole blood or fractionated blood, such as on platelets in a platelet bag.

In some embodiments, the platelet preparation is stored at a temperature of less than about 15° C., preferably less than 10° C., and more preferably less than 5° C. In some other embodiments, the platelet preparation is stored at room temperature. In other embodiments, the platelets are frozen, e.g., 0° C., −20° C., or −80° C. or cooler.

According to yet another aspect of the invention, a method for mediating hemostasis in a mammal is provided. The method comprises administering a plurality of modified platelets or a modified platelet composition to the mammal. The platelets are modified with the glycan modifying agent prior to administration, such as during collection, prior to storing, after storage and during warming, or immediately prior to transplantation.

According to still yet another aspect of the invention, a storage composition for preserving platelets is provided. The composition comprises at least one glycan modifying agent, added to the platelets in an amount sufficient to modify platelets glycans, thereby increase the storage time and/or the circulation time of platelets added to the storage composition by reducing platelet clearance.

In some embodiments the composition further comprises an enzyme that catalyzes the modification of a glycan moiety. The enzyme may be exogenously added. A beta-1-4 galactosyl transferase or a sialyl transferase, or both, exemplify preferred enzymes for catalyzing the modification of the glycan moieties on the platelets.

According to another aspect of the invention, a container for collecting (and optionally processing) platelets is provided. The container comprises at least one glycan modifying agent in an amount sufficient to modify glycans of platelets contained therein. The container is preferably a platelet bag, or other blood collection device.

In some embodiments, the container further comprises an enzyme that catalyzes the modification of a glycan moiety with the glycan modifying agent, such as a beta-1-4 galactosyl transferase or a sialyl transferase.

In some embodiments the container further comprises a plurality of platelets or plasma comprising a plurality of platelets.

In some embodiments, the glycan modifying agent is present at a concentration higher than it is found in naturally occurring platelets or in serum. In certain aspects these concentrations are 1 micromolar to 1200 micromolar, and most preferably about 200 micromolar to about 600 micromolar. In other embodiments, the beta-1-4 galactosyl transferase or a sialyl transferase is at a concentration higher than it is found in naturally occurring platelets or in serum, such as concentrations that would be observed if the enzyme were added exogenously to the platelets.

According to still yet another aspect of the invention, a device for collecting and processing platelets is provided. The device comprises: a container for collecting platelets; at least one satellite container in fluid communication with said container; and at least one glycan modifying agent in the satellite container. The container optionally includes an enzyme such as a beta-1-4 galactosyl transferase or a sialyl transferase.

In some embodiments, the glycan modifying agent in the satellite container is present in sufficient amounts to preserve the platelets in the container, for example from concentrations of about 1 micromolar to about 1200 micromolar.

In some embodiments, the glycan modifying agent in the satellite container is prevented from flowing into the container by a breakable seal.

In other aspects, the invention includes a kit having a sterile container capable of receiving and containing a population of platelets, the container substantially closed to the environment, and a sterile quantity of a glycan modifying agent sufficient to modify a volume of platelets collected and stored in the container, the kit further includes suitable packaging materials and instructions for use. Glycan modifying agents in the kit include CMP-sialic acid, UDP-galactose, or sialic acid. The container is suitable for cold-storage of platelets.

The invention also includes, in certain aspects, a method of modifying a glycoprotein comprising, obtaining a plurality of platelets having GP1bα molecules, and contacting the platelets with a glycan modifying agent, wherein the glycan modifying agent galactosylates or sialylates the terminus of a GP1bα molecule on the platelets.

The invention further includes a method of modifying a blood constituent comprising, obtaining a sample of blood having platelets, and contacting at least the platelets with a glycan modifying agent, wherein the glycan modifying agent galactosylates or sialylates the terminus of a GP1bα molecule on the platelets.

In other aspects, the invention includes a method of reducing pathogen growth in a blood sample comprising, obtaining a sample of blood having platelets, contacting at least the platelets with a glycan modifying agent, wherein the glycan modifying agent galactosylates or sialylates the terminus of a GP1bα molecule on the platelets, and storing the blood sample having modified platelets at a temperature of about 2 degrees C. to about 18 degrees C. for at least three days, thereby reducing pathogen growth in the blood sample.

In another aspect, the invention provides an apparatus for processing a sample of blood cells, including a sterile first container having one or more ports and containing a preparation of blood cells, a second sterile container having one or more ports and containing a blood cell modifying agent, (also referred to as a platelet solution or a glycan modifying agent) the first container adapted to the second container through a sterile conduit reversibly attachable to the first container port and the second container port, the conduit further comprising a valve, wherein the blood cell modifying agent is introduced into the first container and the preparation of blood cells therein is rendered cold storage competent after the blood cells are contacted with the blood cell modifying agent. In one embodiment, the invention includes a sterile third container having one or more ports adapted to the first container through a second sterile conduit reversibly attachable to the first container port and the third container port, the conduit further comprising a valve. In another embodiment, the invention includes a leukocyte filter. In various embodiments, some shown in the figures, the first container, second container or the third container are blood bags or a syringe. In other embodiments, the blood cell modifying agent is a nucleoside sugar such as UDP galactose, or cytidine 5'monophospho-N-acetylneuraminic acid. The blood cells suitable for modification in the bioprocess include a population of platelets obtained from individual random donor blood, pooled random donor blood, or single donor blood. In various other embodiments, the conduit is adapted to an in-line filter having a median pore diameter small enough to substantially prevent the flow of bacteria through the in-line filter. Preferred median pore diameters for the in-line filter are less than about 1 micron, more preferably less than about 0.50 microns and most preferably about 0.22 microns. In yet another embodiment, the second container port has a frangible barrier. In even another embodiment, the first conduit or the second conduit reversibly attaches to the first container port, the second container port or the third container port through a sterile dock.

In another aspect, the invention provides an apparatus for processing a sample of blood cells, including a sterile first container having one or more ports, and an array having a conduit and a plurality of sterile docks, wherein each of the sterile docks are reversible adaptable to blood storage containers, the blood storage containers having a sample of blood cells and further comprising at least one port for connecting to the sterile docks of the array, wherein the blood cells are introduced into the sterile first container through the conduit and are rendered cold storage competent after the blood cells are contacted with a blood cell modifying agent introduced into the first container. In some embodiments, the blood cell modifying agent is a sterile nucleoside sugar such as UDP galactose or a sterile preparation of cytidine 5'monophospho-N-acetylneuraminic acid. In various other embodiments, the invention provides an in-line filter having a median pore diameter small enough to substantially prevent the flow of bacteria through the in-line filter. Preferred median pore diameters for the in-line filter are less than about 1 micron, more preferably less than about 0.50 microns and most preferably about 0.22 microns. In one embodiment, the blood cells further comprise a population of platelets obtained from individual random donor blood, pooled random donor blood, or single donor blood. In another embodiment, the array further comprises a leukocyte filter proximal to the first container. In even another embodiment, the blood cell modifying agent is contained in the first to container. In another embodiment, the invention includes a second container having one or more ports and containing a blood cell modifying agent, the first container adapted to the second container through a sterile conduit reversibly attachable to the first container port and the second container port. In still yet another embodiment, the second container is a syringe. In one embodiment, the conduit is adapted to an in-line filter having a median pore diameter small enough to substantially prevent the flow of bacteria through the in-line filter. In another embodiment median pore diameters for the in-line filter are less than about 1 micron, more preferably less than about 0.50 microns and most preferably about 0.22 microns. In another embodiment, the second container port has a frangible barrier.

In another aspect, the invention provides an apparatus for processing a sample of blood cells, including a sterile first container having one or more ports the first container further comprising a subcontainer disposed therein, the subcontainer having a port and a frangible barrier and containing a blood cell modifying agent, and an array comprising a conduit and a plurality of sterile docks, wherein each of the sterile docks are reversible adaptable to blood storage containers, the blood storage containers having a sample of blood cells and further comprising at least one port for connecting to the sterile docks of the array, wherein the blood cells are introduced into the sterile first container through the conduit and are rendered cold storage competent after the blood cells are contacted with a blood cell modifying agent introduced into the first container. In one embodiment, the blood cell modifying agent is a sterile nucleoside sugar such as UDP galactose or a sterile preparation of cytidine 5'monophospho-N-acetylneuraminic acid. In another embodiment median pore diameters for the in-line filter are less than about 1 micron, more preferably less than about 0.50 microns and most preferably about 0.22 microns. In another embodiment, the second container port has a frangible barrier. In another embodiment, the blood cells further comprise a population of individual random donor blood, pooled random donor blood, or single donor blood. In another embodiment, the array further comprises a leukocyte filter proximal to the first container.

In one aspect, the invention provides a method for treating a blood cell, including obtaining an apparatus as described, obtaining a sample of blood cells including a subpopulation of platelets, and exposing the blood cells to the blood cell modifying agent in the apparatus thereby rendering the subpopulation of platelets cold-storage competent. In one embodiment, the method includes separating the leukocytes from the blood cells prior to exposing the blood cells to the blood cell modifying agent. In one embodiment, the blood cell modifying agent is a sterile nucleoside sugar such as UDP galactose or a sterile preparation of cytidine 5'monophospho-N-acetylneuraminic acid. In another embodiment median pore diameters for the in-line filter are less than about 1 micron, more preferably less than about 0.50 microns and most preferably about 0.22 microns. In another embodiment, the second container port has a frangible barrier. In another embodiment, the blood cells further comprise a population of individual random donor blood, pooled random donor blood, or single donor blood. In another embodiment, the method provides that the blood cells are contacted with the blood cell modifying agent before infusion of the treated blood cells into a patient. In another embodiment, the method provides that the blood cells are contacted with the blood cell modifying agent before cold storage of the blood cells. In another embodiment, the method provides that the blood cells are contacted with the blood cell modifying agent at the time of blood collection from a blood donor. In another embodiment, the method provides for separating the blood cells into subpopulations of platelets, plasma, red blood cells and white blood cells. In another embodiment, the blood cells are contacted with the blood cell modifying agent after the blood cells have been separated by apheresis.

In another aspect, the invention provides for a treated blood cell obtained through the methods described. The treated blood cells, following cold storage, are suitable for transfusion into a patient. These and other aspects of the invention, as well as various advantages and utilities, will be more apparent in reference to the following detailed description of the invention. Each of the limitations of the invention can encompass various embodiments of the invention. It is therefore, anticipated that each of the limitations involving any one element or combination of elements can be included in each aspect of the invention.

BRIEF DESCRIPTION OF THE DRAWINGS

FIG. 3 shows that chilled platelets adhere tightly to CR3-expressing mouse macrophages in vivo.

FIG. 4 shows that GP1bα mediates chilled platelet clearance, aggregates in the cold, but binds activated vWf normally on chilled platelets.

FIG. 5 shows GP1bα-CR3 interaction mediates phagocytosis of chilled human platelets in vitro.

FIG. 34 shows that human platelet concentrates can be galactosylated, which preserves platelet function.

DETAILED DESCRIPTION OF THE INVENTION

Figure 1A:
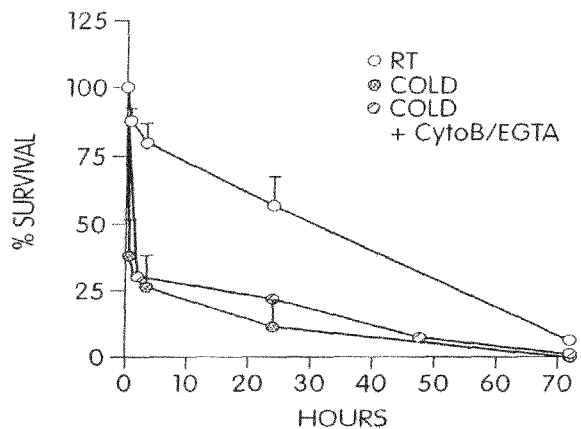
FIG. 1A shows circulation time in mice of room temperature platelets and of platelets chilled and rewarmed in the presence or absence of EGTA-AM and Cytochalasin B. The curves depict the survival of 5-chloromethylfluorescein diacetate (CMFDA) labeled, room temperature (RT) platelets, platelets chilled at ice-bath temperature (Cold) and rewarmed to room temperature before injection and chilled and rewarmed platelets treated with EGTA-AM and cytochalasin B (Cold+CytoB/EGTA) to preserve their discoid shape. Each curve represents the mean±SD of 6 mice. Identical clearance patterns were observed with $^{111}$Indium-labeled platelets.

The invention provides a population of modified platelets that have enhanced circulation properties and that retain substantially normal in vivo hemostatic activity. Hemostatic activity refers broadly to the ability of a population of platelets to mediate bleeding cessation. Various assays are available for determining platelet hemostatic activity (Bennett, J. S, and Shattil, S. J., 1990, "Platelet function," Hematology, Williams, W. J., et al., Eds. McGraw Hill, pp 1233-12250). However, demonstration of "hemostasis" or "hemostatic activity" ultimately requires a demonstration that platelets infused into a thrombocytopenic or thrombopathic (i.e., non-functional platelets) animal or human circulate and stop natural or experimentally-induced bleeding.

Short of such a demonstration, laboratories use in vitro tests as surrogates for determining hemostatic activity. These tests, which include assays of aggregation, secretion, platelet morphology and metabolic changes, measure a wide variety of platelet functional responses to activation. It is generally accepted in the art that the in vitro tests are reasonably indicative of hemostatic function in vivo.

Substantially normal hemostatic activity refers to an amount of hemostatic activity seen in the modified platelets, that is functionally equivalent to or substantially similar to the hemostatic activity of untreated platelets in vivo, in a healthy (non-thrombocytopenic or non-thrombopathic mammal) or functionally equivalent to or substantially similar to the hemostatic activity of a freshly isolated population of platelets in vitro.

The instant invention provides methods for reduced temperature storage of platelets which increases the storage time of the platelets, as well as methods for reducing clearance of or increasing circulation time of a population of platelets in a mammal. Also provided are platelet compositions methods and compositions for the preservation of platelets with preserved hemostatic activity as well as methods for making a pharmaceutical composition containing the preserved platelets and for administering the pharmaceutical composition to a mammal to mediate hemostasis. Also provided are kits for treating a platelet preparation for storage, and containers for storing the same.

In one aspect of the invention, the method for increasing circulation time of an isolated population of platelets involves contacting an isolated population of platelets with at least one glycan modifying agent in an amount effective to reduce the clearance of the population of platelets. As used herein, a population of platelets refers to a sample having one or more platelets. A population of platelets includes a platelet concentrate. The term "isolated" means separated from its native environment and present in sufficient quantity to permit its identification or use. As used herein with respect to a population of platelets, isolated means removed or cleared from the blood circulation of a mammal. The circulation time of a population of platelets is defined as the time when one-half of the platelets in that population are no longer circulating in a mammal after transplantation into that mammal. As used herein, "clearance" means removal of the modified platelets from the blood circulation of a mammal (such as but not limited to by macrophage phagocytosis). As used herein, clearance of a population of platelets refers to the removal of a population of platelets from a unit volume of blood or serum per unit of time. Reducing the clearance of a population of platelets refers to preventing, delaying, or reducing the clearance of the population of platelets. Reducing clearance of platelets also may mean reducing the rate of platelet clearance.

A glycan modifying agent refers to an agent that modifies glycan residues on the platelet. As used herein, a "glycan" or "glycan residue" is a polysaccharide moiety on surface of the platelet, exemplified by the GP1bα polysaccharide. A "terminal" glycan or glycan residue is the glycan at the distal terminus of the polysaccharide, which typically is attached to polypeptides on the platelet surface. Preferably, the glycan modifying agent alters GP1bα on the surface of the platelet.

The glycan modifying agents suitable for use as described herein, includes monosaccharides such as arabinose, fructose, fucose, galactose, mannose, ribose, gluconic acid, galactosamine, glucosamine, N-acetylgalactosamine, muramic acid, sialic acid (N-acetylneuraminic acid), and nucleotide sugars such as cytidine monophospho-N-acetyl-neuraminic acid (CMP-sialic acid), uridine diphosphate galactose (UDP-galactose) and UDP-galactose precursors such as UDP-glucose. In some preferred embodiments, the glycan modifying agent is UDP-galactose or CMP-sialic acid.

UDP-galactose is an intermediate in galactose metabolism, formed by the enzyme UDP-glucose-α-D-galactose-1-phosphate uridylyltransferase which catalyzes the release of glucose-1-phosphate from UDP-glucose in exchange for galactose-1-phosphate to make UDP-galactose. UDP-galactose and sialic acid are widely available from several commercial suppliers such as Sigma. In addition, methods for synthesis and production of UDP-galactose are well known in the art and described in the literature (see for example, Liu et al, ChemBioChem 3, 348-355, 2002; Heidlas et al, J. Org. Chem. 57, 152-157; Butler et al, Nat. Biotechnol. 8, 281-284, 2000; Koizumi et al, Carbohydr. Res. 316, 179-183, 1999; Endo et al, Appl. Microbiol., Biotechnol. 53, 257-261, 2000). UDP-galactose precursors are molecules, compounds, or intermediate compounds that may be converted (e.g., enzymatically or biochemically) to UDP-galactose. One non-limiting example of a UDP-galactose precursor is UDP-glucose. In certain embodiments, an enzyme that converts a UDP-galactose precursor to UDP-galactose is added to a reaction mixture (e.g. in a platelet container).

An effective amount of a glycan modifying agent is that amount of the glycan modifying agent that alters a sufficient number of glycan residues on the surface of platelets, that when introduced to a population of platelets, increases circulation time and/or reduces the clearance of the population of platelets in a mammal following transplantation of the platelets into the mammal. An effective amount of a glycan modifying agent is a concentration from about 1 micromolar to about 1200 micromolar, preferably from about 10 micromolar to about 1000 micromolar, more preferably from about 100 micromolar to about 750 micromolar, and most preferably from about 200 micromolar to about 600 micromolar.

Modification of platelets with glycan modifying agents can be preformed as follows. The population of platelets is incubated with the selected glycan modifying agent (concentrations of 1-1200 µM) for at least 1, 2, 5, 10, 20, 40, 60, 120, 180, 240, or 300 min. at 22° C.-37° C. Multiple glycan modifying agents (i.e., two, three four or more) may be used simultaneously or sequentially. In some embodiments 0.1-500 mU/ml galactose transferase or sialyl transferase is added to the population of platelets. Galactose transfer can be monitored functionally using FITC-WGA (wheat germ agglutinin) binding. The goal of the glycan modification reaction is to reduce WGA binding to resting room temperature WGA binding-levels. Galactose transfer can be quantified using $^{14}$C-UDP-galactose. Non-radioactive UDP-galactose is mixed with $^{14}$C-UDP-galactose to obtain appropriate galactose transfer. Platelets are extensively washed, and the incorporated radioactivity measured using a γ-counter. The measured cpm permits calculation of the incorporated galactose. Similar techniques are applicable to monitoring sialic acid transfer.

Reducing the clearance of a platelet encompasses reducing clearance of platelets after storage at room temperature, or after chilling, as well as "cold-induced platelet activation". Cold-induced platelet activation is a term having a particular meaning to one of ordinary skill in the art. Cold-induced platelet activation may manifest by changes in platelet morphology, some of which are similar to the changes that result following platelet activation by, for example, contact with glass. The structural changes indicative of cold-induced platelet activation are most easily identified using techniques such as light or electron microscopy. On a molecular level, cold-induced platelet activation results in actin bundle formation and a subsequent increase in the concentration of intracellular calcium. Actin-bundle formation is detected using, for example, electron microscopy. An increase in intracellular calcium concentration is determined, for example, by employing fluorescent intracellular calcium chelators. Many of the above-described chelators for inhibiting actin filament severing are also useful for determining the concentration of intracellular calcium (Tsien, R., 1980, supra.). Accordingly, various techniques are available to determine whether or not platelets have experienced cold-induced activation.

The effect of galactose or sialic acid addition to the glycan moieties on platelets, resulting in diminished clearance of modified platelets, can be measured for example using either an in vitro system employing differentiated THP-1 cells or murine macrophages, isolated from the peritoneal cavity after thioglycolate injection stimulation. The rate of clearance of modified platelets compared to unmodified platelets is determined. To test clearance rates, the modified platelets are fed to the macrophages and ingestion of the platelets by the macrophages is monitored. Reduced ingestion of modified platelets relative to unmodified platelets (twofold or greater) indicates successful modification of the glycan moiety for the purposes described herein.

In accordance with the invention, the population of modified platelets can be chilled without the deleterious effects (cold-induced platelet activation) usually experienced on chilling of untreated platelets. The population of modified platelets can be chilled prior to, concurrently with, or after contacting the platelets with the at least one glycan modifying agent. The selective modification of glycan moieties reduces clearance, following chilling (also if not chilled), thus permitting longer-term storage than is presently possible. As used herein, chilling refers to lowering the temperature of the population of platelets to a temperature that is less than about 37° C. In some embodiments, the platelets are chilled to a temperature that is less than about 15° C. In some preferred embodiments, the platelets are chilled to a temperature ranging from between about 0° C. to about 4° C. Chilling also encompasses freezing the platelet preparation, i.e., to temperatures less than 0° C., −20° C., −50° C., and −80° C. or cooler. Process for the cryopreservation of cells are well known in the art.

In some embodiments, the population of platelets is stored chilled for at least 3 days. In some embodiments, the population of platelets is stored chilled for at least 5, 7, 10, 14, 21, and 28 days or longer.

In some embodiments of the invention, the circulation time of the population of platelets is increased by at least about 10%. In some other embodiments, the circulation time of the population of platelets is increased by at least about 25%. In yet some other embodiments, the circulation time of the population of platelets is increased by at least about 50% to about 100%. In still yet other embodiments, the circulation time of the population of platelets is increased by about 150% or greater.

The invention also embraces a method for increasing the storage time of platelets. As used herein the storage time of platelets is defined as the time that platelets can be stored without substantial loss of platelet function or hemostatic activity such as the loss of the ability to circulate or increased platelet clearance.

The platelets are collected from peripheral blood by standard techniques known to those of ordinary skill in the art, for example by isolation from whole blood or by apheresis processes. In some embodiments, the platelets are contained in a pharmaceutically-acceptable carrier prior to treatment with a glycan modifying agent.

According to another aspect of the invention, a modified platelet or a population of modified platelets is provided. The modified platelet comprises a plurality of modified glycan molecules on the surface of the platelet. In some embodiments, the modified glycan moieties are GP1bα, molecules. The invention also encompasses a platelet composition in a storage medium. In some embodiments the storage medium comprises a pharmaceutically acceptable carrier.

The term "pharmaceutically acceptable" means a non-toxic material that does not interfere with the effectiveness of the biological activity of the platelets and that is a non-toxic material that is compatible with a biological system such as a cell, cell culture, tissue, or organism. Pharmaceutically acceptable carriers include diluents, fillers, salts, buffers, stabilizers, solubilizers, and other materials which are well known in the art, for example, a buffer that stabilizes the platelet preparation to a pH of 7.4, the physiological pH of blood, is a pharmaceutically acceptable composition suitable for use with the present invention.

The invention further embraces a method for making a pharmaceutical composition for administration to a mammal. The method comprises preparing the above-described platelet preparation, and warming the platelet preparation. In some embodiments, the method comprises neutralizing, removing or diluting the glycan modifying agent(s) and/or the enzyme(s) that catalyze the modification of the glycan moiety, and placing the modified platelet preparation in a pharmaceutically acceptable carrier. In a preferred embodiment, the chilled platelets are warmed to room temperature (about 22° C.) prior to neutralization or dilution. In some embodiments, the platelets are contained in a pharmaceutically acceptable carrier prior to contact with the glycan modifying agent(s) with or without the enzyme(s) that catalyze the modification of the glycan moiety and it is not necessary to place the platelet preparation in a pharmaceutically acceptable carrier following neutralization or dilution.

As used herein, the terms "neutralize" or "neutralization" refer to a process by which the glycan modifying agent(s) and/or the enzyme(s) that catalyze the modification of the glycan moiety are rendered substantially incapable of glycan modification of the glycan residues on the platelets, or their concentration in the platelet solution is lowered to levels that are not harmful to a mammal, for example, less that 50 micromolar of the glycan modifying agent. In some embodiments, the chilled platelets are neutralized by dilution, e.g., with a suspension of red blood cells. Alternatively, the treated platelets can be infused into the recipient, which is equivalent to dilution into a red blood cell suspension. This method of neutralization advantageously maintains a closed system and minimizes damage to the platelets. In a preferred embodiment of glycan modifying agents, no neutralization is required.

An alternative method to reduce toxicity is by inserting a filter in the infusion line, the filter containing, e.g. activated charcoal or an immobilized antibody, to remove the glycan modifying agent(s) and/or the enzyme(s) that catalyze the modification of the glycan moiety.

Either or both of the glycan modifying agent(s) and the enzyme(s) that catalyze the modification of the glycan moiety also may be removed or substantially diluted by washing the modified platelets in accordance with standard clinical cell washing techniques.

The invention further provides a method for mediating hemostasis in a mammal. The method includes administering the above-described pharmaceutical preparation to the mammal. Administration of the modified platelets may be in accordance with standard methods known in the art. According to one embodiment, a human patient is transfused with red blood cells before, after or during administration of the modified platelets. The red blood cell transfusion serves to dilute the administered, modified platelets, thereby neutralizing the glycan modifying agent(s) and the enzyme(s) that catalyze the modification of the glycan moiety.

The dosage regimen for mediating hemostasis using the modified platelets is selected in accordance with a variety of factors, including the type, age, weight, sex and medical condition of the subject, the severity of the disease, the route and frequency of administration. An ordinarily skilled physician or clinician can readily determine and prescribe the effective amount of modified platelets required to mediate hemostasis.

The dosage regimen can be determined, for example, by following the response to the treatment in terms clinical signs and laboratory tests. Examples of such clinical signs and laboratory tests are well known in the art and are described, see, Harrison's Principles of Internal Medicine, 15th Ed., Fauci A S et al., eds., McGraw-Hill, New York, 2001.

Also within the scope of the invention are storage compositions and pharmaceutical compositions for mediating hemostasis. In one embodiment, the compositions comprise a pharmaceutically-acceptable carrier, a plurality of modified platelets, a plurality of glycan modifying agent(s) and optionally the enzyme(s) that catalyze the modification of the glycan moiety. The glycan modifying agent(s) and the enzyme(s) that catalyze the modification of the glycan moiety are present in the composition in sufficient amounts so as to reduce platelet clearance. Preferably, glycan modifying agent(s) (and optionally the enzyme(s) that catalyze the modification of the glycan moiety) are present in amounts whereby after chilling and neutralization, the platelets maintain substantially normal hemostatic activity. The amounts of glycan modifying agent(s) (and optionally the enzyme(s) that catalyze the modification of the glycan moiety) which reduce platelet clearance can be selected by exposing a preparation of platelets to increasing amounts of these agents, exposing the treated platelets to a chilling temperature and determining (e.g., by microscopy) whether or not cold-induced platelet activation has occurred. Preferably, the amounts of glycan modifying agent(s) and the enzyme(s) that catalyze the modification of the glycan moiety can be determined functionally by exposing the platelets to varying amounts of glycan modifying agent(s) and the enzyme(s) that catalyze the modification of the glycan moiety, chilling the platelets as described herein, warming the treated (chilled) platelets, optionally neutralizing the platelets and testing the platelets in a hemostatic activity assay to determine whether the treated platelets have maintained substantially normal hemostatic activity.

For example, to determine the optimal concentrations and conditions for preventing cold-induced activation of platelets by modifying them with a glycan modifying agent(s) (and optionally the enzyme(s) that catalyze the modification of the glycan moiety), increasing amounts of these agents are contacted with the platelets prior to exposing the platelets to a chilling temperature. The optimal concentrations of the glycan modifying agent(s) and the enzyme(s) that catalyze the modification of the glycan moiety are the minimal effective concentrations that preserve intact platelet function as determined by in vitro tests (e.g., observing morphological changes in response to glass, thrombin, cryopreservation temperatures; ADP-induced aggregation) followed by in vivo tests indicative of hemostatic function (e.g., recovery, survival and shortening of bleeding time in a thrombocytopenic animal or recovery and survival of $^{51}$Cr-labeled platelets in human subjects).

According to yet another aspect of the invention, a composition for addition to platelets to reduce platelet clearance or to increase platelet storage time is provided. The composition includes one or more glycan modifying agents. In certain embodiments, the composition also includes an enzyme(s) that catalyze the modification of the glycan moiety. The glycan modifying agent and the enzyme(s) that catalyzes the modification of the glycan moiety are present in the composition in amounts that prevent cold-induced platelet activation.

The invention also embraces a storage composition for preserving platelets. The storage composition comprises at least one glycan modifying agent in an amount sufficient to reduce platelet clearance. In some embodiments the storage composition further comprises an enzyme that catalyzes the modification of a glycan moiety on the platelet. The glycan modifying agent is added to the population of platelets that are preferably kept between about room temperature and 37° C. In some embodiments, following treatment, the population of platelets is cooled to about 4° C. In some embodiments, the platelets are collected into a platelet pack, bag, or container according to standard methods known to one of skill in the art. Typically, blood from a donor is drawn into a primary container which may be joined to at least one satellite container, all of which containers are connected and sterilized before use. In some embodiments, the satellite container is connected to the container for collecting platelets by a breakable seal. In some embodiments, the primary container further comprises plasma containing a plurality of platelets.

In some embodiments, the platelets are concentrated (e.g. by centrifugation) and the plasma and red blood cells are drawn off into separate satellite bags (to avoid modification of these clinically valuable fractions) prior to adding the glycan modifying agent with or without the enzyme that catalyzes the modification of a glycan moiety on the platelet. Platelet concentration prior to treatment also may minimize the amounts of glycan modifying agents required for reducing the platelet clearance, thereby minimizing the amounts of these agents that are eventually infused into the patient.

In one embodiment, the glycan modifying agent(s) are contacted with the platelets in a closed system, e.g. a sterile, sealed platelet pack, so as to avoid microbial contamination. Typically, a venipuncture conduit is the only opening in the pack during platelet procurement or transfusion. Accordingly, to maintain a closed system during treatment of the platelets with the glycan modifying agent(s), the agent(s) is placed in a relatively small, sterile container which is attached to the platelet pack by a sterile connection tube (see e.g., U.S. Pat. No. 4,412,835, the contents of which are incorporated herein by reference). The connection tube may be reversibly sealed, or have a breakable seal, as will be known to those of skill in the art. After the platelets are concentrated, e.g. by allowing the platelets to settle and squeezing the plasma out of the primary pack and into a second bag according to standard practice, the seal to the container(s) including the glycan modifying agent(s) is opened and the agents are introduced into the platelet pack. In one embodiment, the glycan modifying agents are contained in separate containers having separate resealable connection tubes to permit the sequential addition of the glycan modifying agents to the platelet concentrate.

Following contact with the glycan modifying agent(s), the treated platelets are chilled. In contrast to platelets stored at, for example, 22° C., platelets stored at cryopreservation temperatures have substantially reduced metabolic activity. Thus, platelets stored at 4° C. are metabolically less active and therefore do not generate large amounts of $CO_2$ compared with platelets stored at, for example, 22° C. (Slichter, S. J., 1981; Vox Sang 40 (Suppl 1), pp 72-86, Clinical Testing and Laboratory-Clinical correlations). Dissolution of $CO_2$ in the platelet matrix results in a reduction in pH and a concomitant reduction in platelet viability (Slichter, S., 1981, supra.). This can be resolved by adding buffers to the platelet population, the buffers selected to keep the platelet population at or near the physiological pH of blood. Likewise, conventional platelet packs are formed of materials that are designed and constructed of a sufficiently permeable material to maximize gas transport into and out of the pack ($O_2$ in and $CO_2$ out). The prior art limitations in platelet pack design and construction are obviated by the instant invention, which permits storage of platelets at cryopreservation temperatures, thereby substantially reducing platelet metabolism and diminishing the amount of $CO_2$ generated by the platelets during storage. Accordingly, the invention further provides platelet containers that are substantially non-permeable to $CO_2$ and/or $O_2$, which containers are useful particularly for cold storage of platelets. In both the gas permeable and non-gas permeable embodiments, the invention provides for a blood storage container having therein, a quantity of a glycan modifying agent sufficient to substantially modify the carbohydrates of the platelets introduced therein, such that the platelets become capable of cold storage and subsequent in vivo circulation.

The present invention also provides for kits that are used for platelet collection, processing and storage, further including suitable packaging materials and instructions for using the kit contents. It is preferred that all reagents and supplies in the kit be sterile, in accordance with standard medical practices involving the handling and storage of blood and blood products. Methods for sterilizing the kit contents are known in the art, for example, ethylene gas, irradiation and the like. In certain embodiments, the kit may include venipuncture supplies and/or blood collection supplies, for example a needle set, solution for sterilizing the skin of a platelet donor, and a blood collection bag or container. Preferably the container is "closed", i.e., substantially sealed from the environment. Such closed blood collection containers are well known in the art, and provide a means of preventing microbial contamination of the platelet preparation contained therein. Other embodiments include kits containing supplies for blood collection and platelet apheresis. The kits may further include a quantity of the glycan modifying agent, sufficient to modify the volume of platelets collected and stored in the container. In certain embodiments, the kit includes reagents for modifying the terminal glycan of platelets with a second or third chemical moiety, for example to PEGylate collected platelets. In other embodiments, the kit includes a blood collection system having a blood storage container wherein the glycan modifying agent is provided within the container in an amount sufficient to treat the volume of blood or platelets held by the container. The quantity of glycan modifying agent will depend on the volume of the container. It is preferred the glycan modifying agent be provided as a sterile non-pyrogenic solution, but it may also be supplied as a lyophilized powder. For example, a blood bag is provided having a capacity of 250 ml. Contained in the blood bag is a quantity of UDP-Gal such that when 250 ml of blood is added, the final concentration of the UDP-Gal is approximately 200 micromolar. Other embodiments contain different concentrations of glycan modifying agents, for example but not limited to quantities resulting in final concentrations of 10 micromolar to 10 millimolar, and preferably 100 micromolar to 1 millimolar of the glycan modifying agents. Other embodiments use combinations of glycan modifying agents, e.g., to effect sialylation or galactosylation of N-linked glycoproteins on blood products introduced into the container.

The invention will be more fully understood by reference to the following examples. These examples, however, are merely intended to illustrate the embodiments of the invention and are not to be construed to limit the scope of the invention.

EXAMPLES

Example 1

Introduction

Modest cooling primes platelets for activation, but refrigeration causes shape changes and rapid clearance, compromising storage of platelets for therapeutic transfusions. We found that shape change inhibition does not normalize cold-induced clearance. We also found that cooling platelets rearranges the surface configuration of the von Willebrand factor (vWf) receptor complex α subunit (GP1bα) such that it becomes targeted for recognition by complement receptor 3 receptors (CR3) predominantly expressed on liver macrophages, leading to platelet phagocytosis and clearance. GP1b α removal prolongs survival of unchilled platelets. Chilled platelets bind vWf and function normally in vitro and ex vivo after transfusion into CR3-deficient mice. Cooled platelets, however, are not "activated" like platelets exposed to thrombin or ADP, and their vWf-receptor complex reacts normally with activated vWf.

As the temperature falls below 37° C. platelets become more susceptible to activation by thrombotic stimuli, a phenomenon known as "priming" (Faraday and Rosenfeld, 1998; Hoffmeister et al., 2001). Priming may be an adaptation to limit bleeding at lower temperatures of body surfaces where most injuries occur. We propose that the hepatic clearance system's purpose is to remove repeatedly primed platelets, and that conformational changes in GP1bα that promote this clearance do not affect GP1bα's hemostatically important binding to vWf. Therefore, selective modification of GP1bα may accommodate cold storage of platelets for transfusion.

Materials and Methods

We obtained fluorescein isothiocyanate (FITC)-conjugated annexin V, phycoerythrin (PE)-conjugated anti-human CD11b/Mac-1 monoclonal antibodies (mAb), FITC-conjugated anti-mouse and anti-human IgM mAb, FITC-conjugated anti-mouse and anti-human CD62P-FITC mAb from Pharmingen (San Diego, Calif.); FITC-conjugated rat anti-mouse anti-human IgG mAb from Santa Cruz Biotechnology, Inc. (Santa Cruz, Calif.); FITC-conjugated anti-human CD61 mAbs (clone BL-E6) from Accurate Scientific Corp. (Westbury, N.Y.); FITC-conjugated anti-human GP1bα mAb (clone SZ2) from Immunotech (Marseille, France); and FITC-conjugated polyclonal rabbit anti-vWf antibody from DAKOCytomation (Glostrup, Denmark). We purchased EGTA-acetoxymethylester (AM), Oregon Green coupled fibrinogen from human plasma, CellTracker™ Orange CMTMR; CellTracker Green CMFDA, Nile-red (535/575) coupled and carboxylate-modified 1 µm microspheres/Fluo-Spheres from Molecular Probes, Inc. (Eugene, Oreg.) and $^{111}$Indium from NEN Life Science Products (Boston, Mass.). We purchased Cytochalasin B, dimethyl sulfoxide (DMSO), trisodium isothiocyanate (TRITC), human thrombin, prostaglandin E1 ($PGE_1$), phorbol ester 12-tetradecanoylphorbol-13 acetate (PMA), A23187 ionophore from Sigma (St. Louis, Mo.); botrocetin from Centerchem Inc. (Norwalk, Conn.); and O-sialoglycoprotein-endopeptidase from Cerladane (Hornby, Canada). HBSS containing $Ca^{2+}$ and $Mg^{2+}$, pH 6.4; RPMI 1640; 0.05% Trypsin-EDTA (0.53 mM) in HBSS without $Ca^{2+}$ and $Mg^{2+}$; and other supplements (penicillin, streptomycin and fetal bovine serum) were from GIBCO Invitrogen Corp. (Grand Island, N.Y.). TGF-β1 from Oncogene Research Products (Cambridge, Mass.); 1,25-$(OH)_2$ vitamin D3 from Calbiochem (San Diego, Calif.); and Adenosine-5'-Diphosphate (ADP) were from USB (Cleveland, Ohio). Avertin (2,2,2-tribromoethanol) was purchased from Fluka Chemie (Steinheim, Germany). Collagen related peptide (CRP) was synthesized at the Tufts Core Facility, Physiology Dept. (Boston, Mass.) and cross-linked as previously described (Morton et al., 1995). Mocarhagin, a snake venom metalloprotease, was provided by Dr. M. Berndt, Baker Medical Research Institute, Melbourne Victoria 318 1, Australia. Additional unconjugated anti mouse GP1bα mAbs and a PE-conjugated anti-mouse GP1bα mAb pOp4 were provided by Dr. B. Nieswandt (Witten/Herdecke University, Wuppertal, Germany). We obtained THP-1 cells from the American Type Culture Collection (Manassas, Va.).

Animals

For assays of clearance and survival studies, we used age-, strain- and sex-matched C57BL/6 and C57BL/6×129/sv wild type mice obtained from Jackson Laboratory (Bar Harbor, Me.). C57BL/6×129/sv mice deficient in complement component C3 (Wessels et al., 1995) were provided by Dr. M. C. Carroll (Center for Blood Research and Department of Pediatrics, Harvard Medical School, Boston, Mass.). C57BL/6 mice deficient in CR3 (Coxon et al., 1996) were provided by Dr. T Mayadas and C57BL/6 mice deficient in vWf (Denis et al., 1998) were provided by Dr. D. Wagner. Mice were maintained and treated as approved by Harvard Medical Area Standing Committee on Animals according to NIH standards as set forth in The Guide for the Care and Use of Laboratory Animals.

Human Platelets

Blood was drawn from consenting normal human volunteers (approval was obtained from the Institutional Review Boards of both Brigham and Women's Hospital and the Center for Blood Research (Harvard Medical School)) by venipuncture into 0.1 volume of Aster-Jandl citrate-based anticoagulant (Hartwig and DeSisto, 1991) and platelet rich plasma (PRP) was prepared by centrifugation of the anticoagulated blood at 300×g for 20 min at room temperature. Platelets were separated from plasma proteins by gel-filtration at room temperature through a small Sepharose 2B column (Hoffmeister et al., 2001). Platelets used in the in vitro phagocytosis assay described below were labeled with 1.8 µM CellTracker™ Orange CMTMR (CM-Orange) for 20 min at 37° C. (Brown et al., 2000), and unincorporated dye was removed by centrifugation (850×g, 5 min.) with 5 volumes of washing buffer containing 140 mM NaCl, 5 mM KCl, 12 mM trisodium citrate, 10 mM glucose, and 12.5 mM sucrose, 1 µg/ml $PGE_1$, pH 6.0 (buffer A). Platelets were resuspended at $3 \times 10^8$/ml in a solution containing 140 mM NaCl, 3 mM KCl, 0.5 mM $MgCl_2$, 5 mM $NaHCO_3$, 10 mM glucose and 10 mM Hepes, pH 7.4 (buffer B).

The N-terminus of GP1bα was enzymatically removed from the surface of chilled or room temperature maintained and labeled platelets in buffer B, also containing 1 mM $Ca^{2+}$ and 10 µg/ml of the snake venom metalloprotease mocarhagin (Ward et al., 1996). After the enzymatic digestion, the platelets were washed by centrifugation with 5× volume of buffer A and routinely checked by microscopy for aggregates. GP1bα-N-terminus removal was monitored by incubating platelet suspensions with 5 µg/ml of FITC-conjugated anti-human GP1bα (SZ2) mAb for 10 min at room temperature and followed by immediate flow cytometry analysis on a FACScalibur Flow Cytometer (Becton Dickinson Biosciences, San Jose, Calif.). Platelets were gated by forward/side scatter characteristics and 50,000 events acquired.

Murine Platelets

Mice were anesthetized with 3.75 mg/g (2.5%) of Avertin, and 1 ml blood was obtained from the retroorbital eye plexus into 0.1 volume of Aster-Jandl anticoagulant. PRP was prepared by centrifugation of anticoagulated blood at 300×g for 8 min at room temperature. Platelets were separated from plasma proteins by centrifugation at 1200×g for 5 min and washed two times by centrifugation (1200×g for 5 min) using 5× volumes of washing buffer (buffer A). This procedure is meant by subsequent use of the term "washed". Platelets were resuspended at a concentration of $1 \times 10^9$/ml in a solution containing 140 mM NaCl, 3 mM KCl, 0.5 mM $MgCl_2$, 5 mM $NaHCO_3$, 10 mM glucose and 10 mM Hepes, pH 7.4 (buffer B). Platelet count was determined using a Bright Line Hemocytometer (Hausser Scientific, Horsham, Pa.) under a phase-contrast microscope at 400× magnification. Some radioactive platelet clearance studies were performed with $^{111}$Indium, and we labeled mouse platelets using a method described for primate platelets (Kotze et al., 1985). Platelets were resuspended at a concentration of $2 \times 10^9$/ml in 0.9% NaCl, pH 6.5 (adjusted with 0.1 M sodium citrate), followed by the addition of 500 µCi $^{111}$Indium chloride for 30 min at 37° C. and washed as described above and suspended in buffer B at a concentration of $1 \times 10^9$/ml.

For intravital microscopy or other platelet survival experiments, washed platelets were labeled either with 2.5 µM CellTracker Green CMFDA (5-chloromethyl fluorescein diacetate) (CMFDA) for 20 min at 37° C. (Baker et al., 1997) or with 0.15 µM TRITC for 20 min at 37° C. in buffer B also containing 0.001% DMSO, 20 mM HEPES. Unincorporated dye was removed by centrifugation as described above, and platelets were suspended at a concentration of $1\times10^9$/ml in buffer B.

The N-terminus of GP1bα was enzymatically removed from the surface of chilled or room temperature labeled platelets with 100 µg/ml O-sialoglycoprotein endopeptidase in buffer B containing 1 mM $Ca^{2+}$ for 20 min at 37° C. (Bergmeier et al., 2001). After enzymatic digestion, platelets were washed by centrifugation and checked by light microscopy for aggregates. Enzymatic removal of the GP1bα-N-terminus removal was monitored by incubating the platelet suspensions with 5 µg/ml of PE-conjugated anti-mouse GP1bα mAb pOp4 for 10 min at room temperature, and bound PE analyzed by flow cytometry.

To inhibit cold-induced platelet shape changes, $10^9$/ml platelets in buffer B were loaded with 2 µM EGTA-AM followed by 2 µM cytochalasin B as previously described (Winokur and Hartwig, 1995), labeled with 2.5 µM CMFDA for 30 min at 37° C. and then chilled or maintained at room temperature. The platelets were subjected to standard washing and suspended at a concentration of $1\times10^9$/ml in buffer B before injection into mice.

Platelet Temperature Protocols

To study the effects of temperature on platelet survival or function, unlabeled, radioactively labeled, or fluorescently-labeled mouse or human platelets were incubated for 2 hours at room temperature (25-27° C.) or else at ice bath temperatures and then rewarmed for 15 minutes at 37° C. before transfusion into mice or in vitro analysis. Platelets subjected to these treatments are designated cooled or chilled (or chilled, rewarmed) and room temperature platelets respectively.

Murine Platelet Recovery, Survival and Fate

CMFDA labeled chilled or room temperature murine platelets ($10^8$) were injected into syngeneic mice via the lateral tail vein using a 27-gauge needle. For recovery and survival determination, blood samples were collected immediately (<2 min) and 0.5, 2, 24, 48, 72 hours after transfusion into 0.1 volume of Aster-Jandl anticoagulant. Whole blood analysis using flow cytometry was performed and the percentage of CMFDA positive platelets determined by gating on all platelets according to their forward and side scatter characteristics (Baker et al., 1997). 50,000 events were collected in each sample. CMFDA positive platelets measured at a time <2 min was set as 100%. The input of transfused platelets per mouse was ~2.5-3% of the whole platelet population.

To evaluate the fate of platelets, tissues (heart, lung, liver, spleen, muscle, and femur) were harvested at 0.5, 1 and 24 hours after the injection of $10^8$ chilled or room temperature $^{111}$Indium labeled platelets into mice. The organ-weight and their radioactivity were determined using a Wallac 1470 Wizard automatic gamma counter (Wallac Inc., Gaithersburg, Md.). The data were expressed as gamma count per gram organ. For recovery and survival determination of radioactive platelets, blood samples were collected immediately (<2 min) and 0.5 and hours after transfusion into 0.1 volume of Aster-Jandl anticoagulant and their gamma counts determined (Kotze et al., 1985).

Platelet Aggregation

Conventional tests were performed and monitored in a Bio/Data aggregometer (Horsham, Pa.). Samples of 0.3-ml murine washed and stirred platelets were exposed to 1 U/ml thrombin, 10 µM ADP, or 3 µg/ml CRP at 37° C. Light transmission was recorded over 3 min.

Activated VWf Binding

Platelet rich plasma was treated with or without 2 U/ml botrocetin for 5 min at 37° C. (Bergmeier et al., 2001). Bound vWf was detected by flow cytometry using FITC conjugated polyclonal rabbit anti-vWf antibody.

Surface Labeling of Platelet GP1bα

Resting mouse platelets maintained at room temperature or chilled 2 hrs were diluted to a concentration of $2\times10^6$/ml in phosphate buffered saline (PBS) containing 0.05% glutaraldehyde. Platelet solutions (200 µl) were placed on a polylysine-coated glass coverslip contained in wells of 96-well plate, and the platelets were adhered to each coverslip by centrifugation at 1,500×.g for 5 min at room temperature. The supernatant fluid was then removed, and platelets bound to the coverslip were fixed with 0.5% glutaraldehyde in PBS for 10 min. The fixative was removed, unreacted aldehydes quenched with a solution containing 0.1% sodium borohydride in PBS followed by washing with PBS containing 10% BSA. GP1bα on the platelet surface was labeled with a mixture of three rat anti-mouse GP1bα monoclonal antibodies, each at 10 µg/ml (Bergmeier et al., 2000) for 1 hr followed by 10 nm gold coated with goat anti-rat IgG. The coverslips were extensively washed with PBS, post-fixed with 1% glutaraldehyde, washed again with distilled water, rapidly frozen, freeze-dried, and rotary coated with 1.2 nm of platinum followed by 4 nm of carbon without rotation in a Cressington CFE-60 (Cressington, Watford, UK). Platelets were viewed at 100 kV in a JEOL 1200-EX electron microscope (Hartwig et al., 1996; Kovacsovics and Hartwig, 1996)

In Vitro Phagocytic Assay

Figure 6A:
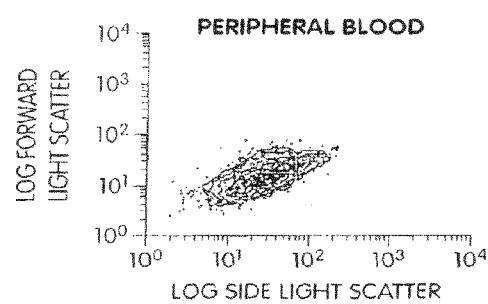
FIG. 6 shows circulating, chilled platelets have hemostatic function in CR3 deficient mice. Normal in vivo function of room temperature (RT) platelets transfused into wild type mice (FIGS. 6A and 6B) and of chilled (Cold) platelets transfused into CR3 deficient mice (FIGS. 6C and 6D), as determined by their equivalent presence in platelet aggregates emerging from the wound 24 hrs after infusion of autologous CMFDA labeled platelets. Peripheral blood (FIGS. 6A and 6C) and the blood emerging from the wound (shed blood, FIGS. 6B and 6D) were analyzed by whole blood flow cytometry. Platelets were identified by forward light scatter characteristics and binding of the PE-conjugated anti-GP1bα mAb (pOp4). The infused platelets (dots) were identified by their CMFDA fluorescence and the non-infused platelets (contour lines) by their lack of CMFDA fluorescence. In the peripheral whole blood samples, analysis regions were plotted around the GP1bα-positive particles to include 95% of the population on the forward scatter axis (region 1) and the 5% of particles appearing above this forward light scatter threshold were defined as aggregates (region 2). The percentages refer to the number of aggregates formed by CMFDA-positive platelets. This shown result is representative of 4 experiments.
FIG. 6E shows ex vivo function of CM-Orange, room temperature (RT) platelets transfused into wild type mice and CM-Orange, chilled-rewarmed (Cold) platelets transfused into CR3 deficient mice, as determined by exposure of P-selectin and fibrinogen binding following thrombin (1 U/ml) activation of blood drawn from the mice after 24 hours post infusion. CM-Orange labeled platelets have a circulation half-life time comparable to that of CMFDA labeled platelets (not shown). Transfused platelets were identified by their CM-Orange fluorescence (filled bars). Non-transfused (non-labeled) analyzed platelets are represented as open bars. Results are expressed as the percentage of cells present in the P-selectin and fibrinogen positive regions (region 2). Data are mean±SD for 4 mice.
Figure 6B:
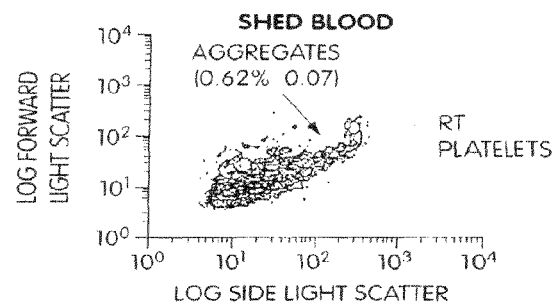
Figure 6C:
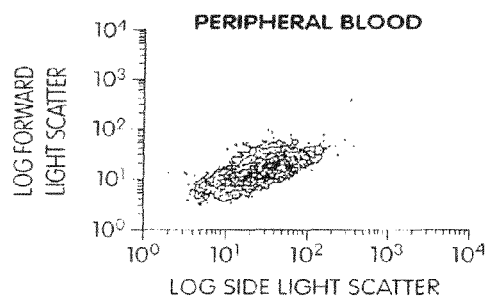
Figure 6D:
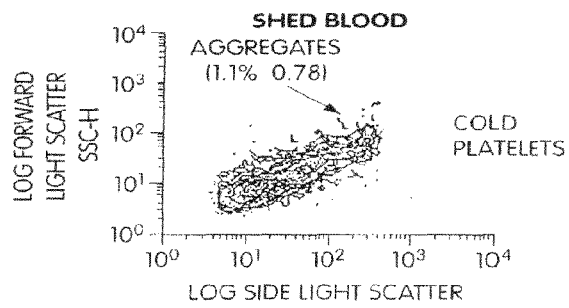

Monocytic THP-1 cells were cultured for 7 days in RPMI 1640 cell culture media supplemented with 10% fetal bovine serum, 25 mM Hepes, 2 mM glutamine and differentiated using 1 ng/ml TGFP and 50 nM $1,25\text{-}(OH)_2$ vitamin D3 for 24 hours, which is accompanied by increased expression of CR3 (Simon et al., 2000). CR3 expression was monitored by flow cytometry using a PE-conjugated anti-human CD11b/Mac-1 mAb. Undifferentiated or differentiated THP-1 cells ($2\times10^6$/ml) were plated onto 24-well plates and allowed to adhere for 45 minutes at 37° C. The adherent undifferentiated or differentiated macrophages were activated by the addition of 15 ng/ml PMA for 15 min. CM-range-labeled, chilled or room temperature platelets ($10^7$/well), previously subjected to different treatments were added to the undifferentiated or differentiated phagocytes in $Ca^{2+}$- and $Mg^{2+}$-containing HBSS and incubated for 30 min at 37° C. Following the incubation period, the phagocyte monolayer was washed with HBSS for 3 times, and adherent platelets were removed by treatment with 0.05% trypsin/0.53 mM EDTA in HBSS at 37° C. for 5 min followed by 5 mM EDTA at 4° C. to detach the macrophages for flow cytometric analysis of adhesion or ingestion of platelets (Brown et al., 2000). Human CM-Orange-labeled, chilled or room temperature platelets all expressed the same amount of the platelet specific marker CD61 as freshly isolated unlabeled platelets (not shown). CM-Orange-labeled platelets incubated with macrophages were resolved from the phagocytes according to their forward and side scatter properties. The macrophages were gated, 10,000 events acquired for each sample, and data analyzed with CELLQuest software (Becton Dickenson). CM-Orange-labeled platelets that associate with the phagocyte population have a shift in orange fluorescence (FIG. 6a and FIG. 6b, ingested, y axis). These platelets were ingested rather than merely adherent, because they failed to dual label with the FITC-conjugated mAb to CD61.

Immunolabeling and Flow Cytometry of Platelets

Washed murine or human platelets ($2\times10^6$) were analyzed for surface expression of CD62P, CD61, or surface bound IgM and IgG after chilling or room temperature storage by staining with fluorophore-conjugated Abs (5 µg/ml) for 10 min at 37° C. Phosphatidylserine exposure by chilled or room temperature platelets was determined by resuspending 5 µl of platelets in 400 µl of HBSS containing 10 mM $Ca^{2+}$ with 10 µg/ml of FITC-conjugated annexin-V. As a positive control for PS exposure, platelet suspensions were stimulated with 1 µM A23187. Fibrinogen binding was determined by the addition of Oregon Green-fibrinogen for 20 min at room temperature. All platelet samples were analyzed immediately by flow cytometry. Platelets were gated by forward and side scatter characteristics.

Intravital Microscopy Experiments

Animal preparation, technical and experimental aspects of the intravital video microscopy setup have been described (von Andrian, 1996). Six to eight week-old mice of both sexes were anesthetized by intraperitoneal injection of a mixture of Xylazine and Ketamin. The right jugular vein was catheterized with PE-10 polyethylene tubing. The lower surface of the left liver lobe was surgically prepared and covered by a glass cover slip for further in vivo microscopy as described (McCuskey, 1986). $10^8$ chilled platelets and room temperature platelets labeled with CMFDA and TRITC respectively were mixed 1:1 and administered intravenously. The circulation of labeled platelets in liver sinusoids was followed by video triggered stroboscopic epi-illumination. Ten video scenes were recorded from 3 centrilobular zones at each indicated time point. The ratio of cooled (CMFDA)/RT (TRITC) adherent platelets in the identical visualized field was calculated. Confocal microscopy was performed using a Radiance 2000 MP confocal-multiphoton imaging system connected to an Olympus BX 50 WJ upright microscope (Biorad, Hercules, Calif.), using a 10× water immersion objective. Images were captured and analyzed with Laser Sharp 2000 software (Biorad) (von Andrian, 2002).

Platelet Aggregation in Shed Blood

We used a flow cytometric method to analyze aggregate formation by platelets in whole blood emerging from a wound as described for primates (Michelson et al., 1994). We injected $10^8$ CMFDA labeled room temperature murine platelets into syngeneic wild type mice and $10^8$ CMFDA labeled, chilled platelets into CR3-deficient mice. Twenty-four hours after the platelet infusion, a standard bleeding time assay was performed, severing a 3-mm segment of a mouse tail (Denis et al., 1998). The amputated tail was immersed in 100 µl 0.9% isotonic saline at 37° C. The emerging blood was collected for 2 min., and 0.1 volume of Aster-Jandl anticoagulant added and followed immediately with 1% paraformaldehyde (final concentration). Peripheral blood was obtained by retroorbital eye plexus bleeding in parallel as described above and immediately fixed with 1% paraformaldehyde (final concentration). To analyze the number of aggregates in vivo by flow cytometry, the shed blood emerging from the bleeding time wound, as well as a peripheral whole blood sample, were diluted and labeled with PE-conjugated anti-murine GP1bα mAb pOp4 (5 µg/ml, 10 min.). Platelets were discriminated from red cells and white cells by gating according to their forward scatter characteristics and GP1bα positivity. A histogram of log forward light scatter (reflecting platelet size) versus GP1bα binding was then generated. In the peripheral whole blood samples, analysis regions were plotted around the GP1bα-positive particles to include 95% of the population on the forward scatter axis (region 1) and the 5% of particles appearing above this forward light scatter threshold (region 2). Identical regions were used for the shed blood samples. The number of platelet aggregates in shed blood as a percentage of the number of single platelets was calculated from the following formula: [(number of particles in region 2 of shed blood)−(number of particles in region 2 of peripheral blood)]÷(number of particles in region 1 of shed blood)× 100%. The infused platelets were identified by their CMFDA labeling and discriminated from the CMFDA negative non-infused platelets.

Flow Cytometric Analysis of Murine Platelet Fibrinogen Binding and P-Selectin Exposure of Circulating Platelets Room temperature CM-Orange-labeled room temperature platelets ($10^8$) were injected into wild type mice and CM-Orange-chilled labeled platelets ($10^8$) into CR3 deficient mice. Twenty-four hours after platelet infusion the mice were bled and the platelets isolated. Resting or thrombin activated (1 U/ml, 5 min) platelet suspensions ($2 \times 10^8$) were diluted in PBS and either stained with FITC-conjugated anti-mouse P-selectin mAb or with 50 µg/ml Oregon Green-conjugated fibrinogen for 20 min at room temperature. Platelet samples were analyzed immediately by flow cytometry. Transfused and non-transfused platelets were gated by their forward scatter and CM-Orange fluorescence characteristics. P-selectin expression and fibrinogen binding were measured for each CM-Orange positive and negative population before and after stimulation with thrombin.

Statistics

The intravital microscopy data are expressed as means±SEM. Groups were compared using the nonpaired t test. P values <0.05 were considered significant. All other data are presented as the mean±SD.

Results

The Clearance of Chilled Platelets Occurs Predominantly in the Liver and is Independent of Platelet Shape.

Figure 1B:
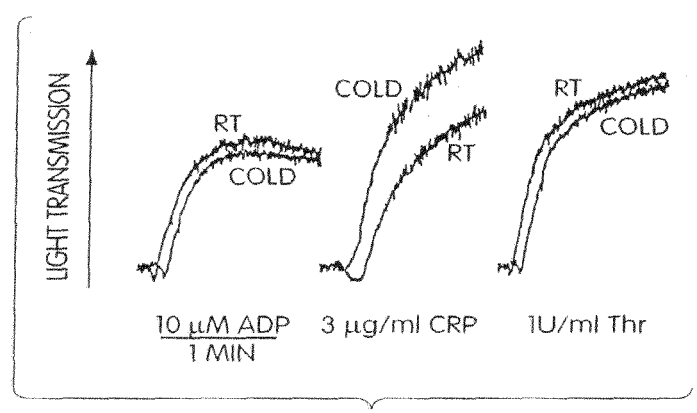
FIG. 1B shows that chilled platelets aggregate normally in vitro. Washed, chilled-rewarmed (Cold) or room temperature (RT) wild type platelets were stimulated by the addition of the indicated agonists at 37° C. and light transmission was recorded on a standard aggregometer. Aggregation responses of chilled platelets treated with EGTA-AM and cytochalasin B were identical to untreated chilled platelets.

Mouse platelets kept at room temperature (RT) and infused into syngeneic mice disappear at fairly constant rate over time for about 80 hours (FIG. 1A). In contrast, approximately two-thirds of mouse platelets chilled at ice-bath temperature and rewarmed (Cold) before injection rapidly disappear from the circulation as observed previously in humans and mice (Becker et al., 1973; Berger et al., 1998). Chilled and rewarmed platelets treated with the cell-permeable calcium chelator EGTA-AM and the actin filament barbed end capping agent cytochalasin B (Cold+CytoB/EGTA) to preserve their discoid shape (Winokur and Hartwig, 1995), left the circulation as rapidly as chilled, untreated platelets despite the fact that these platelets were fully functional as determined by thrombin-, ADP- or collagen related peptide- (CRP) induced aggregation in vitro (FIG. 1B). The recoveries of infused platelets immediately following transfusion were 50-70%, and the kinetics of platelet disappearance were indistinguishable whether we used [111]Indium or CMFDA to label platelets. The relative survival rates of room temperature and chilled mouse platelets resemble the values reported previously for identically treated mouse (Berger et al., 1998) and human platelets (Becker et al., 1973).

Figure 1C:
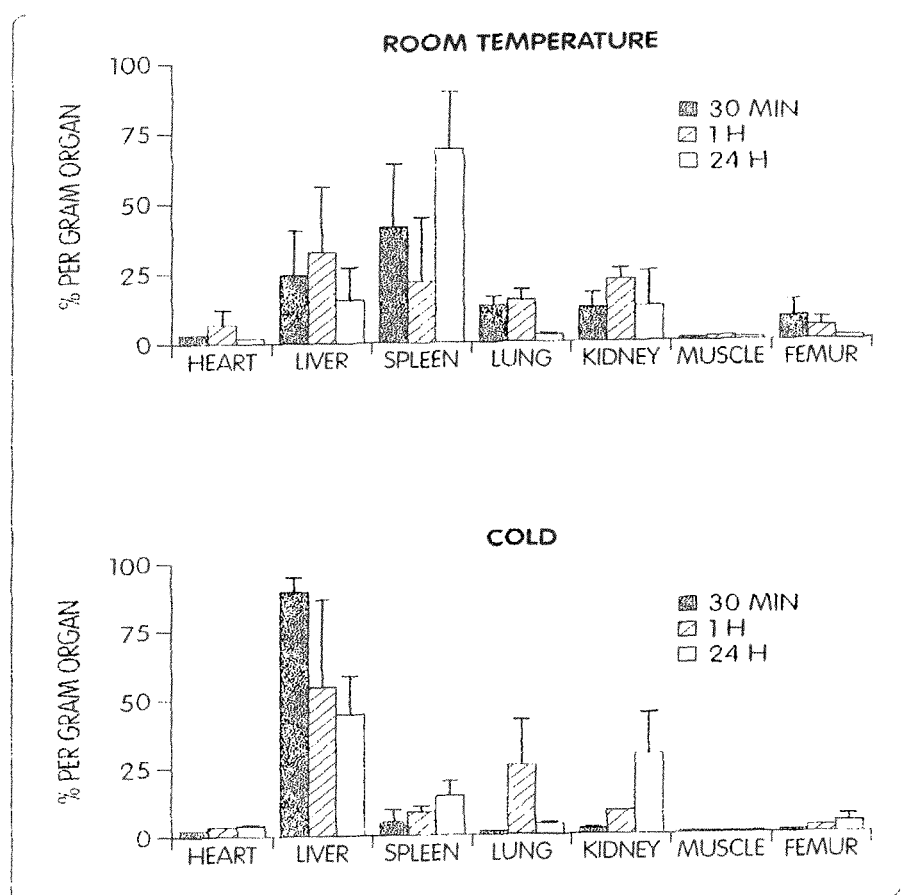
FIG. 1C shows that cold induced clearance occurs predominantly in the liver of mice. The liver is the primary clearance organ of chilled platelets, containing 60-90% of injected platelets. In contrast, RT platelets are cleared more slowly in the spleen. $^{111}$Indium labeled platelets were injected into syngeneic mice and tissues were harvested at 0.5, 1 and 24 hours. Data are expressed per gram of tissue. Each bar depicts the mean values of 4 animals analyzed±SD.

FIG. 1C shows that the organ destinations of room temperature and chilled mouse platelets differ. Whereas room-temperature platelets primarily end up in the spleen, the liver is the major residence of chilled platelets removed from the circulation. A greater fraction of radionuclide detected in the kidneys of animals receiving [111]Indium-labeled chilled compared with room-temperature platelets at 24 hours may reflect a more rapid degradation of chilled platelets and delivery of free radionuclide to the urinary system. One hour after injection the organ distribution of platelets labeled with CMFDA was comparable to that of platelets labeled with [111]Indium. In both cases, 60-90% of the labeled chilled platelet population deposited in the liver, ~20% in the spleen and ~15% in the lung. In contrast, a quarter of the infused room temperature platelets distributed equally among the liver, spleen and lung.

Chilled Platelets Co-Localize with Liver Macrophages (Kupffer Cells).

Figure 1D:
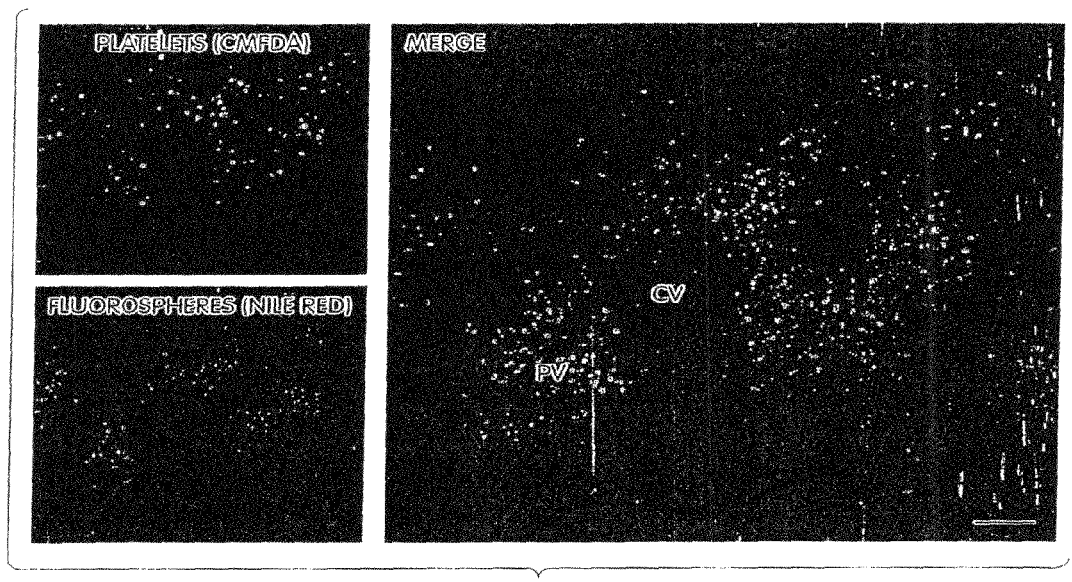
FIG. 1D shows that chilled platelets co-localize with hepatic sinusoidal macrophages (Kupffer cells). This representative confocal-micrograph shows the hepatic distribution of CMFDA-labeled, chilled-rewarmed platelets (green) after 1 hour of transfusion, which preferentially accumulate in periportal and midzonal fields of liver lobules. Kupffer cells were visualized after injection of nile red-labeled spheres. The merged micrograph that shows co-localization of chilled platelets and macrophages in yellow. The lobule organization is indicated (CV: central vein; PV: portal vein, bar: 100 µM).

The clearance of chilled platelets by the liver and the evidence for platelet degradation is consistent with recognition and ingestion of chilled platelets by Kupffer cells, the major phagocytic scavenger cells of the liver. FIG. 1D shows the location of phagocytotic Kupffer cells and adherent chilled CMFDA-labeled platelets in a representative confocal micrograph of a mouse liver section 1 hour after transfusion. Sinusoidal macrophages were visualized by the injection of 1 µM carboxyl modified polystyrene microspheres marked with Nile-red. Co-localization of transfused platelets and macrophages is indicated in yellow in the merged micrograph of both fluorescence emissions. The chilled platelets localize with Nile-red-labeled cells preferentially in the periportal and midzonal domains of liver acini, sites rich in sinusoidal macrophages (Bioulac-Sage et al., 1996; MacPhee et al., 1992).

CR3-Deficient Mice do not Rapidly Clear Chilled Platelets.

Figure 2:
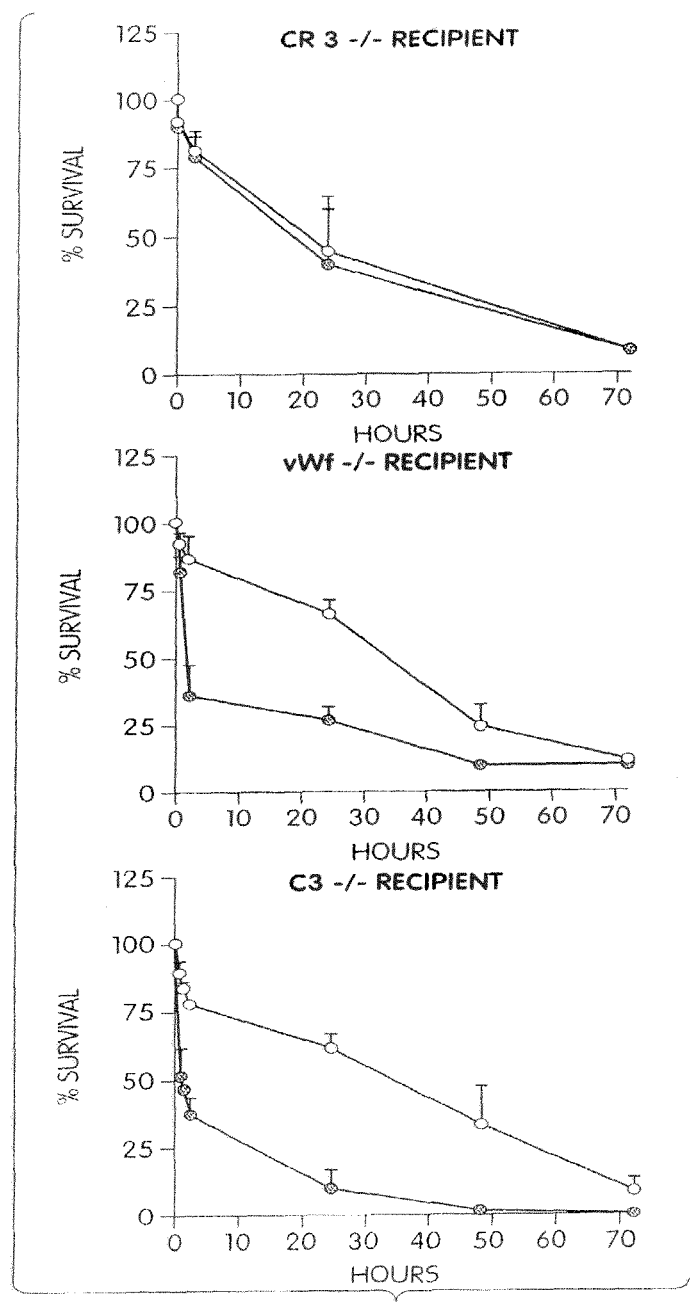
FIG. 2 shows that chilled platelets circulate normally in CR3-deficient mice, but not in complement 3 (C3) or vWf deficient mice. CMFDA-labeled chilled-rewarmed (Cold) and room temperature (RT) wild type platelets were transfused into six each of syngeneic wild type (WT), CR3-deficient (A), vWf-deficient (B) and C3-deficient (C) recipient mice and their survival times determined. Chilled platelets circulate in CR3-deficient animals with the same kinetics as room-temperature platelets, but are cleared rapidly from the circulation of C3- or vWf-deficient mice. Data are mean±SD for 6 mice.

CR3 ($\alpha_M\beta_2$ integrin; CD11b/CD18; Mac-1) is a major mediator of antibody independent clearance by hepatic macrophages. FIG. 2a shows that chilled platelets circulate in CR3-deficient animals with the same kinetics as room-temperature platelets, although the clearance of both platelet populations in the CR3-deficient mouse compared to that in wild-type mice (FIG. 1a). The reason for the slightly faster platelet removal rate by CR3-deficient mice compared to wild-type mice is unclear. Chilled and rewarmed platelets also clear rapidly from complement factor 3 C3-deficient mice (FIG. 2c), missing a major opsonin that promotes phagocytosis and clearance via CR3 and from von Willebrand factor (vWf) deficient mice (Denis et al., 1998) (FIG. 2b).

Chilled Platelets Adhere Tightly to Kupffer Cells In Vivo.

Figure 3A:
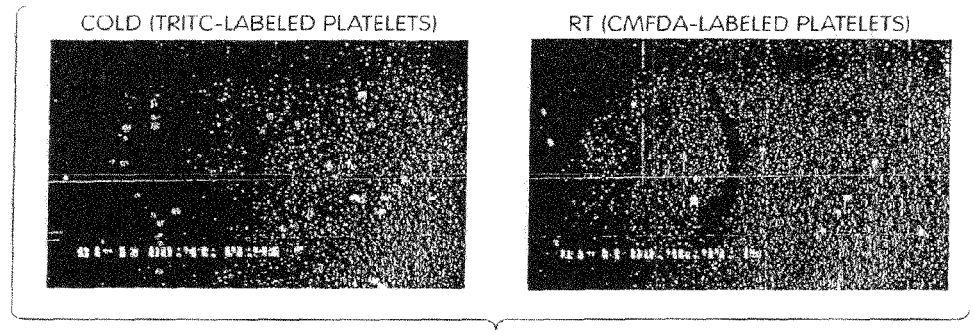
FIG. 3A—Chilled-rewarmed TRITC-labeled platelets (left panel) adhere with a 3-4× higher frequency to liver sinusoids than room temperature CMFDA-labeled platelets (right panel). The intravital fluorescence micrographs were obtained 30 min after the infusion of the platelets.
Figure 3B:
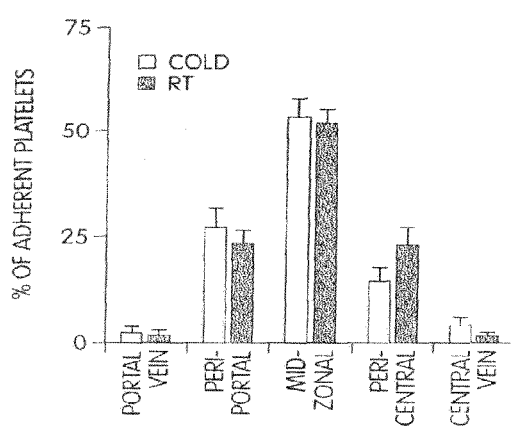
FIG. 3B—Chilled-rewarmed (Cold, open bars) and room temperature platelets (RT, filled bars) adhere to sinusoidal regions with high macrophage density (midzonal) with similar distributions in wild type mice.
Figure 3C:
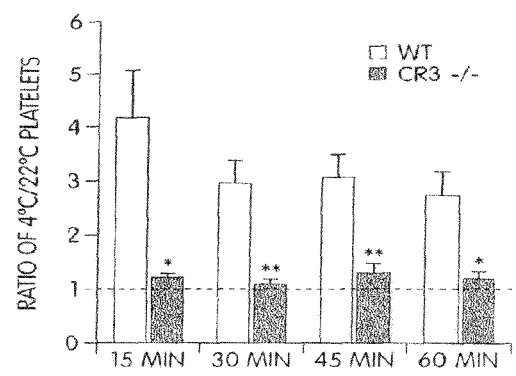
FIG. 3C—Chilled-rewarmed platelets adhere 3-4× more than room temperature platelets to macrophages in the wild type liver (open bars). In contrast, chilled-rewarmed or room temperature platelets have identical adherence to macrophages in CR3-deficient mice (filled bars). 9 experiments with wild type mice and 4 experiments with CR3-deficient mice are shown (mean±SEM, *P<0.05: **P<0.01).

Platelet adhesion to wild-type liver sinusoids was further investigated by intravital microscopy, and the ratio between chilled and room temperature stored adherent platelets infused together was determined. FIG. 3 shows that both chilled and room temperature platelets attach to sinusoidal regions with high Kupffer cell density (FIGS. 3a and 3b), but that 2.5 to 4-times more chilled platelets attach to Kupffer cells in the wild-type mouse than room-temperature platelets (FIG. 3c). In contrast, the number of platelets adhering to Kupffer cells in CR3-deficient mice was independent of chilling or room temperature exposure (FIG. 3c).

Chilled Platelets Lacking the N-Terminal Domain of GP1bα Circulate Normally.

Figure 4A:
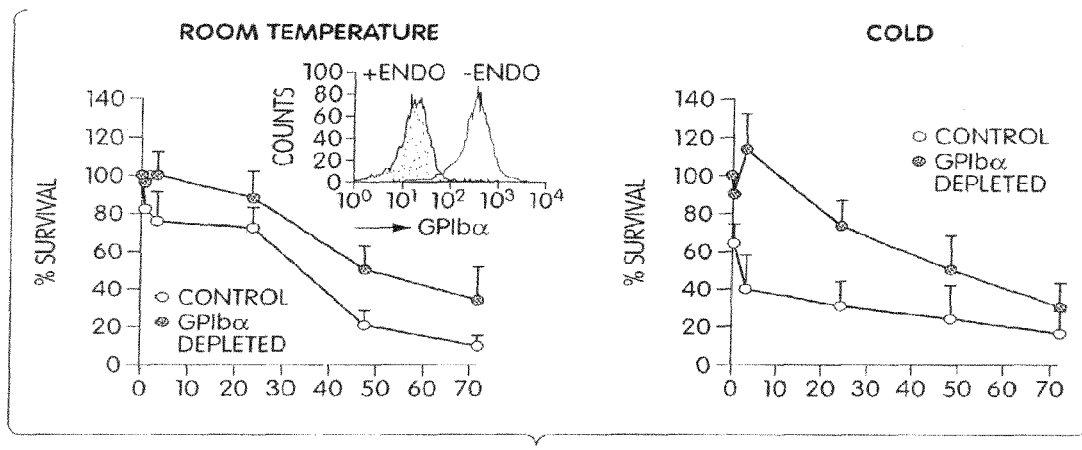
FIG. 4A—CMFDA-labeled platelets enzymatically cleared of the GP1bα extracellular domain (left panel, inset, filled area) or control platelets were kept at room temperature (left panel) or chilled-rewarmed (right panel) infused into syngeneic wild type mice, and platelet survivals were determined. Each survival curve represents the mean values±SD for 6 mice.

Because GP1bα, a component of the GP1b-IX-V receptor complex for vWf, can bind CR3 under certain conditions in vitro (Simon et al., 2000), we investigated GP1bα as a possible counter receptor on chilled platelets for CR3. The O-sialoglycoprotein endopeptidase cleaves the 45-kDa N-terminal extracellular domain of the murine platelet GP1bα, leaving other platelet receptors such as ($\alpha_{IIb}\beta_3$, $\alpha_2\alpha_1$, GPVI/FcRγ-chain and the protease-activated receptors intact (Bergmeier et al., 2001). Hence, we stripped this portion of the extracellular domain of GP1bα from mouse platelets with 0-sialoglycoprotein endopeptidase (FIG. 4A inset) and examined their survival in mice following room temperature or cold incubation. FIG. 4A shows that chilled platelets no longer exhibit rapid clearance after cleavage of GP1bα. In addition, GP1bα depleted room temperature-treated platelets have slightly elongated survival times (~5-10%) when compared to the GP1bα-containing room-temperature controls.

Chilling does not Affect Binding of Activated vWf to the Platelet vWf-Receptor but Induces Clustering of GP1bα on the Platelet Surface.

Figure 4B:
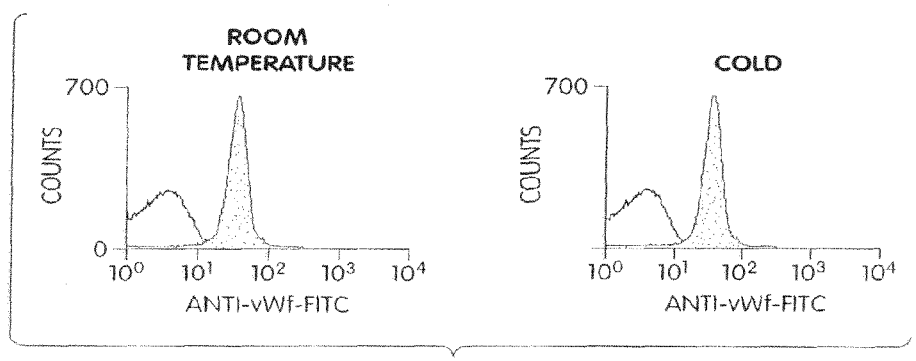
FIG. 4B—Chilled, or RT platelet rich plasma was treated with (shaded area) or without (open area) botrocetin. vWf bound was detected using FITC labeled anti-vWf antibody.
Figure 4C:
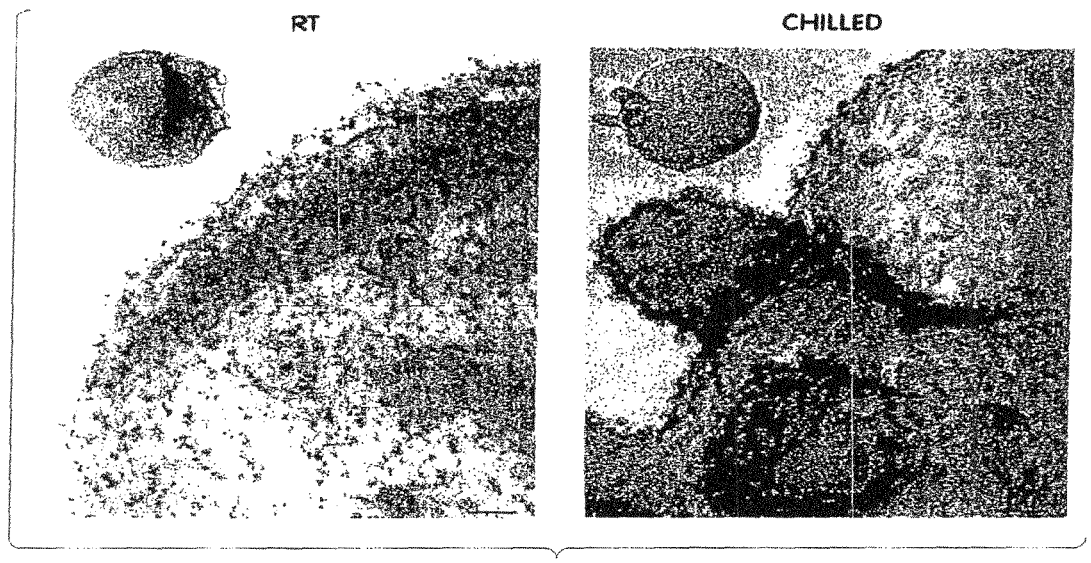
FIG. 4C—The vWf receptor redistributes from linear arrays (RT) into aggregates (Chilled) on the surface of chilled murine platelets. Fixed, chilled-rewarmed, or room temperature platelets (RT) were incubated with monoclonal rat anti-mouse GP1bα antibodies followed by 10 nm colloidal gold particles coated with goat anti-rat IgG. The bars are 100 nm. Inset: low magnification of platelets.

FIG. 4B shows that botrocetin-activated vWf binds GP1bα equally well on room temperature as on cold platelets, although chilling of platelets leads to changes in the distribution of GP1bα on the murine platelet surface. GP1bα molecules, identified by immunogold labeled monoclonal murine anti-GP1bα antibodies, form linear aggregates on the smooth surface of resting discoid platelets at room temperature (FIG. 4C, RT). This arrangement is consistent with information about the architecture of the resting blood platelet. The cytoplasmic domain of GP1bα binds long filaments curving with the plane of the platelet membrane through the intermediacy of filamin A molecules (Hartwig and DeSisto, 1991). After chilling (FIG. 4C, Chilled) many GP1bα molecules organize as clusters over the platelet membrane deformed by internal actin rearrangements (Hoffmeister et al., 2001; Winokur and Hartwig, 1995).

Recognition of Platelet GP1bα by CR3-Mediates Phagocytosis of Chilled Human Platelets In Vitro.

Figure 5A:
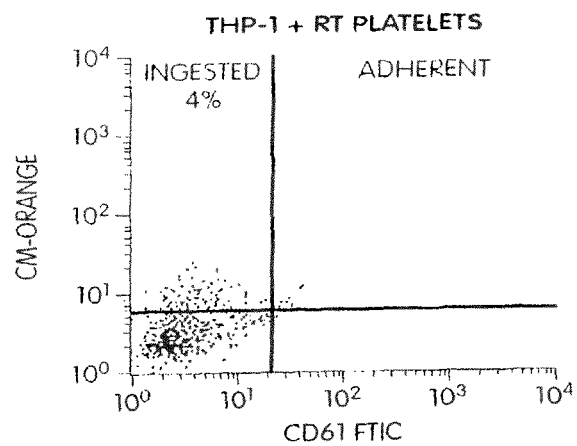
FIGS. 5A and 5B show a representative assay result of THP-1 cells incubated with room temperature (RT) (FIG. 5A) or chilled-rewarmed (Cold) platelets (FIG. 5B). CM-Orange-labeled platelets associated with macrophages shift in orange fluorescence up the y axis. The mean percentage of the CM-Orange positive native macrophages incubated with platelets kept at room temperature was normalized to 1. Chilling of platelets increases this shift from ~4% to 20%. The platelets are predominantly ingested, because they do not dual label with the FITC-conjugated mAb to CD61.
Figure 5B:
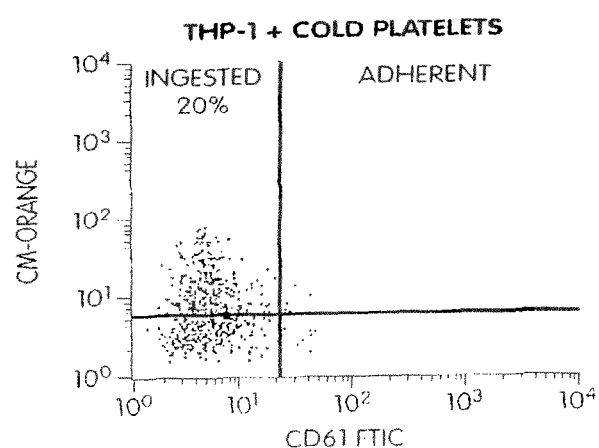
Figure 5C:
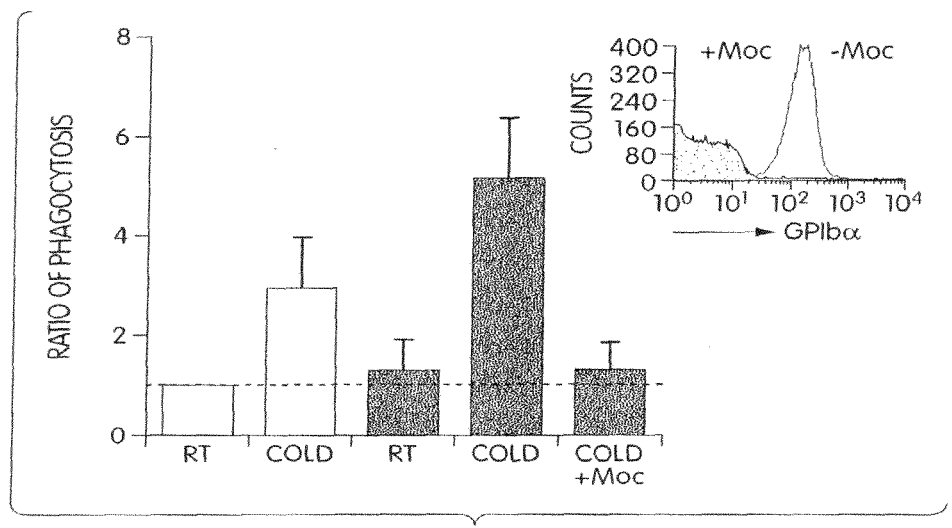
FIG. 5C Undifferentiated (open bars) THP-1 cells express ~50% less CR3, and ingest half as many chilled-rewarmed platelets. Differentiation (filled bars) of CR3 expression however, had no significant effect on the uptake of RT platelets. Treatment of human platelets with the snake venom metalloprotease, mocarhagin (Moc), which removes the N-terminus of GP1bα, from the surface of human platelets (inset; control: solid line, mocarhagin treated platelets: shaded area), reduced phagocytosis of chilled platelets by ~98%. Data shown are means±SD of 5 experiments.

Differentiation of human monocytoid THP-1 cells using TGF-β1 and 1,25-(OH)$_2$ Vitamin D3 increases expression of CR3 by ~2-fold (Simon et al., 1996). Chilling resulted in 3-fold increase of platelet phagocytosis by undifferentiated THP-1 cells and a ~5-fold increase by differentiated THP-1 cells (FIGS. 5B and 5c), consistent with mediation of platelet uptake by CR3. In contrast, the differentiation of THP-1 cells had no significant effect on the uptake of room temperature stored platelets (FIGS. 5A and 5c). To determine if GP1bα is the counter receptor for CR3-mediated phagocytosis on chilled human platelets, we used the snake venom metalloprotease mocarhagin, to remove the extracellular domain of GP1bα (Ward et al., 1996). Removal of human GP1bα from the surface of human platelets with mocarhagin reduced their phagocytosis after chilling by ~98% (FIG. 5C).

Exclusion of Other Mediators of Cold-Induced Platelet Clearance

Table 1 shows results of experiments that examined whether cooling affected the expression of platelet receptors other than GP1bα or their interaction with ligands. These experiments revealed no detectable effects on the expression of P-selectin, $\alpha_{IIb}\beta_3$-integrin density or on $\alpha_{IIb}\beta_3$ fibrinogen binding, a marker of $\alpha_{IIb}\beta_3$ activation. Chilling also did not increase phosphatidylserine (PS) exposure, an indicator of apoptosis, nor did it change platelet binding of IgG or IgM immunoglobulins.

TABLE 1

Effect of chilling on binding of various antibodies or ligands to platelet receptors.

| | Binding ratio 4° C.:22° C. | |
|---|---|---|
| Platelet receptor (ligand) | Human platelets | Murine platelets |
| P-Selectin (anti-CD62P mAb) | 1.01 ± 0.06 | 1.02 ± 0.03 |
| Platelet associated IgGs | 1.05 ± 0.14 | 1.06 ± 0.03 |
| Platelet associated IgMs | 0.93 ± 0.10 | 1.01 ± 0.02 |
| Phosphatidylserine (annexin V) | 0.95 ± 0.09 | 1.04 ± 0.02 |
| $\alpha_{IIb}\beta_3$ (anti-CD61 mAb) | 1.03 ± 0.05 | 1.04 ± 0.10 |
| $\alpha_{IIb}\beta_3$ (fibrinogen) | 1.05 ± 0.10 | 1.06 ± 0.06 |

The binding of fluorescently labeled antibodies or ligands against various receptors on chilled-rewarmed or room temperature human and murine platelets was measured by flow cytometry. The data are expressed as the ratio between the mean fluorophore bound to the surface of chilled versus room temperature platelets (mean±SD, n=3-4).

Circulating Chilled Platelets have Hemostatic Function in CR3-Deficient Mice.

Figure 6E:
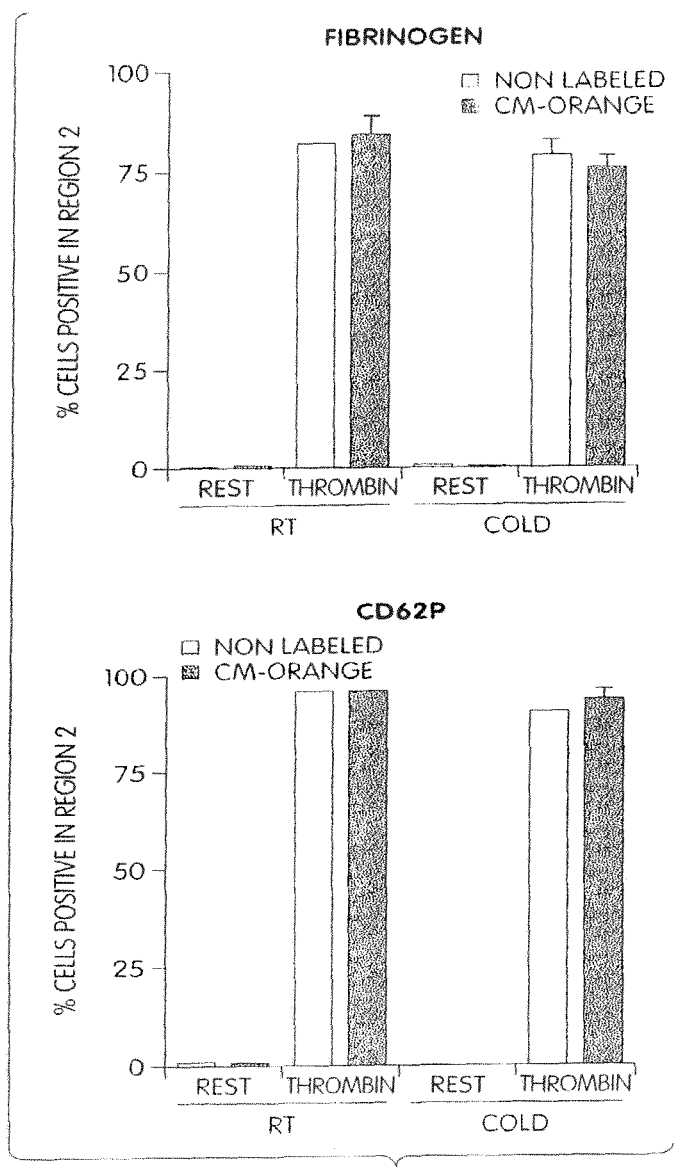

Despite their rapid clearance in wild type mice, CM-Orange or CMFDA labeled chilled platelets were functional 24 h after infusion into CR3-deficient mice, as determined by three independent methods. First, chilled platelets incorporate into platelet aggregates in shed blood emerging from a standardized tail vein bleeding wound (FIG. 6). CMFDA-positive room temperature platelets transfused into wild type mice (FIG. 6b) and CNIFDA-positive chilled platelets transfused into CR3-deficient mice (FIG. 6d) formed aggregates in shed blood to the same extent as CMFDA-negative platelets of the recipient mouse. Second, as determined by platelet surface exposure of the fibrinogen-binding site on $\alpha_{IIb}\beta_3$ 24 hours after transfusion of CM-Orange-labeled chilled and rewarmed platelets into CR3 deficient mice following ex vivo stimulation by thrombin. Third, CM-Orange platelets chilled and rewarmed were fully capable of upregulation of P-selectin in response to thrombin activation (FIG. 6e).

Discussion

Cold-Induced Platelet Shape Change Alone does not Lead to Platelet Clearance In Vivo Cooling rapidly induces extensive platelet shape changes mediated by intracellular cytoskeletal rearrangements (Hoffmeister et al., 2001; White and Krivit, 1967; Winokur and Hartwig, 1995). These alterations are partially but not completely reversible by rewarming, and rewarmed platelets are more spherical than discoid. The idea that preservation of platelet discoid shape is a major requirement for platelet survival has been a dogma, despite evidence that transfused murine and baboon platelets activated ex vivo by thrombin circulate normally with extensive shape changes (Berger et al., 1998; Michelson et al, 1996). Here we have shown that chilling leads to specific changes in the platelet surface that mediate their removal independently of shape change, and that the shape change per se does not lead to rapid platelet clearance. Chilled and rewarmed platelets, preserved as discs with pharmacological agents, clear with the same speed as untreated chilled platelets, and misshapen chilled and rewarmed platelets circulate like room temperature maintained platelets in CR3-deficient mice. The small size of platelets may allow them to remain in the circulation, escaping entrapment despite these extensive shape deformities.

Receptors Mediating Clearance of Chilled Platelets: CR3 and GP1bα

The normal platelet life span in humans is approximately 7 days (Aas, 1958; Ware et 2000). The incorporation of platelets into small blood clots engendered by continuous mechanical stresses undoubtedly contributes to platelet clearance, because massive clotting reactions, such as occur during disseminated intravascular coagulation, cause thrombocytopenia (Seligsohn, 1995). The fate of platelets in such clotting reactions differs from that of infused ex vivo-activated platelets such as in the experiments of Michelson et al (Michelson et al., 1996) and Berger et al (Berger et al., 1998), because in vivo platelet stimulation occurs on injured vessel walls, and the activated platelets rapidly sequester at these sites.

Isoantibodies and autoantibodies accelerate the phagocytic removal of platelets by Fc-receptor-bearing macrophages in individuals sensitized by immunologically incompatible platelets or in patients with autoimmune thrombocytopenia, but otherwise little information exists regarding mechanisms of platelet clearance. We showed, however, that the quantities of IgG or IgM bound to chilled or room-temperature human platelets are identical, implying that binding of platelet-associated antibodies to Fc-receptors does not mediate the clearance of cooled platelets. We also demonstrated that chilling of platelets does not induce detectable phosphatidylserine (PS) exposure on the platelet surface in vitro militating against PS exposure and the involvement of scavenger receptors in the clearance of chilled platelets.

Although many publications have referred to effects of cold on platelets as "activation", aside from cytoskeletally-mediated shape changes, chilled platelets do not resemble platelets activated by stimuli such as thrombin or ADP. Normal activation markedly increases surface P-selectin expression, a consequence of secretion from intracellular granules (Berman et al., 1986). Chilling of platelets does not lead to up-regulation of P-selectin (Table 1), but the clearance of chilled platelets isolated from wild-type or P-selectin-deficient mice is equally rapid (Berger et al., 1998). Activation also increases the amount of $\alpha_{IIb}\beta_3$-integrin and its avidity for fibrinogen (Shattil, 1999), but cooling does not have these effects (Table 1). The normal survival of thrombin-activated platelets is consistent with our findings.

We have shown that CR3 on liver macrophages is primarily responsible for the recognition and clearance of cooled platelets. The predominant role of CR3 bearing macrophages in the liver in clearance of chilled platelets despite abundant CR3-expressing macrophages in the spleen is consistent with the principally hepatic clearance of IgM-coated erythrocytes (Yan et al., 2000) and may reflect blood filtration properties of the liver that favor binding and ingestion by macrophage CR3. The extracellular domain of GP1bα binds avidly to CR3, and under shear stress in vitro supports the rolling and firm adhesion of THP-1 cells (Simon et al., 2000). Cleavage of the extracellular domain of murine GP1bα results in normal survival of chilled platelets transfused into mice. GP1bα depletion of human chilled platelets greatly reduces phagocytosis of the treated platelets by macrophage-like cells in vitro. We propose, therefore, that GP1bα is the co-receptor for liver macrophage CR3 on chilled platelets leading to platelet clearance by phagocytosis.

The normal clearance of cold platelets lacking the N-terminal portion of GP1bα rules out the many other CR3-binding partners, including molecules expressed on platelet surfaces as candidates for mediating chilled platelet clearance. These ligand candidates include ICAM-2, fibrinogen bound to the platelet integrin $\alpha_{IIb}\beta_3$, iC3b, P-selectin, glucosaminoglycans, and high molecular weight kininogen. We excluded deposition of the opsonic C3b fragment iC3b as a mechanism for chilled platelet clearance using mice deficient in complement factor 3, and the expression level of $\alpha_{IIb}\beta_3$ and fibrinogen binding are also unchanged after chilling of platelets.

Binding to Activated vWf and Cold-Induced Binding to CR3 Appear to be Separate Functions of GP1bα.

GP1bα on the surface of the resting discoid platelet exists in linear arrays (FIG. 5) in a complex with GP1bα, GP1X and V, attached to the submembrane actin cytoskeleton by filamin-A and Filamin B (Stossel et al., 2001). Its role in hemostasis is to bind the activated form of vWf at sites of vascular injury. GP1bα, binding to activated vWf is constitutive and requires no active contribution from the platelet, since activated vWf binds equally well to GP1bα on resting or on stimulated platelets. Stimulation of platelets in suspension by thrombin and other agonists causes GP1bα to redistribute in part from the platelet surface into an internal membrane network, the open canalicular system, but does not lead to platelet clearance in vivo (Berger et al., 1998; Michelson et al., 1996) or to phagocytosis in vitro (unpublished observations). Cooling of platelets however, causes GP1bα clustering rather than internalization. This clustering is independent of barbed end actin assembly, because it occurs in the presence of cytochalasin B.

Despite cold's promoting recognition of platelet GP1bα by CR3, it has no effect on interaction between GP1bα and activated vWf in vitro, and chilled platelets transfused into vWf-deficient mice disappear as rapidly as in wild-type mice. The separability of GP1bα's interaction with vWf and CR3 suggests that selective modification of GP1bα. might inhibit cold-induced platelet clearance without impairment of GP1bα's hemostatically important reactivity with vWf. Since all tests of platelet function of cooled platelets in vitro and after infusion into CR3-deficient mice yielded normal results, suitably modified platelets would predictably be hemostatically effective.

Physiological Importance of Cold-Induced Platelet Clearance.

Although gross platelet shape changes become obvious only at temperatures below 15° C., accurate biochemical analyses show that cytoskeletal alterations and increased responsiveness to thrombin are detectable as the temperature falls below 37° C. (Faraday and Rosenfeld, 1998; Hoffmeister et al., 2001; Tablin et al., 1996). We refer to those changes as "priming" because of the many functional differences that remain between cold-exposed and thrombin- or ADP-stimulated platelets. Since platelet activation is potentially lethal in coronary and cerebral blood vessels subjected to core body temperatures, we have proposed that platelets are thermosensors, designed to be relatively inactive at the core body temperature of the central circulation but to become primed for activation at the lower temperatures of external body surfaces, sites most susceptible to bleeding throughout evolutionary history (Hoffmeister et al., 2001). The findings reported here suggest that irreversible changes in GP1bα are the reason for the clearance of cooled platelets. Rather than allowing chilled platelets to circulate, the organism clears low temperature-primed platelets by phagocytosis.

Figure 7:
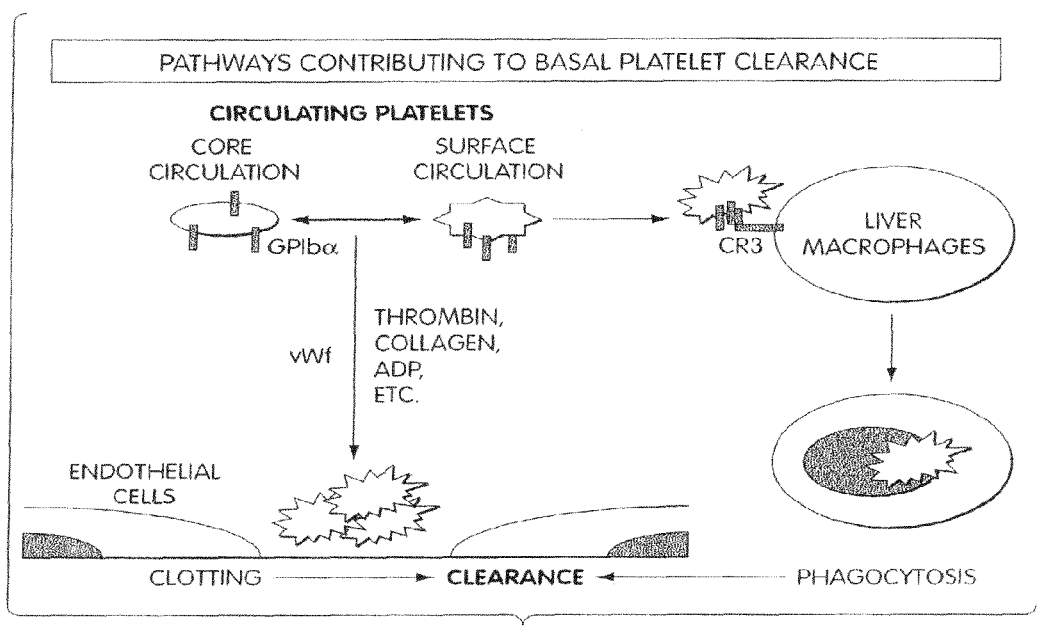
FIG. 7 is a schematic depicting two platelet clearance pathways. Platelets traverse central and peripheral circulations, undergoing reversible priming at lower temperatures at the body surface. Repeated priming leads to irreversible GP1b-TX-V (vWfR) receptor complex reconfiguration and clearance by complement receptor type 3 (CR3) bearing hepatic macrophages. Platelets are also cleared after they participate in microvascular coagulation.

A system involving at least two clearance pathways, one for removal of locally activated platelets and another for taking out excessively primed platelets (FIG. 7), can possibly explain why chilled platelets circulate and function normally in CR3-deficient mice and have a slightly prolonged circulation following removal of GP1bα. We propose that some primed platelets enter microvascular clots on a stochastic basis. Others are susceptible to repeated exposure to body surface temperature, and this repetitive priming eventually renders these platelets recognizable by CR3-bearing liver macrophages. Platelets primed by chilling are capable of normal hemostatic function in CR3-deficient mice, and coagulation contributes to their clearance. However, the slightly shorter survival time of autologous platelets in CR3-deficient mice examined is probably not ascribable to increased clearance of normally primed platelets in microvascular clots, because the clearance rate of refrigerated platelets was indistinguishable from that of platelets kept at room temperature.

REFERENCES FOR BACKGROUND OF THE INVENTION AND EXAMPLE 1

Aas, K. A. Gardener, F. H. (1958). Survival of blood platelets with chromium[51]. J. Clin. Invest. 37, 1257-1268.

Baker, G., Sullam, P. and Levin, J. (1997). A simple, fluorescent method to internally label platelets suitable for physiological measurements. Am. J. Hem. 56, 17-25.

Becker, G., Tuccelli, M., Kunicki, T., Chalos, M. and Aster, R. (1973). Studies of platelet concentrates stored at 22° C. and 4° C. Transfusion. 13, 61-68.

Berger, G., Hartwell, D. and Wagner, D. (1998). P-selectin and platelet clearance. Blood. 92, 4446-4452.

Bergmeier, W., Bouvard, D., Eble, J., Mokhatari-Nejad, R., Schulte, V., Zirngibl, H., Brakebusch, C., Fdssler, R. and Nieswandt, R. (2001). Rhodocytin (aggretin) activates platelets lacking αIIbβ1 integrin, glycoprotein VI, and the ligand-binding domain of glycoprotein Ibα. 2001. 276, 25121-25126.

Bergmeier, W., Rackebrandt, K., Schroder, W., Zirngibl, H. and Nieswandt, B. (2000). Structural and functional characterization of the mouse von Willebrand factor receptor GP1b-IX with novel monoclonal antibodies. Blood. 95, 886-983.

Berman, C., Yeo, E., Wencel-Drake, J., Furie, B., Ginsberg, M. and Furie B. (1986). A platelet alpha granule membrane protein that is associated with the plasma membrane after activation. Characterization and subcellular localization of platelet activation-dependent granule-external membrane protein. J Clin Invest. 78, 130-137.

Bioulac-Sage, P., Kuiper, J., Van Berkel, T. J. C. and Balabaud, C. (1996). Lymphocyte and macrophage populations in the liver. Hepatogastroenterology. 43, 4-14.

Brown, S., Clarke, 14, Magowan, L. and Sanderson, H. (2000). Constitutive death of platelets leading to scavenger receptor-mediated phagocytosis. A caspase independent program. J. Biol. Chem. 275, 5987-5995.

Chernoff, A. and Snyder, In. (1992). The cellular and molecular basis of the platelet storage lesion: A symposium summary. Transfusion. 32, 386-390.

Coxon, A., Rieu, P., Barkalow, F. J., Askari, S., Sharpe, A. H., Von Andrian, U. H., Amout, M. A. and Mayadas, T. N. (1996). A novel role for the β2 integrin CD11b/CD18 in neutrophil apoptosis: a homeostatic mechanism in inflammation. Immunity. 5, 653-666.

Denis, C., Methia, N., Frenette, P., Rayburn, H., Ullman-Cullere, M., Hynes, R. and Wagner, P. (1998). A mouse model of severe von Willebrand disease: defects in hemostasis and thrombosis. Proc Natl Acad Sci USA. 95, 9524-9529.

Engelfriet, C., Reesink, H. and Blajchman, M. (2000). Bacterial contamination of blood components. Vox Sang. 78, 59-67.

Faraday, N. and Rosenfeld, B. (1998). In vitro hypothermia enhances platelet GP1b-IIIa activation and P-selectin expression. Anesthesiology. 88, 1579-1585.

Hartwig, J., Bokoch, G., Carpenter, C., Janmey, P., Taylor, L., Toker, A. and Stossel, T. (1995). Thrombin receptor ligation and activated Rae uncap actin filament barbed ends through phosphoinositide synthesis in permeabilized human platelets. Cell. 82, 643-653.

Hartwig, J. and DeSisto, M. (1991). The cytoskeleton of the resting human blood platelet: Structure of the membrane skeleton and its attachment to actin filaments. J. Cell Biol. 112, 407-425.

Hartwig, J., Kung, S., Kovacsovics, T., Janmey, P., Cantley, L., Stossel, T. and Toker, A. (1996). D3 phosphoinositides and outside-in integrin signaling by GPHb/IIIa mediate platelet actin assembly and filopodial extension induced by phorbol 12-myristate 13-acetate. S. Biol. Chem. 271, 32986-32993.

Hoffmeister, K., Falet, H., Toker, A., Barkalow, K., Stossel, T. and Hartwig, J. (2001). Mechanisms of Cold-induced Platelet Actin Assembly. J Biol. Chem. 276, 24751-24759.

Jacobs, M., Palavecino, E. and Yomtovian, R. (2001). Don't bug me: the problem of bacterial contamination of blood components-challenges and solutions. Transfusion. 41, 1331-1334.

Janmey, P. and Stossel, T. (1989). Gelsolin-polyphosphoinositide interaction. Full expression of gelsolin-inhibiting function by polyphosphoinositides in vesicular form and inactivation by dilution, aggregation, or masking of the inositol head group. J. Biol. Chem. 264, 4825-4831.

Kotze, H. F., Lötter, M. G., Badenhorst, P. N. and Heyns, A. du P. (1985). Kinetics if In-111-Platelets in the Baboon: I. Isolation and labeling of a viable and representative platelet population. Thrombosis and Hemostasis. 53, 404-407.

Kovacsovics, T. and Hartwig, J. (1996). Thrombin-induced GP1b-IX centralization on the platelet surface requires actin assembly and myosin H activation. Blood. 87, 618-629.

MacPhee, P. J., Schmid, E. and Groom, A, (1992). Evidence for Kupffer cell migration along liver sinusoides, from high-resolution in vivo microscopy. Am. J. Physiol. 263, 17-23.

McCuskey, R. S. (1986). Microscopic methods for studying the microvasculature of internal organs. Physical Techniques in Biology and Medicine Microvascular Technology, edited by C. H. Barker, and W. F. Nastuk. Orlando, Fla.: Academic. 247-264.

Michelson, A., Barnard, M., Hechtman, H., MacGregor, H, Connolly, W, Loscalzo, J. and Valeri, C. (1996). In vivo tracking of platelets: circulating degranulated platelets rapidly lose surface P-selectin but continue to circulate and function. Proc. Natl. Acad. Sci., U.S.A. 93, 11877-11882.

Michelson, A., MacGregor, H., Barnard, M., Kestin, A., Rohrer, M. and Valeri, C. (1994). Reversible inhibition of human platelet activation by hyperthermia in vivo and in vitro. Thromb. haemost. 71, 633-640.

Morton, L., Hargreaves, P., Farndale, R., Young, R. and Barnes, M. (1995). Integrin-$\alpha_2\beta_1$-independent activation of platelets by simple collagen-like peptides: collagen tertiary (triple-helical) and quaternary (polymeric) structures are sufficient alone for $\alpha_2\beta_1$-independent platelet reactivity. Biochem J. 306, 337-344.

Schlichter, S, and Harker, L. (1976). Preparation and storage of platelet concentrates II. Storage variables influencing platelet viability and function. Brit J. Haemat. 34, 403-419.

Sehgsohn, U. (1995). Disseminated intravascular coagulation. Blood: Principles and Practice of Hematology. R. I. Handin, S. E. Lux, T. P. Stossel, ed. (Philadelphia, J.B. Lippincott Company) pp 1289-1317.

Shattil, S. (1999). Signaling through platelet integrin $\alpha_{IIb}\beta_3$: inside-out, outside-in, and sideways. Thromb Haemost. 82, 318-325.

Simon, D., Chen, Z., Xu, H., Li, C., Dong, J.-f., McIntire, L., Ballantyne, C., Zhang, L., Furman, M., Berndt, M. and Lopez, J. (2000). Platelet glycoprotein ibα is a counter-receptor for the leukocyte integrin Mac-1 (CD11b/CD18). J Exp Med. 192, 193-204.

Simon, D. I., Rao, N. K., Xu, Y., Wei, O., Majdic, E., Ronne, L., Kobzik, L. and Chapman, H. A. (1996). Mac-1 (CD11b/CD18) and the urokinase receptor (CD87) form a functional unit on monocytic cells. Blood. 88, 3185-94.

Stossel, T., Condeelis, J., Cooley, L., Hartwig, J., Noegel, A., Schleicher, M. and Shapiro, S. (2001). Filamins as integrators of cell mechanics and signalling. Nat Rev Mol Cell Biol. 2, 138-145.

Tablin, F., Oliver, A., Walker, N., Crowe, L. and Crowe, J. (1996). Membrane phase transition of intact human platelets: correlation with cold-induced activation. J. Cell. Phys. 168, 305-313.

Von Andrian, U. (2002). Immunology. T cell activation in six dimensions. Science. 296, 1815-1817.

Von Andrian, U. H. (1996). Intravital microscopy of the peripheral lymph node microcirculation in mice. Microcirculation. 3, 287-300.

Ward, C., Andrews, R., Smith, A. and Berndt, M. (1996). Mocarhagin, a novel cobra venom metalloproteinase, cleaves the platelet von Willebrandt factor receptor glycoprotein Ibα.

Identification of the sulfated tyrosine/anionic sequence Tyr-276-Glu-282 of glycoprotein Ibα as a binding site for von Willebrandt factor and a-thrombin. Biochemistry. 28, 8326-8336.

Ware, J., Russell, S, and Ruggeri, Z. (2000). Generation and rescue of a murine model of platelet dysfunction: the Bernard-Soulier syndrome. Proc Natl Acad Sci, USA. 97, 2803-2808.

Wessels, M. R., Butko, P., Ma, M., H. B., W, Lage, A. and Cauoll, M. C. (1995). Studies of group B streptococcal infection in mice deficient in complement component C3 or C4 demonstrate an essential role for complement in both innate and acquired immunity. Proc. Natl. Acad. Sci. USA. 92, 11490-11494.

White, J. and Krivit, W. (1967). An ultrastructural basis for the shape changes induced in platelets by chilling. Blood. 30, 625-635.

Vinokur, R. and Hartwig, J. (1995). Mechanism of shape change in chilled human platelets. Blood. 85, 1796-1804.

Yan, J., Vetvicka, V., Xia, Y., Hanikyrova, M., Mayadas, T. N., Ross, G. D. (2000). Critical role of Kupffer cell CR3 (CD11b/CD18) in the clearance of IgM-opsonized erythrocytes or soluble P-glucan. Immunopharmacology. 46, 39-54.

Yomtovian, R., Lazarus, H., Goodnough, L., Hirschler, N., Morrissey, A. and Jacobs, M. R (1993). A prospective microbiologic surveillance program to detect and prevent the transfusion of bacterially contaminated platelets. Transfusion. 33, 902-909.

Zucker, M. and Borrelli, J. (1954). Reversible alteration in platelet morphology produced by anticoagulants and by cold. Blood. 28, 524-534.

Example 2

Implication of the $\alpha_M\beta_2$ (CR3) Lectin Domain in Chilled Platelet Phagocytosis $\alpha_M\beta_2$ (CR3) has a cation-independent sugar-binding lectin site, located "C-T" to its I-domain (Thornton et al, *J. Immonol.* 156, 1235-1246, 1996), which binds to mannans, glucans and N-Acetyl-D-glucosamine (GlcNAc). Since CD16b/$\alpha_M\beta_2$ membrane complexes are disrupted by β-glucan, N-Acetyl-D-galactosamine (GalNAc), and methyl-α-mannoside, but not by other sugars, it is believed that this interaction occurs at the lectin site of the $\alpha_M\beta_2$ integrin (CR3) (Petty et al, *J. Leukoc. Biol.* 54, 492-494, 1993; Sehgal et al, *J. Immunol.* 150, 4571-4580, 1993).

The lectin site of $\alpha_M\beta_2$ integrin has a broad sugar specificity (Ross, R. *Critical Reviews in Immunology* 20, 197-222, 2000). Although sugar binding to lectins is usually of low affinity, clustering can cause a more robust interaction by increasing avidity. The clustering of GP1bα following cooling, as shown by electron microscopy, suggests such a mechanism. The most common hexosamines of animal cells are D-glucosamine and D-galactosamine, mostly occurring in structural carbohydrates as GlcNAc and GalNAc, suggesting that the $\alpha_M\beta_2$ integrin lectin domain might also bind to mammalian glycoproteins containing carbohydrates that are not covered by sialic acid. The soluble form of GP1bα, glycocalicin, has a carbohydrate content of 60% comprising N- as well as O-glycosidically linked carbohydrate chains (Tsuji et al, *J. Biol. Chem.* 258, 6335-6339, 1983). Glycocalicin contains 4 potential N-glycosylation sites (Lopez, et al, *Proc. Natl. Acad. Sci., USA* 84, 5615-5619, 1987). The 45 kDa region contains two sites that are N-glycosylated (Titani et al, *Proc Natl Acad Sci* 16, 5610-5614, 1987). In normal mammalian cells, four common core structures of O-glycan can be synthesized. All of them may be elongated, sialylated, fucosylated and sulfated to form functional carbohydrate structures. The N-linked carbohydrate chains of GP1bα are of the complex-type and di-, tri- and tetra-antennary structures (Tsuji et al, *J. Biol. Chem.* 258, 6335-6339, 1983). They are sialylated GalNAc type structures with an α(1-6)-linked fucose residue at the Asn-bound GlcNAc unit. There is a structural similarity of Asn-linked sugar chains with the Ser/Thr-linked: i.e., their position is of a common Gal-GlcNAc sequence. Results suggested that removal of sialic acid and galactose has no influence on the binding of vWf to glycocalicin, but partial removal of GlcNac resulted in the inhibition of vWf binding (Korrel et al, *FEBS Lett* 15, 321-326, 1988). A more recent study proposed that the carbohydrate patterns are involved in maintaining an appropriate functional conformation of the receptor, without participating directly in the binding of vWf (Moshfegh et al, *Biochem. Biophys. Res. Communic.* 249, 903-909, 1998).

A role of sugars in the interaction between chilled platelets and macrophages has the important consequence that covalent modification, removal or masking of oligosaccharide residues could prevent this interaction. We hypothesized that if such prevention does not impair normal platelet function, we may be able to modify platelets and enable cold platelet storage. Here, we show evidence that favor this hypothesis: 1) Saccharides inhibited phagocytosis of chilled platelets by macrophages in vitro, and the specific sugars that are effective implicated β-glucans as the relevant targets. Low concentrations of β-GlcNAc were surprisingly effective inhibitors, consistent with the idea that interference with a relatively small number of clustered sugars may be sufficient to inhibit phagocytosis. Addition of sugars at concentrations that maximally inhibited phagocytosis of chilled platelets has no effect on normal GP1bα function (vWf-binding); 2) A β-GlcNAc-specific lectin, but not other lectins, bound avidly to chilled platelets; 3) Removal of GP1bα or β-GlcNAc residues from platelet surfaces prevented this binding (since β-GlcNAc removal exposed mannose residues, it did not prevent phagocytosis by macrophages which have mannose receptors); 4) Blocking of exposed β-Glucans on chilled platelets by enzymatic addition of galactose markedly inhibited phagocytosis of chilled platelets by macrophages in vitro and extended the circulation times of chilled platelets in normal animals.

Effect of Monosaccharides on Phagocytosis of Chilled Platelets.

Figure 8A:
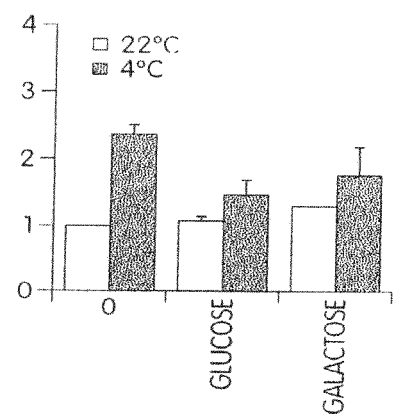
FIG. 8 shows the effect of monosaccharides on phagocytosis of chilled platelets.
Figure 8B:
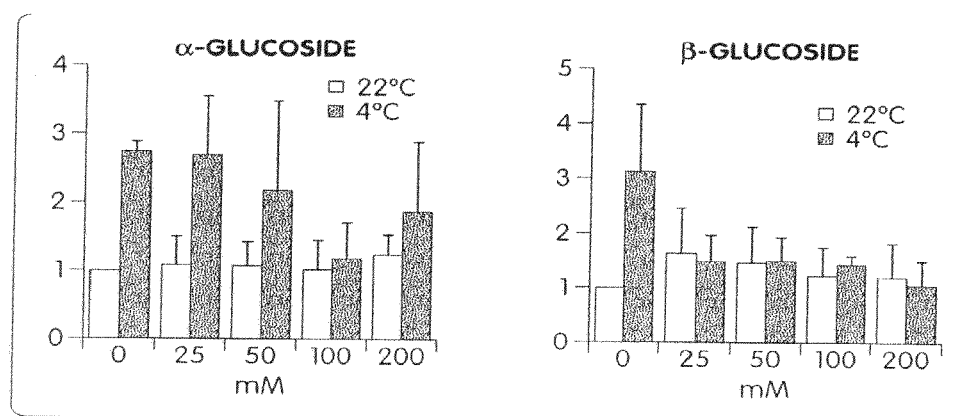
Figure 8C:
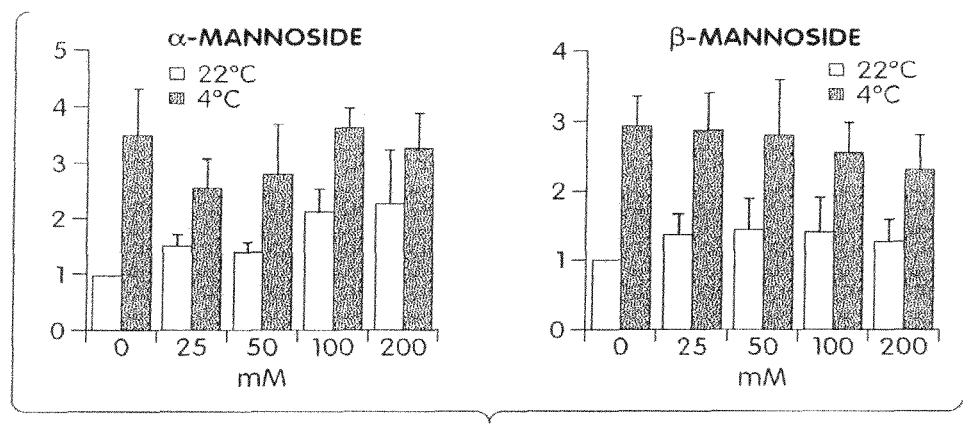
Figure 8D:
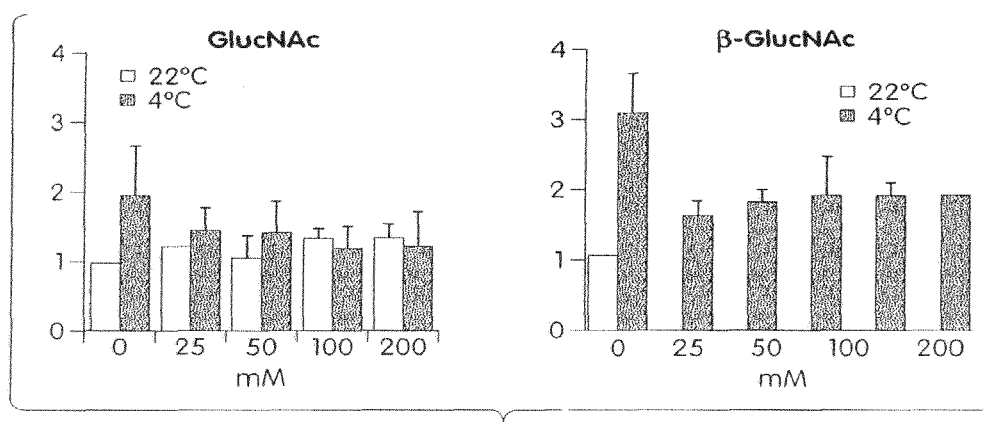

To analyze the effects of monosaccharides on platelet phagocytosis, phagocytes (differentiated monocytic cell line THP-1) were incubated in monosaccharide solutions at various concentrations, and the chilled or room temperature platelets were added. Values in the Figures are means±SD of 3-5 experiments comparing percentages of orange-positive monocytes containing ingested platelets incubated with RT or chilled platelets). While 100 mM D-glucose inhibited chilled platelet phagocytosis by 65.5% (P<0.01), 100 mM D-galactose did not significantly inhibit chilled platelet phagocytosis (n=3) (FIG. 8A). The D-glucose α-anomer (α-glucoside) did not have an inhibitory effect on chilled platelet phagocytosis, although 100 mM inhibited by 90.2% (FIG. 8B) In contrast, β-glucoside inhibited phagocytosis in a dose-dependent manner (FIG. 8B). Incubation of the phagocytes with 100 mM β-glucoside inhibited phagocytosis by 80% (p<0.05) and 200 mM by 97% (P<0.05), therefore we concluded that the β-anomer is preferred. D-mannose and its α- and β-anomers (methyl-α-D-mannopyranoside (FIG. 8C) and methyl-β-D-mannopyranoside (FIG. 8C) had no inhibitory effect on chilled or RT platelet phagocytosis. Incubation of phagocytes using 25 to 200 mM GlcNAc (N-acetyl-D-glucosamine) significantly inhibited chilled platelet phagocytosis. Incubation with 25 mM GlcNac was sufficient to inhibit the phagocytosis of chilled platelets by 86% (P<0.05) (FIG. 8D), whereas 10 µM of the β-anomer of GlcNAc inhibited the phagocytosis of chilled platelets by 80% (p<0.01) (FIG. 8D). None of the monosaccharides had an inhibitory effect on RT platelet phagocytosis. Table 2 summarizes the inhibitory effects of monosaccharides at the indicated concentrations on chilled platelet phagocytosis (**P<0.01, *P<0.05). None of the monosaccharides inhibited thrombin or ristocetin induced human platelet aggregation or induced α-granule secretion as measured by P-selectin exposure.

TABLE 2

Inhibitory effects of monosaccharides on chilled platelet phagocytosis

| Monosaccharides | % inhibition phagocytosis | mM |
|---|---|---|
| D-(+)-glucose | 65.5 | 100 |
| D-(+)-galactose | — | 100 |
| Methyl-α-D-glucopyranoside | 90.2* | 100 |
| Methyl-β-D-gludopyranoside | 80.2* | 100 |
|  | 97.1* | 200 |
| D-(+)-mannose | — | 100 |
| Methyl-α-D-mannopyranoside | — | 100 |
| Methyl-β-D-mannopyranoside | — | 100 |
| β-GlcNac | 80.9* | 0.01 |
| GlcNac | 86.3* | 25 |
|  | 83.9* | 100 |
|  | 83.1* | 200 |

Figure 9A:
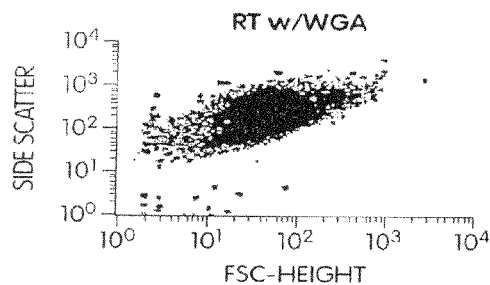
FIG. 9 shows the dot plots of binding of WGA lectin to room temperature platelets or chilled platelets.
Figure 9B:
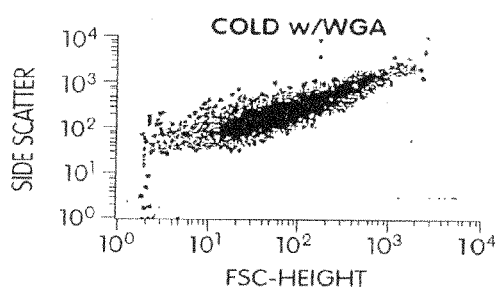
Figure 9C:
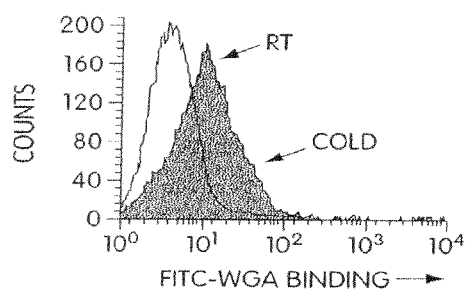
Figure 9D:
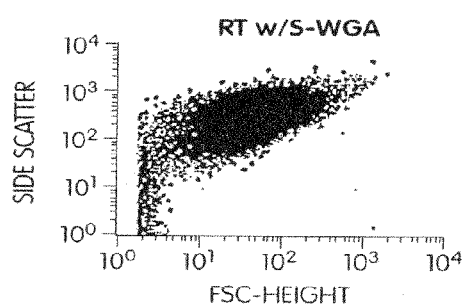
Figure 9E:
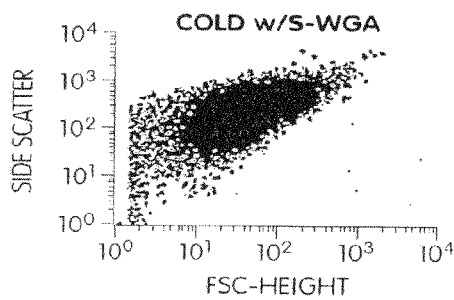
Figure 9F:
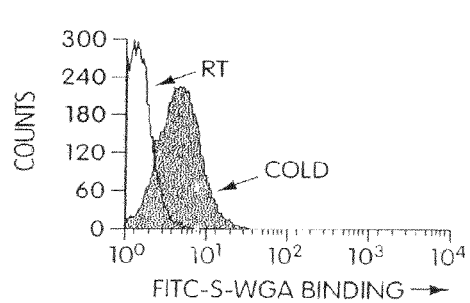

Binding of Various Lectins to Room Temperature Platelets or Chilled Platelets.

β-GlcNAc strongly inhibited chilled human platelet phagocytosis in vitro at µM concentrations, indicating that GlcNac is exposed after incubation of platelets in the cold. We then investigated whether wheat germ agglutinin (WGA), a lectin with specificity towards the terminal sugar (GlcNAc), binds more effectively to chilled platelets than to room temperature platelets. Washed, chilled or room temperature platelets were incubated with 2 µg/ml of FITC coupled WGA or FITC coupled succinyl-WGA for 30 min at room temperature and analyzed by flow cytometry. FIGS. 9A and 9B show the dot plots after incubation with FITC-WGA of room temperature (RT) or chilled (Cold) human platelets. WGA induces platelet aggregation and release of serotonin or ADP at concentrations between 25-50 µg/ml WGA (Greenberg and Jamieson, *Biochem. Biophys.* Acta 345, 231-242, 1974). Incubation with 2 µg/ml WGA induced no significant aggregation of RT-platelets (FIG. 9A, RT w/WGA), but incubation of chilled platelets with 2 µg/ml WGA induced massive aggregation (FIG. 9B, Cold/w WGA). FIG. 9C shows the analysis of FITC-WGA fluorescence binding to chilled or room temperature platelets. To verify that the increase of fluorescence binding is not aggregation related, we used succinyl-WGA (S-WGA), a dimeric derivate of the lectin that does not induce platelet aggregation (Rendu and Lebret, *Thromb Res* 36, 447-456, 1984). FIGS. 9D and 9E show that succinyl-WGA (S-WGA) did not induce aggregation of room temperature or chilled platelets, but resulted the same increase in WGA binding to chilled platelets versus room temperature platelets (FIG. 9F). The enhanced binding of S-WGA after chilling of platelets cannot be reversed by warming of chilled platelets to 37° C.

Exposed β-GlcNAc residues serve as substrate for a β1,4galactosyltransferase enzyme that catalyses the linkage Galβ-1GlcNAcβ1-R. In support of this prediction, masking of β-GlcNAc residues by enzymatic galactosylation inhibited S-WGA binding to cold platelets, phagocytosis of chilled platelets by THP-1 cells, and the rapid clearance of chilled platelets after transfusion into mice. The enzymatic galactosylation, achieved with bovine β1,4galactosyltransferase and its donor substrate UDP-Gal, decreased S-WGA binding to chilled human platelets to levels equivalent to room temperature platelets. Conversely, the binding of the galactose-specific RCA I lectin increased by ~2 fold after galactosylation. UDP-Glucose and UDP alone had no effect on S-WGA or RCA I binding to chilled or room temperature human platelets.

We found that the enzymatic galactosylation of human and mouse platelets is efficient without addition of exogenous β1,4galactosyltransferase. The addition alone of the donor substrate UDP-Gal reduces S-WGA binding and increases RCA I binding to chilled platelets, inhibits phagocytosis of chilled platelets by THP1 cells in vitro, and prolongs the circulation of chilled platelets in mice. An explanation for this unexpected finding is that platelets reportedly slowly release endogenous galactosyltransferase activity. A least one form of β1,4galactosyltransferases, β4Gal T1, is present in human plasma, on washed human platelets and in the supernatant fluids of washed platelets. Galactosyltransferases may associate specifically with the platelet surface. Alternatively, the activity may be plasma-derived and leak out of the platelet's open canalicular system. In either case, modification of platelet glycans responsible for cold-mediated platelet clearance is possible by simple addition of the sugar-nucleotide donor substrate, UDP-Gal.

Importantly, both chilled and non-chilled platelets show the same increase in RCA I binding after galactosylation, implying that β-GlcNAc residues are exposed on the platelet surface independent of temperature. However chilling is a requirement for recognition of β-GlcNAc residues by S-WGA and by the $\alpha_M\beta_2$ integrin. We have demonstrated that chilling of platelets induces an irreversible clustering of GP1b. Generally lectin binding is of low affinity and multivalent interactions with high density of carbohydrate ligands increases binding avidity. Possibly the local densities of exposed β-GlcNAc on the surface of non-chilled platelets are too low for recognition, but cold-induced clustering of GP1bα provides the necessary density for binding to S-WGA or the $\alpha_M\beta_2$ integrin lectin domain. We confirmed by S-WGA and RCA-I binding flow cytometry that UDP-Gal transfers galactose onto murine platelets in the presence or absence of added galactosyl transferase and documented that chilled, galactosylated murine platelets circulate and initially survive significantly better than untreated room temperature platelets.

Although the earliest recoveries (<2 min) did not differ between transfused RT, chilled and chilled, galactosylated platelets, galactosylation abolished an initial platelet loss of about 20% consistently observed with RT platelets.

Galactosylation of murine and human platelets did not impair their functionality in vitro as measured by aggregation and P-selectin exposure induced by collagen related peptide (CRP) or thrombin at concentrations ranging from maximally effective to three orders of magnitude lower. Importantly, the aggregation responses of unmodified and galactosylated chilled human platelets to a range of ristocetin concentrations, a test of the interaction between GP1b and activated VWF, were indistinguishable or slightly better. The attachment points for N-linked glycans on GP1bα are outside of the binding pocket for VWF. Moreover, mutant GP1bα molecules lacking N-linked glycans bind VFW tightly.

Figure 10:
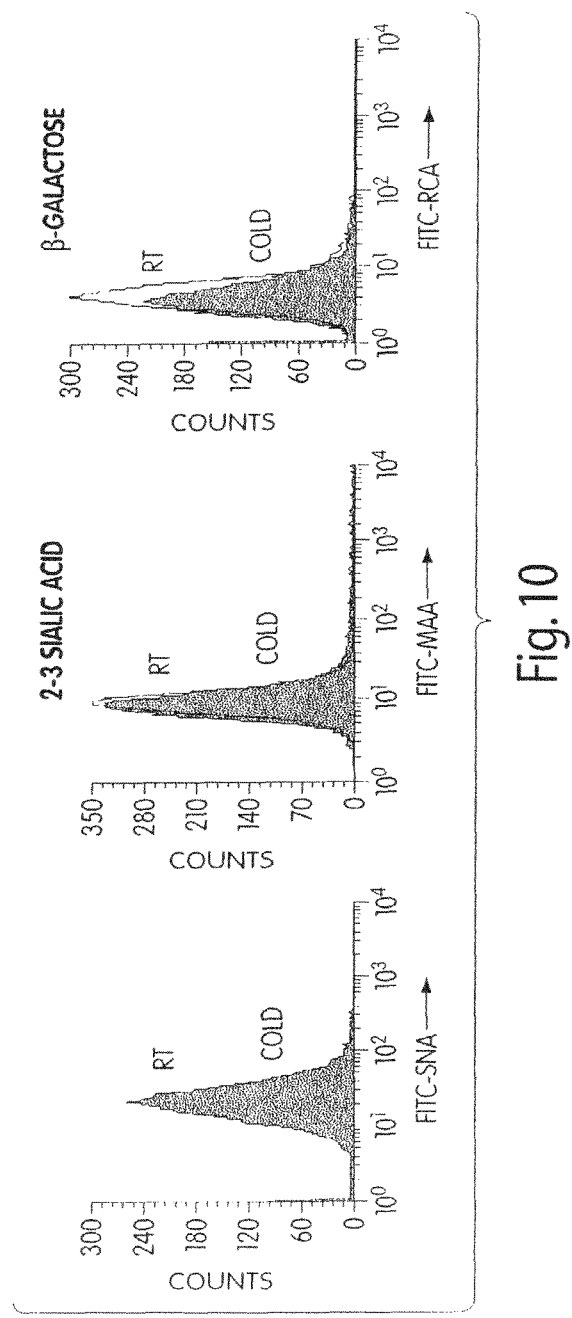
FIG. 10 shows the analysis of various FITC labeled lectins bound to room temperature or chilled platelets.

Using FITC labeled lectins with specificities towards β-galactose (*R. communis* lectin/RCA), 2-3 sialic acid (*Maackia anzurensis* lectin/MAA) or 2-6 sialic acid (*Sambucus Nigra* bark lectin/SNA), we could not detect increased binding after chilling of platelets by flow cytometry (FIG. 10), showing that exposure after chilling of platelets is restricted to GlcNAc.

We localized the exposed β-GlcNAc residues mediating $\alpha_M\beta_2$ lectin domain recognition of GP1bα N-glycans. The extracellular domain of GP1bα contains 60% of total platelet carbohydrate content in the form of N- and O-glycosidically linked carbohydrate chain. Accordingly, binding of peroxidase-labeled WGA to GP1bα is easily detectable in displays of total platelet proteins resolved by SDS-PAGE, demonstrating that GP1bα contains the bulk of the β-GlcNAc-residues on platelets, and binding of WGA to GP1bα is observable in GP1bα immunoprecipitates. UDP-Gal with or without added galactosyltransferase diminishes S-WGA binding to GP1bα, whereas RCA I binding to GP1bα increases. These findings indicate that galactosylation specifically covers exposed β-GlcNAc residues on GP1bα. Removal of the N-terminal 282 residues of GP1bα from human platelet surfaces using the snake venom protease mocarhagin, which inhibited phagocytosis of human platelets by THP-1 cells in vitro, reduces S-WGA binding to chilled platelets nearly equivalent to S-WGA room temperature binding levels. WGA binds predominantly to the N-terminus of GP1bα released by mocarhagin into ☐platelet supernatant fluids as a polypeptide band of 45 kDa recognizable by the monoclonal antibody SZ2 specific for that domain. The glycans of this domain are N-linked. A small portion of GP1bα remains intact after mocarhagin treatment, possibly because the open canalicular system of the platelet sequesters it. Peroxidase-conjugated WGA weakly recognizes the residual platelet associated GP1bα C-terminus after mocarhagin cleavage, identifiable with monoclonal antibody WM23.

The cold-induced increase in binding of human platelets to $\alpha_M\beta_2$ integrin and to S-WGA occurs rapidly (within minutes). The enhanced binding of S-WGA to chilled platelets remained stable for up to 12 days of refrigerated storage in autologous plasma. RCA I binding remained equivalent to room temperature levels under the same conditions. Galactosylation doubled the binding of RCA I lectin to platelets and reduced S-WGA binding to baseline RT levels. The increase in RCA I and decrease in S-WGA binding were identical whether galactosylation proceeded or followed storage of the platelets in autologous plasma for up to 12 days. These findings indicate that galactosylation of platelets to inhibit lectin binding is possible before or after refrigeration and that the glycan modification is stable during storage for up to 12 days. Platelets stored at room temperature rapidly lose responsiveness to aggregating agents; this loss does not occur with refrigeration. Accordingly, refrigerated platelets with or without galactosylation, before or after storage, retained aggregation responsiveness to thrombin for up to 12 days of cold storage.

Effects of β-Hexosaminidase (β-Hex) and Mocarhagin (MOC) on FITC-WGA Lectin Binding to Chilled Versus Room Temperature Stored Platelets.

Figure 11A:
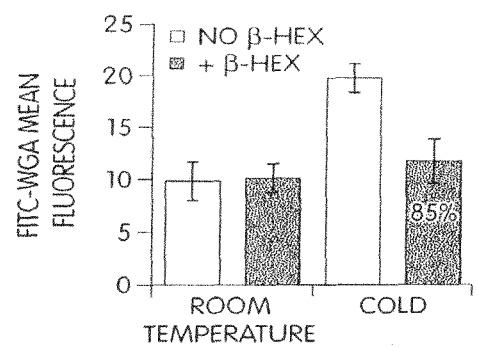
FIG. 11A shows the summary of FITC-WGA binding to the surface of room temperature or chilled platelets obtained by flow cytometry before and after β-hexosaminidase treatment.
Figure 11B:
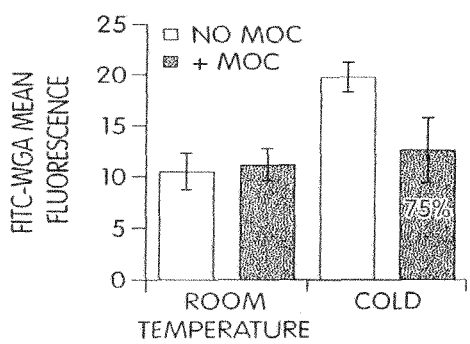
FIG. 11B shows that GP1bα removal from the platelet surface reduced FITC-WGA binding to chilled platelets.

The enzyme β-hexosaminidase catalyzes the hydrolysis of terminal β-D-N-acetylglucosamine (GlcNAc) and galactosamine (GalNAc) residues from oligosaccharides. To analyze whether removal of GlcNAc residues reduces the binding of WGA to the platelet surface, chilled and room temperature washed human platelets were treated with 100 U/ml β-Hex for 30 min at 37° C. FIG. 11A shows the summary of FITC-WGA binding to the surface of room temperature or chilled platelets obtained by flow cytometry before and after β-hexosaminidase treatment. FITC-WGA binding to chilled platelets was reduced by 85% after removal of GlcNac (n=3). We also checked whether, as expected, removal of GP1bα from the platelet surface leads to reduced WGA-binding after platelet chilling. GP1bα was removed from the platelet surface using the snake venom mocarhagin (MOC), as described previously (Ward et al, *Biochemistry* 28, 8326-8336, 1996). FIG. 11B shows that GP1bα removal from the platelet surface reduced FITC-WGA binding to chilled platelets by 75% and had little influence on WGA-binding to GP1bα-depleted room temperature platelets (n=3). These results indicate that WGA binds mostly to oligosaccharides on GP1bα after chilling of human platelets, and it is very tempting to speculate that the Mac-1 lectin site also recognizes these exposed sugars on GP1bα leading to phagocytosis.

Masking of Human Platelet GlcNAc Residues by Galactose-Transfer Greatly Reduces their Phagocytosis After Chilling In Vitro and Dramatically Increases their Survival in Mice.

Figure 12:
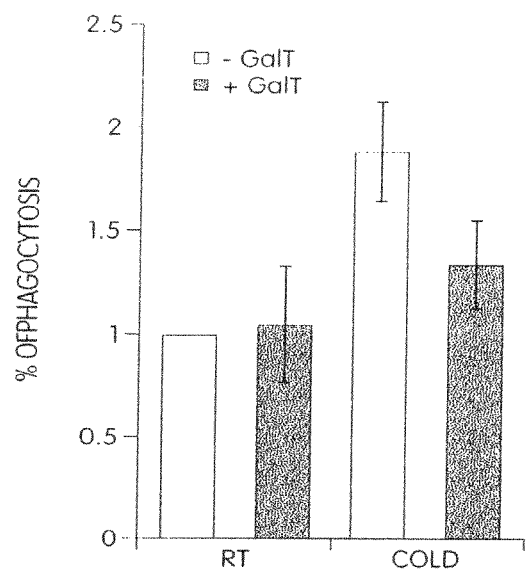
FIG. 12 shows that galactose transfer onto platelet oligosaccharides reduces chilled platelet (Cold) phagocytosis, but does not affect the phagocytosis of room temperature (RT) platelets.
Figure 13:
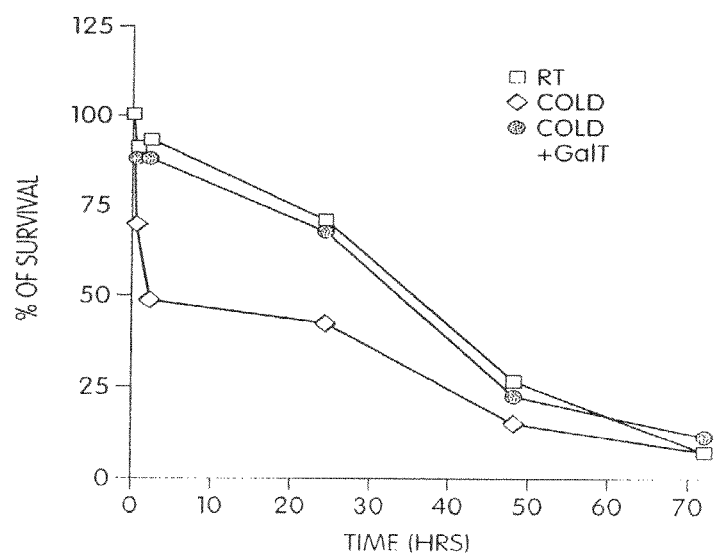
FIG. 13 shows the survival of chilled, galactosylated murine platelets relative to untreated platelets.

To achieve galactose transfer onto platelets, isolated human platelets were incubated with 200 μM UDP-galactose and 15 mU/ml galactose transferase for 30 min at 37° C., followed by chilling or maintenance at room temperature for 2 h. Galactosylation reduced FITC-WGA binding almost to resting room temperature levels. Platelets were fed to the monocytes and platelet phagocytosis was analyzed as described above. FIG. 12 shows that galactose transfer onto platelet oligosaccharides reduces greatly chilled platelet (Cold) phagocytosis, but does not affect the phagocytosis of room temperature (RT) platelets (n=3). These results show that in vitro the phagocytosis of chilled platelets can be reduced through coverage of exposed GlcNAc residues. We tested whether this approach could be extended to animals and used to increase the circulation time of chilled platelets. Murine platelets were isolated and stained with CMFDA. Using the same approach of galactose transfer described for human platelets above, wild type murine platelets were galactosylated and chilled, or not, for 2 hours. $10^8$ Platelets were transfused into wild type mice and their survival determined. FIG. 13 shows the survival of these chilled, galactosylated murine platelets relative to untreated platelets. Both platelets kept at room temperature (RT) and the galactosylated chilled platelets (Cold+GalT) had almost identical survival times, whereas chilled untreated platelets (Cold) were cleared rapidly as expected. We believe galactosylated chilled platelets will circulate in humans.

Figure 14A:
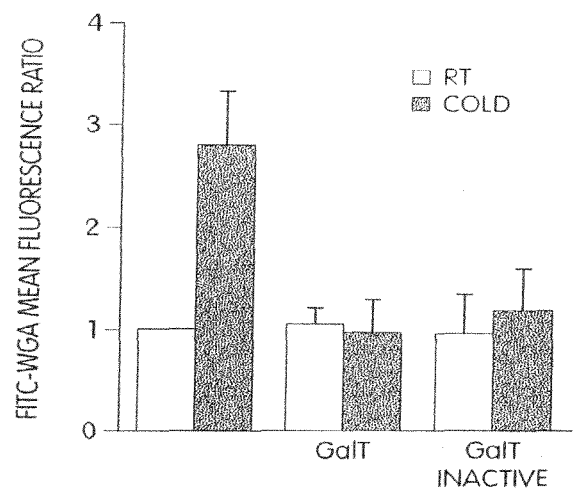
FIG. 14 shows that platelets containing galactose transferases on their surface transfer galactose without the addition of external transferases as judged by WGA binding (FIG. 14A) and in vitro phagocytosis results for human platelets (FIG. 14B).
FIG. 14C shows that of UDP-galactose with or without Galactose transferase (GalT) on survival of murine platelets. UDP-galactose with or without GalT was added to murine platelets before chilling for 30 min at 37° C. The platelets were chilled for 2 hours in an ice bath and then transfused ($10^8$ platelets/mouse) into mice and their survival determined.
Figure 14B:
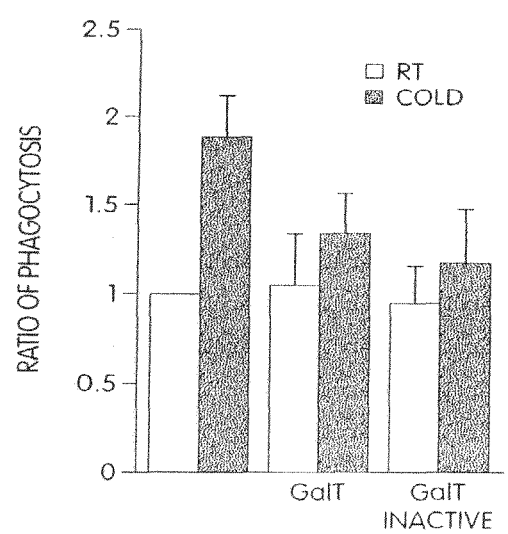
Figure 14C:
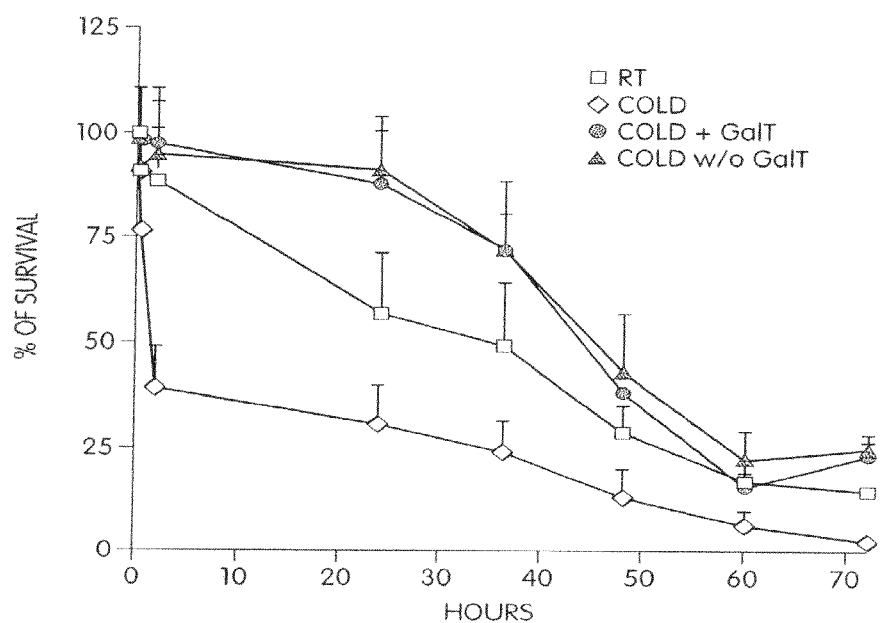

We noted that our control reaction, in which galactose transferase was heat-inactivated also resulted in glycan modification of platelets as occurred in the experimental reaction with active galactose transferase, as judged by WGA binding (FIG. 14A), in vitro phagocytosis results in human platelets (FIG. 14B), and survival of murine platelets (FIG. 14C). Therefore, we conclude that platelets contain galactose transferase activity on their surface, which is capable of directing glycan modification using only UDP-galactose without the addition of any exogenous galactose transferase. Thus, glycan modification of platelets can be achieved simply by incubation with UDP-galactose.

UDP-Galactose Incorporate into Human Platelets in a Time Dependent Matter.

Figure 15:
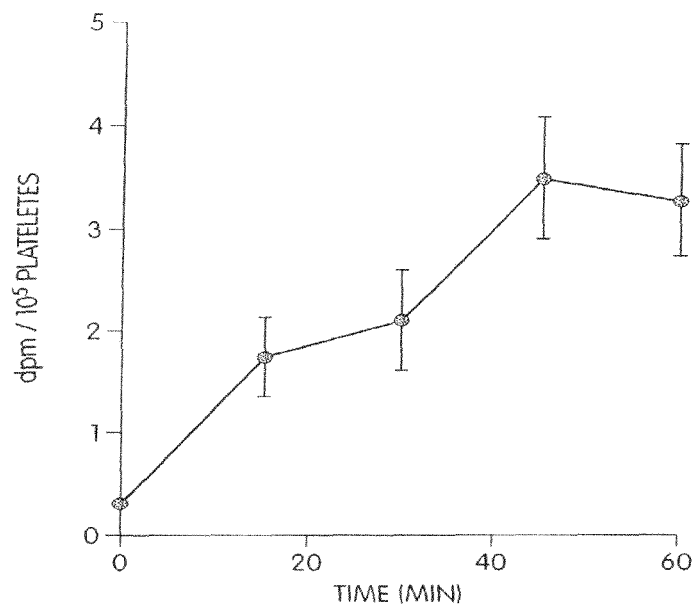
FIG. 15 shows the time course of $^{14}$C-labeled UDP-galactose incorporation into human platelets.

In another set of experiments we have shown that $^{14}$C-labeled UDP-galactose incorporates into human platelets in a time dependent manner in the presence or absence of the enzyme galactosyl transferase. FIG. 15 shows the time course of $^{14}$C-labeled UDP-galactose incorporation into washed human platelets. Human platelets were incubated with $^{14}$C-labeled UDP-galactose for different time intervals in the absence of galactosyl transferase. The platelets were then washed and the $^{14}$C radioactivity associated with platelets measured.

Example 3

Enzymatic Modification of Platelet β-Glycans Inhibit Phagocytosis of Cooled Platelets by Macrophages In Vitro and Accommodate Normal Circulation In Vivo Our preliminary experiments have demonstrated the enzymatic covering of GlcNAc residues on GP1bα using galactose-transfer (glycan modification) onto chilled human platelet surfaces greatly reduced their in vitro phagocytosis. One interpretation of these findings is that GP1bα structure is altered on the surface of chilled human and murine platelets. This causes the exposure or clustering of GlcNAc, which is recognized by the lectin binding domain of αMβ2 leading to platelet removal. β-GlcNAc exposure can be measured by WGA binding and possibly by binding of recombinant αMβ2 lectin domain peptides. Resting human platelets bind WGA, which increases greatly after chilling. We propose that galactose transfer (glycan modification) will prevent GP1bα's interaction with αMβ2-lectin but not with vWf. This modification (galactose transfer onto platelet surface) leads to normal survival of chilled platelets in WT mice as shown by our preliminary experiments.

Example 4

This example shows that the αMβ2 lectin site mimics WGA and sugar modifications prevent the engagement of the recombinant lectin site with chilled platelets. Dr. T. Springer (Corbi, et al., *J. Biol. Chem.* 263, 12403-12411, 1988) provided the human αM cDNA and several anti-αM antibodies. The smallest r-huαM construct exhibiting lectin activity that has been reported includes its C-T and a portion of its divalent cation binding region (residues 400-1098) (Xia et al, *J Immunol* 162, 7285-7293, 1999). The construct is 6×His-tagged for ease of purification. We first determined if the recombinant lectin domain can be used as a competitive inhibitor of chilled platelet ingestion in the phagocytic assay. Competition proved that the αM lectin site mediates binding to the platelet surface and initiates phagocytosis. As controls, a construct lacking the lectin-binding region of αM was used and the recombinant protein was denatured. Lectin binding domain functions as a specific inhibitor of chilled platelet ingestion. We made a αM construct that include GFP and express and labeled the αM-lectin binding site with FITC and used it to label the surface of chilled platelets by flow cytometry. Platelets were labeled with CMFDA. We found that chilled platelets bind more efficiently to the αM lectin side of αMβ2 integrin compared to room temperature platelets. The lectin side and whole αM-construct (Mac-1) was expressed in Sf9 insect cells.

The platelet sugar chains are modified to inhibit the platelet-oligosaccharide interaction with the r-huαM-lectin site.

The efficiency of sugar modifications is also monitored by inhibition of the binding of fluorescent-lectin domain binding to platelets by flow cytometry.

The recovery and circulation times of room temperature, chilled and chilled-modified platelets are compared to establish that galactose transfer onto chilled murine platelets results in longer circulating platelets. Room temperature, chilled and chilled-modified platelets are stained with CMFDA, and $10^8$ platelets transfused into wild type mice as described above. The mice are bled immediately (<2 min.), 30 min, 1 h, 2, 24, 48 and 72 hours after transfusion. The blood obtained is analyzed using flow cytometry. The percentage of fluorescent labeled platelets within the gated platelet population measured immediately after injection is set as 100%. The recovery of fluorescently labeled platelets obtained at the various time points is calculated accordingly.

Example 5

This example demonstrates that chilled, unmodified and chilled, galactosylated (modified) platelets have hemostatic function in vitro and in vivo. Chilled platelets are not "activated" in the sense of agonist-stimulated platelets. Patients undergoing surgery under hypothermic conditions may develop thrombocytopenia or show severe hemostatic postoperative impairments. It is believed that under these hypothermic conditions, platelets might lose their functionality. However, when patients undergo hypothermic surgery, the whole organism is exposed to hypothermia leading therefore to changes in multiple tissues. Adhesion of non-chilled platelets to hepatic sinusoidal endothelial cells is a major mechanism of cold preservation injury (Takeda, et al. *Transplantation* 27, 820-828, 1999). Therefore, it is likely that it is the interaction between cold hepatic endothelium and platelets, not platelet chilling per se, that leads to deleterious consequences under hypothermic conditions of surgery or transplantation of cold preserved organs (Upadhya et al, *Transplantation* 73, 1764-1770, 2002). Two approaches showed that chilled platelets have hemostatic function. In one approach, the circulation of chilled platelets in αMβ2-deficient mice facilitates studies of platelet function after cooling. In the other approach, the function of modified chilled and (presumably) circulating platelets was tested.

Human and murine unmodified and modified (galactosylated) chilled platelets were tested for functionality, including in vitro aggregation to agonists, P-selectin exposure and fibrinogen binding.

αMβ2 deficient or WT mice are transfused with murine chilled/RT platelets modified or not, and allowed to circulate for 30 min., 2 and 24 hours. We determine if chilled platelets contribute to clotting reactions caused by tail vein bleeding and if these platelets bind agents such as fibrinogen after activation. We also determine how chilled platelets, modified or not, contribute to clotting on ferric chloride injured and exteriorized mouse mesenteries, an in vivo thrombus-formation model that we developed. This method detects the number of platelets adherent to injured vessels and has documented impaired platelet vessel wall interactions of platelets lacking glycoprotein V or β3-integrin function (Ni et al., *Blood* 98, 368-373 2001; Andre, et al. *Nat Med* 8, 247-252, 2002). Last, we determine the storage parameters of the modified platelets.

In vitro platelet function is compared using aggregation with thrombin and ADP and botrocetin induced vWf-binding to murine platelets. Murine and human chilled platelets modified (galactosylated) or unmodified platelets are normalized to a platelet concentration of $0.3 \times 10^9/\text{mm}^3$, and aggregation induced using the various agonists according to standard protocols (Bergmeier, et al. 2001 276, 25121-25126, 2001). To study vWf-binding we activate murine vWf using botrocetin and analyze the binding of fluorescently labeled vWf to chilled platelets modified or not in PRP (Bergmeier, et al. 2001 276, 25121-25126, 2001). To evaluate whether degranulation of platelets occurs during modification, we also measure P-selectin exposure of chilled murine and human platelets modified or not using fluorescent labeled anti-P-selectin antibodies by flow cytometry (Michelson et al., *Proc. Natl. Acad. Sci., USA* 93, 11877-11882, 1996).

$10^9$ CMFDA-labeled platelets are transfused into mice, first verifying that these platelets are functional in vitro. We determine whether chilled platelets contribute to aggregation by transfusing chilled or room temperature CMFDA-labeled platelets into αMβ2 deficient mice. At 30 min., 2 hours and twenty-four hours after the infusion of platelets, a standard tail vein bleeding test is performed (Denis, et al. *Proc Natl Acad Sci USA* 95, 9524-9529, 1998). The emerging blood is fixed immediately in 1% formaldehyde and platelet aggregation is determined by whole blood flow cytometry. Platelet aggregates appear as bigger sized particles in the dot plot analysis. To verify that the transfused platelets do not aggregate in the normal circulation we also bleed the mice through the retroorbital eye plexus into an anticoagulant. Platelets do not form aggregates under these bleeding conditions. The emerging blood is fixed immediately and platelets are analyzed by flow cytometry in whole blood as described above. Platelets are identified through binding of a phycoerythrin-conjugated $\alpha_{IIb}\beta_3$ specific monoclonal antibody. The infused platelets in the blood sample are identified by their CMFDA-fluorescence. Non-infused platelets are identified by their lack of CMFDA fluorescence (Michelson, et al, *Proc. Natl. Acad. Sci., U.S.A.* 93, 11877-11882, 1996). The same set of tests is performed with CMFDA modified (galactosylated) chilled platelets transfusing these platelets into αMβ2 and WT. This experiment tests aggregation of chilled platelets modified or not in shed blood.

$10^9$ CM-orange labeled unmodified chilled or room temperature platelets are transfused into αMβ2 deficient mice to verify that these platelets are functional in vitro. At 30 min., 2 h and twenty-four hours after the infusion of CM-orange labeled platelets, PRP is isolated as described and analyzed by flow cytometry. P-selectin exposure is measured using an anti FITC-conjugated anti P-selectin antibody (Berger, et al, *Blood* 92, 4446-4452, 1998). Non-infused platelets are identified by their lack of CM-orange fluorescence. The infused platelets in the blood sample are identified by their CM-orange fluorescence. CM-orange and P-selectin positive platelets appear as double positive fluorescently (CM-orange/FITC) stained platelets. To verify that chilled platelets still expose P-selectin after thrombin activation, PRP is activated through the addition of thrombin (1 U/ml, 2 min at 37° C.) and P-selectin exposure is measured as described. To analyze the binding of fibrinogen to $\alpha_{IIb}\beta_3$, isolated platelets are activated through the addition of thrombin (1 U/ml, 2 min, 37° C.) and Oregon-green coupled fibrinogen (20 μg/ml) added for 20 min at 37° C. (Heilmann, et al, *Cytometry* 17, 287-293, 1994). The samples are analyzed immediately by flow cytometry. The infused platelets in the PRP sample are identified by their CM-orange fluorescence. CM-orange and Oregon-green positive platelets appear as double positive fluorescently stained (CM-orange/Oregon green) platelets. The same sets of experiments are performed with CM-orange labeled modified (galactosylated) chilled platelets transfused into αMβ2 deficient and WT mice.

Example 6

In Vivo Thrombosis Model

First, we show the delivery of RT and unmodified chilled platelets to injured endothelium of αMβ2 deficient mice using double fluorescently labeled platelets. The resting blood vessel is monitored for 4 min., then ferric chloride (30 μl of a 250-mM solution) (Sigma, St Louis, Mo.) is applied on top of the arteriole by superfusion, and video recording resumed for another 10 min. Centerline erythrocyte velocity (Vrbc) is measured before filming and 10 min after ferric chloride injury. The shear rate is calculated on the basis of Poiseuille's law for a Newtonian fluid (Denis, et al, *Proc Natl Acad Sci U S A* 95, 9524-9529, 1998). These experiments show if chilled platelets have normal hemostatic function. We repeat these experiments in WT mice comparing RT and galactosylated chilled platelets using two different, fluorescently labeled platelet populations injected into the same mouse and analyze the thrombus formation and incorporation of both platelet populations.

We then compare in vitro platelet functions and survival and in vivo hemostatic activity of chilled and modified chilled murine platelets stored for 1, 5, 7 and 14 days under refrigeration as described above. We compare the recovery and circulation times of these stored chilled and modified chilled platelets and prove that: 1) the modification through galactose transfer onto chilled murine platelets is stable after the long term refrigeration; and 2) that these platelets function normally. Survival experiments are performed as described above. We use WGA binding, to verify that GlcNAc residues remain covered by galactose after the longer storage time points. As an ultimate test that these modified, stored platelets are functionally intact and contribute to hemostasis, we transfuse them into total-body-irradiated mice (Hoyer, et al, *Oncology* 49, 166-172, 1992). To obtain the sufficient numbers of platelets, we inject mice with commercially available murine thrombopoietin for seven days to increase their platelet count (Lok, et al. *Nature* 369, 565-558, 1994). Isolated platelets are modified using the optimized galactose transfer protocol, stored under refrigeration, transfused, and tail vein bleeding times measured. Since unmodified chilled platelets do not persist in the circulation, a comparison of modified cooled platelets with room temperature stored platelets is not necessary at this point. The murine platelets are stored under refrigeration in standard test tubes. If a comparison with room temperature stored murine platelets is necessary we switch to primate platelets. Rather than engineer special down-scale, gas-permeable storage containers to accommodate mouse platelets, such comparisons are more appropriate for primates (including humans) for which room temperature storage bags have been designed.

Example 7

Galactosylation of Platelets in a Platelet Concentrate

Figure 16:
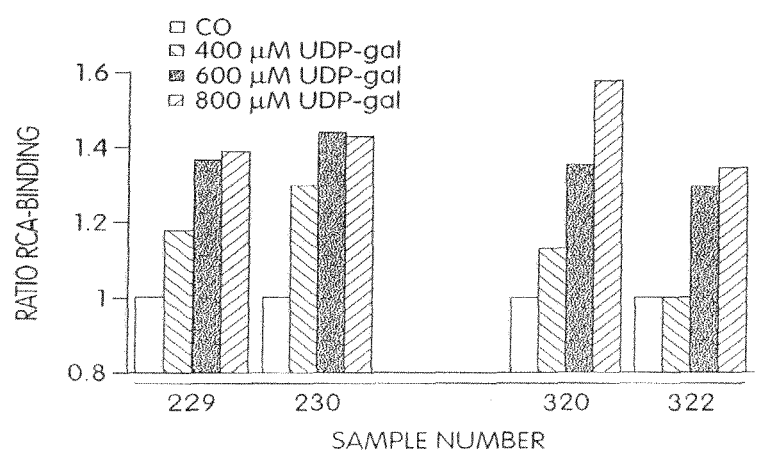
FIG. 16 shows galactosylation of platelets in four platelet concentrate samples at different concentrations of UDP-galactose.
Figure 17:
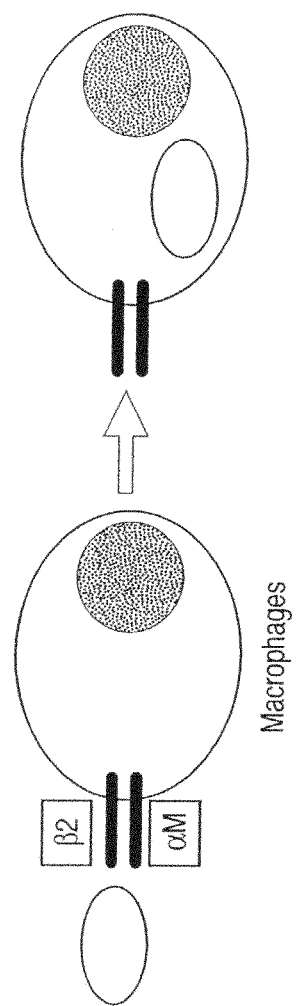
FIG. 17 shows the complement receptor mediates phagocytosis and clearance of chilled platelets.
Figure 18:
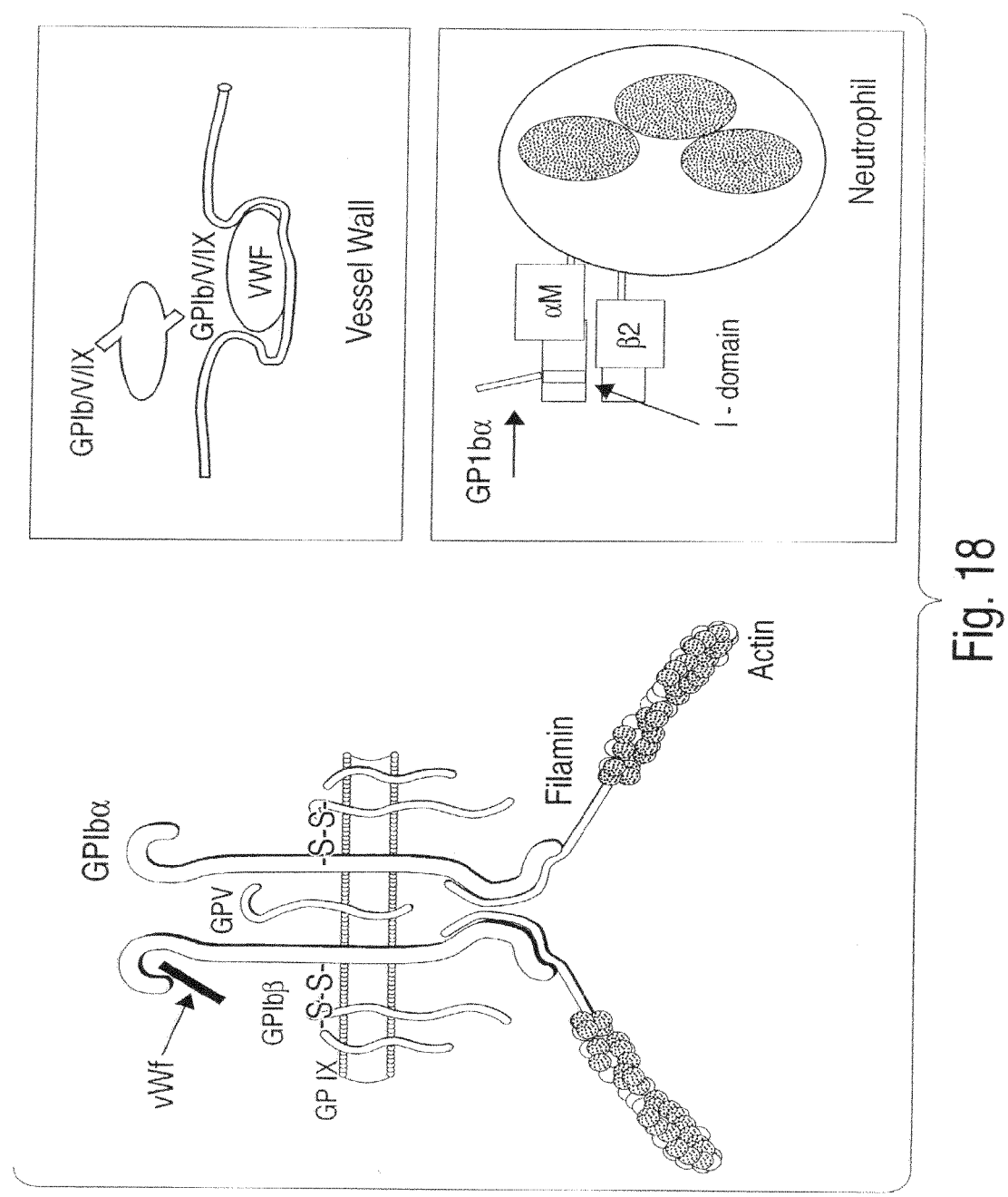
FIG. 18 shows the GP1bα subunit of platelet von Willebrand factor receptor binds the I-domain of αM of αM/β2 integrin.
Figure 19:
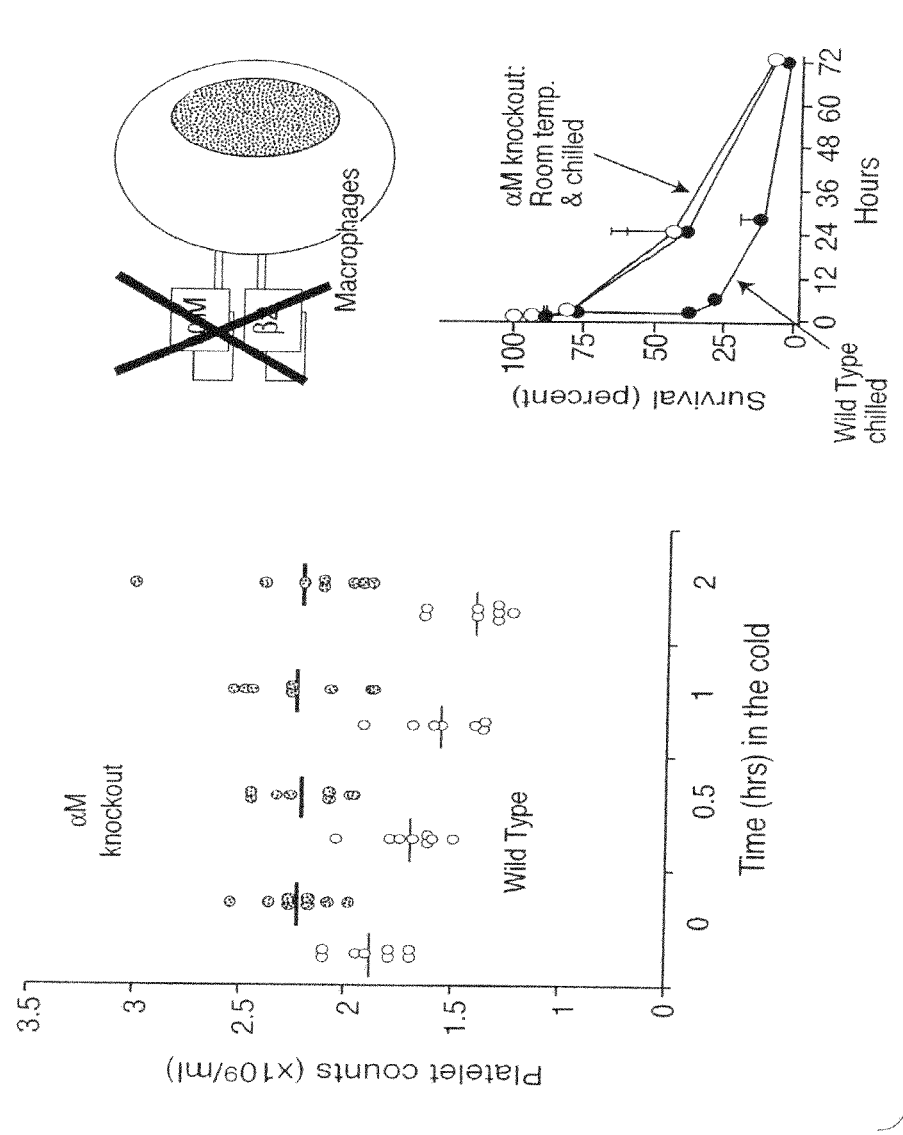
FIG. 19 shows that chilled platelets circulate and function normally in αM knockout mice.
Figure 20:
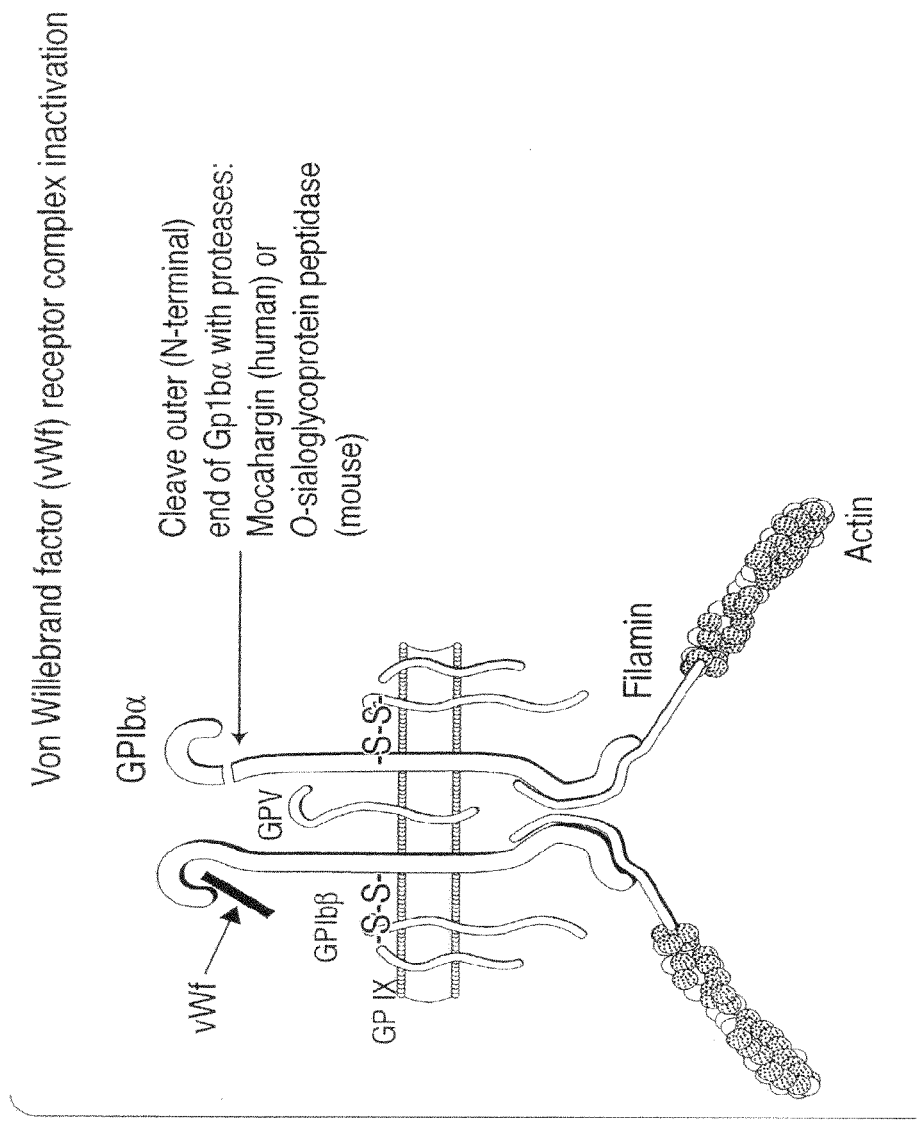
FIG. 20 illustrates vWf receptor inactivation.
Figure 21:
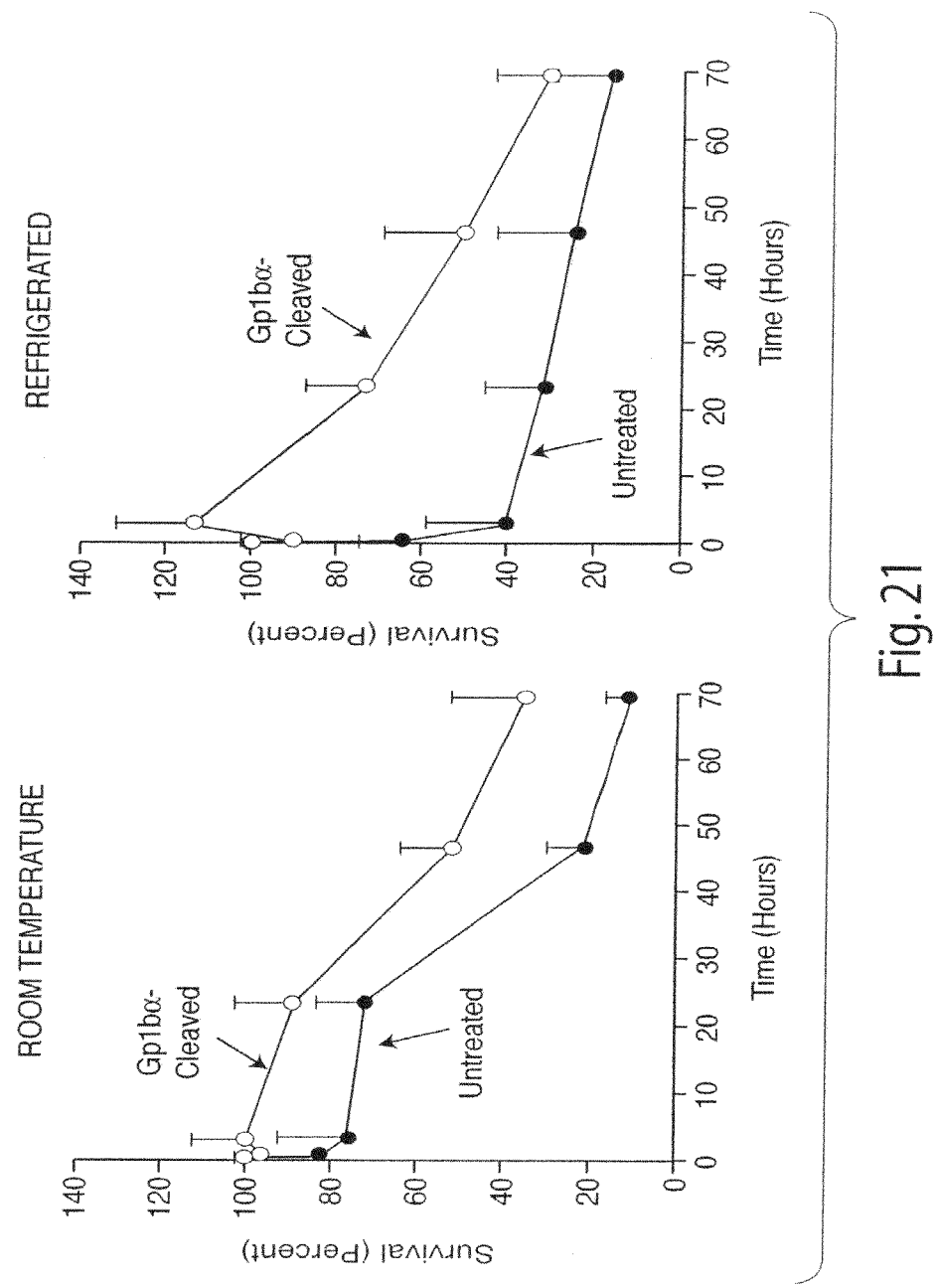
FIG. 21 shows that αM/β2 recognizes the outer tip of GP1bα and mediates clearance of chilled platelets, thus demonstrating that GP1bα has coagulant (vWf binding) and non-coagulant (clearance) functions.
Figure 22:
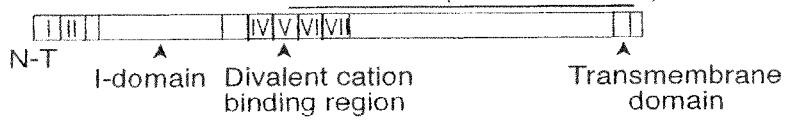
FIG. 22 illustrates the primary structure of αM (CD11b).
Figure 23:
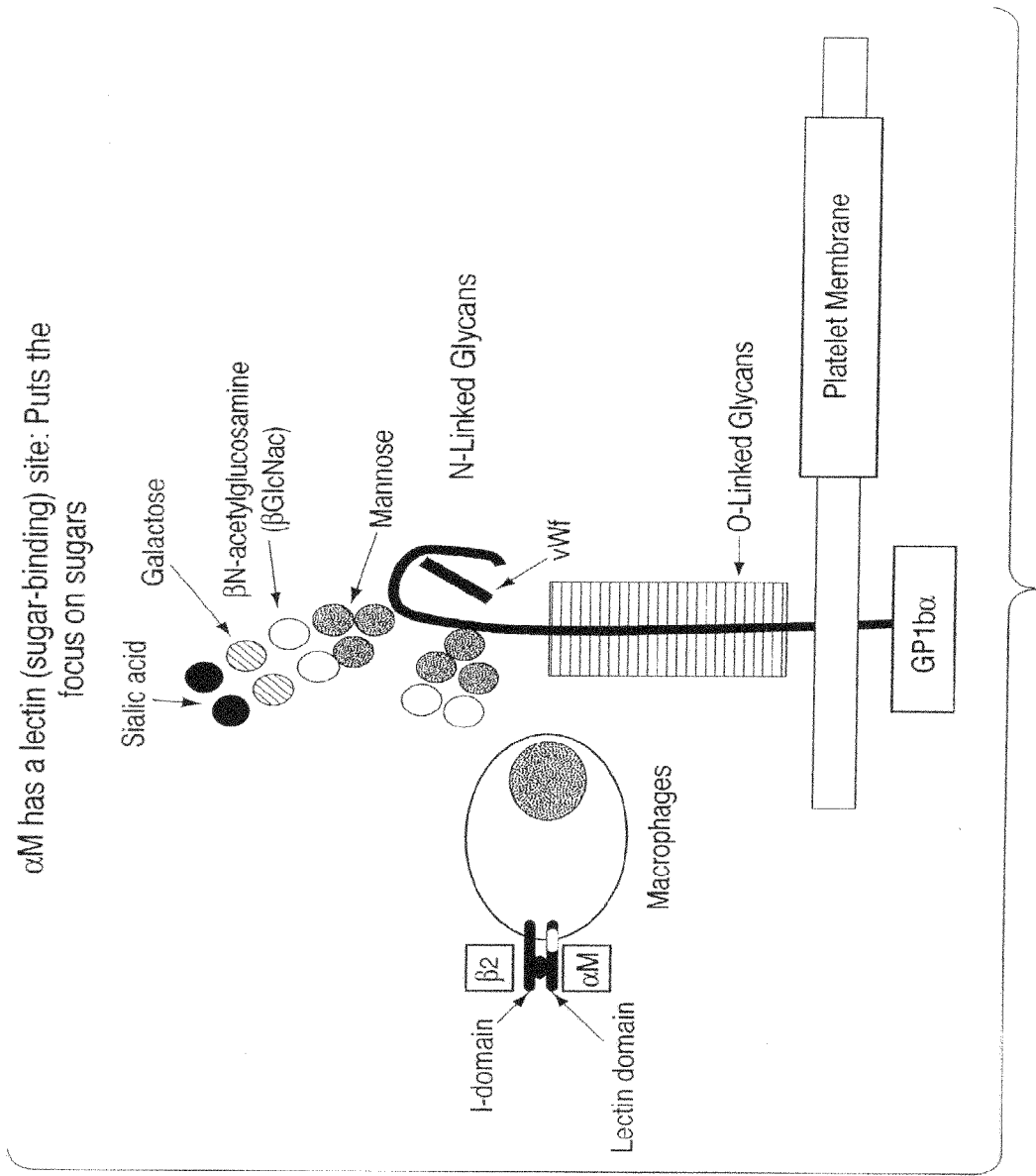
FIG. 23 shows that αM has a lectin affinity site.
Figure 24:
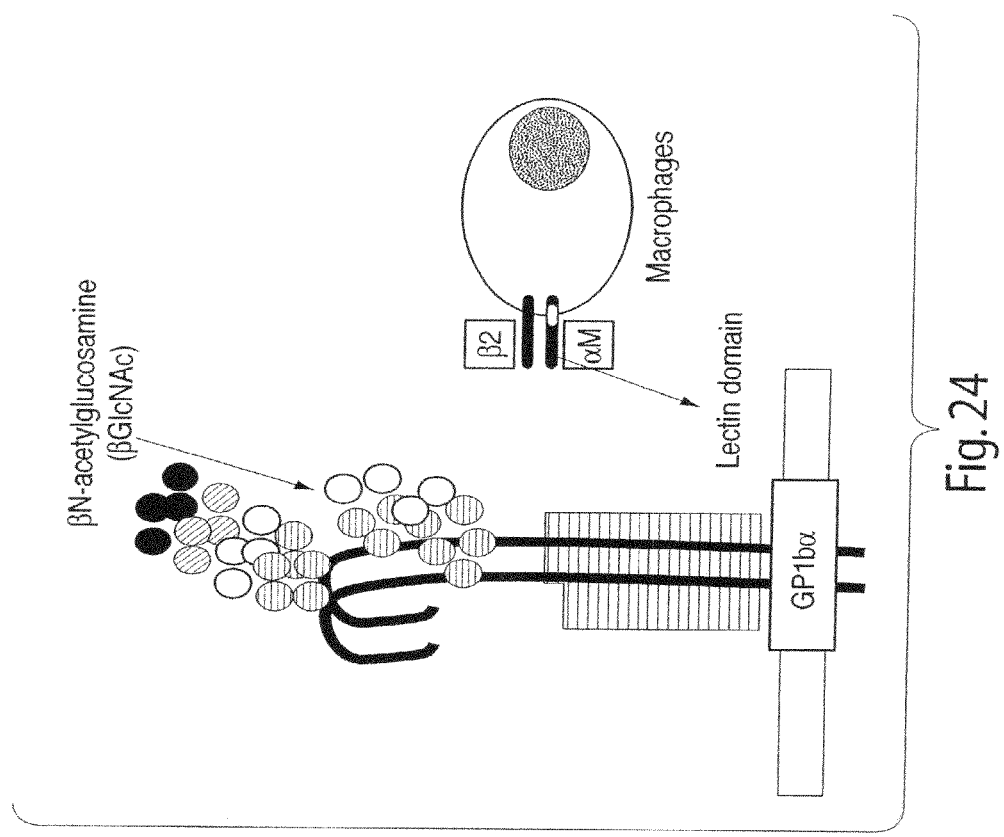
FIG. 24 shows that the lectin domain of macrophage αM/β2 receptors recognizes βGlcNAc residues on clustered GP1bα.
Figure 25:
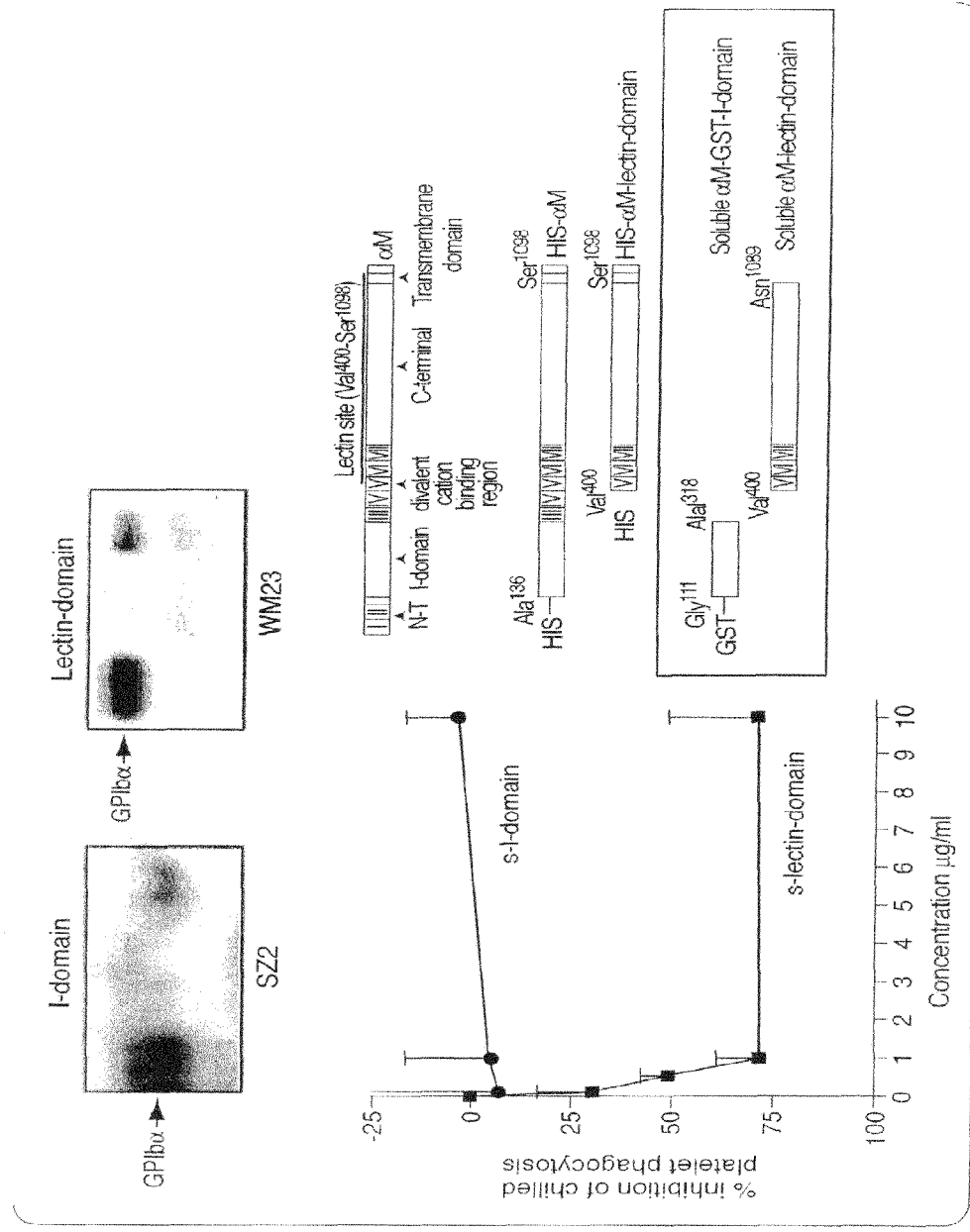
FIG. 25 shows that a soluble αM-lectin domain inhibits chilled human platelet phagocytosis by macrophages.
Figure 26:
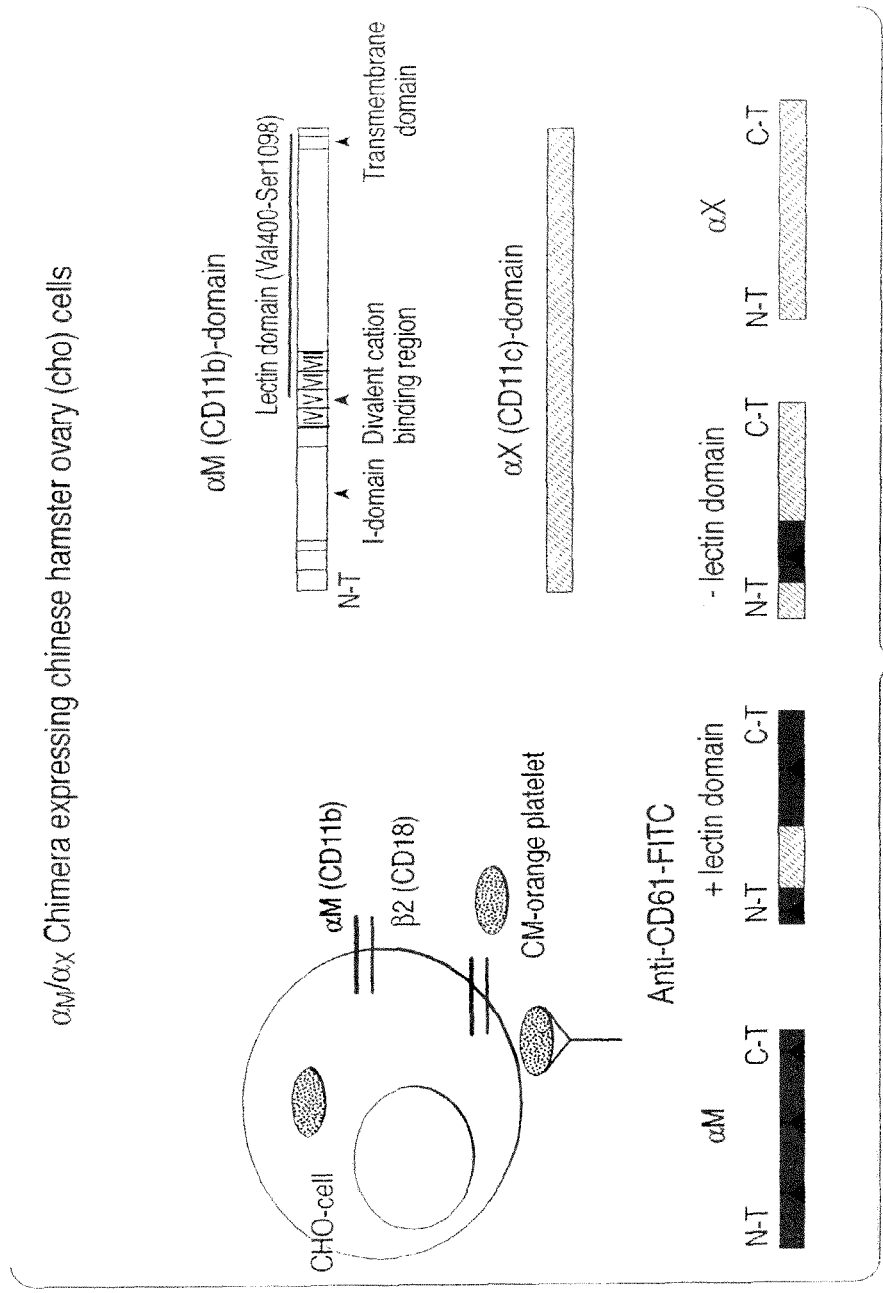
FIG. 26 shows the construction of CHO cells expressing αMαX chimeric proteins.
Figure 27:
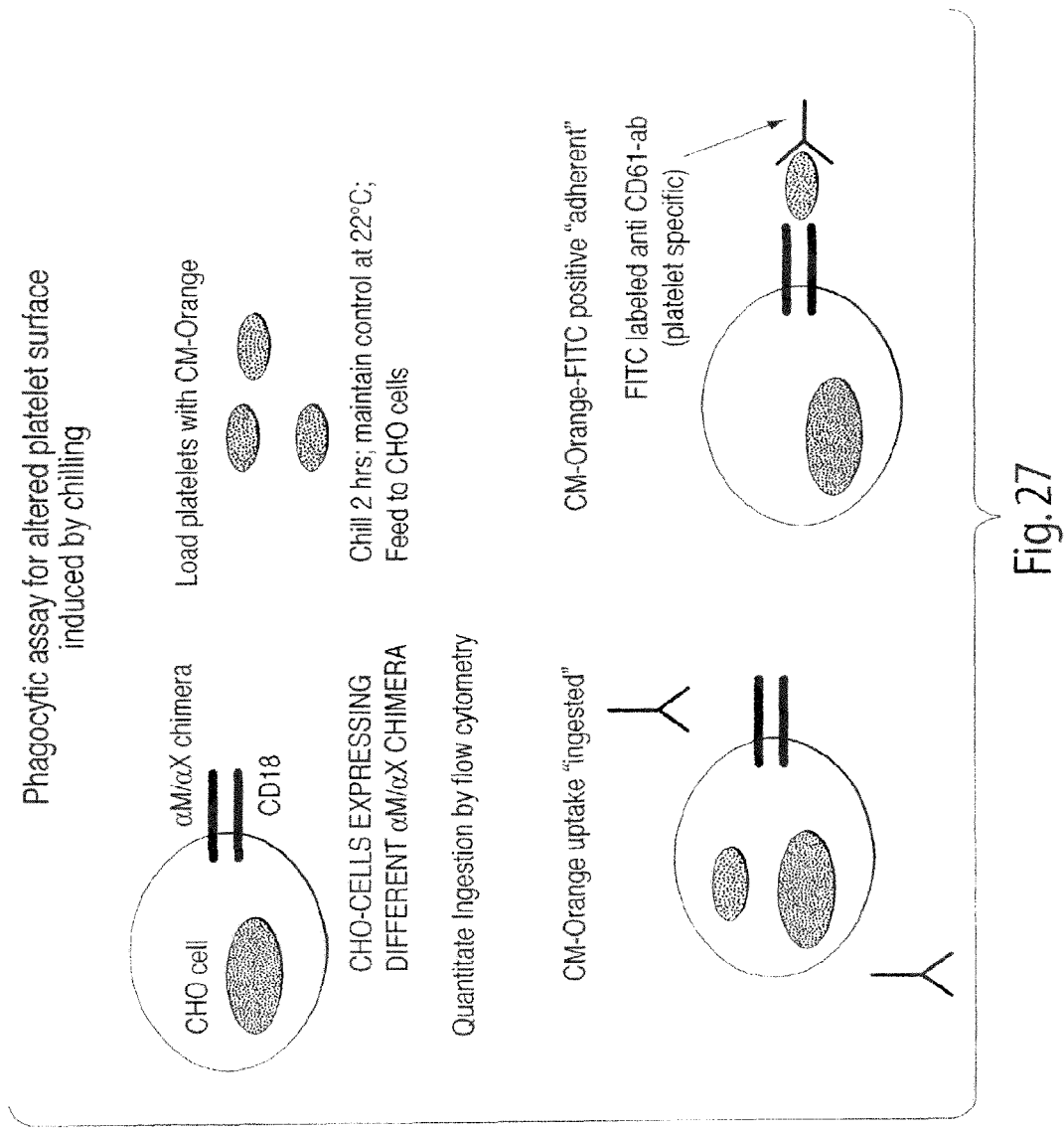
FIG. 27 illustrates a phagocytic assay for altered platelet surface induced by chilling.
Figure 28:
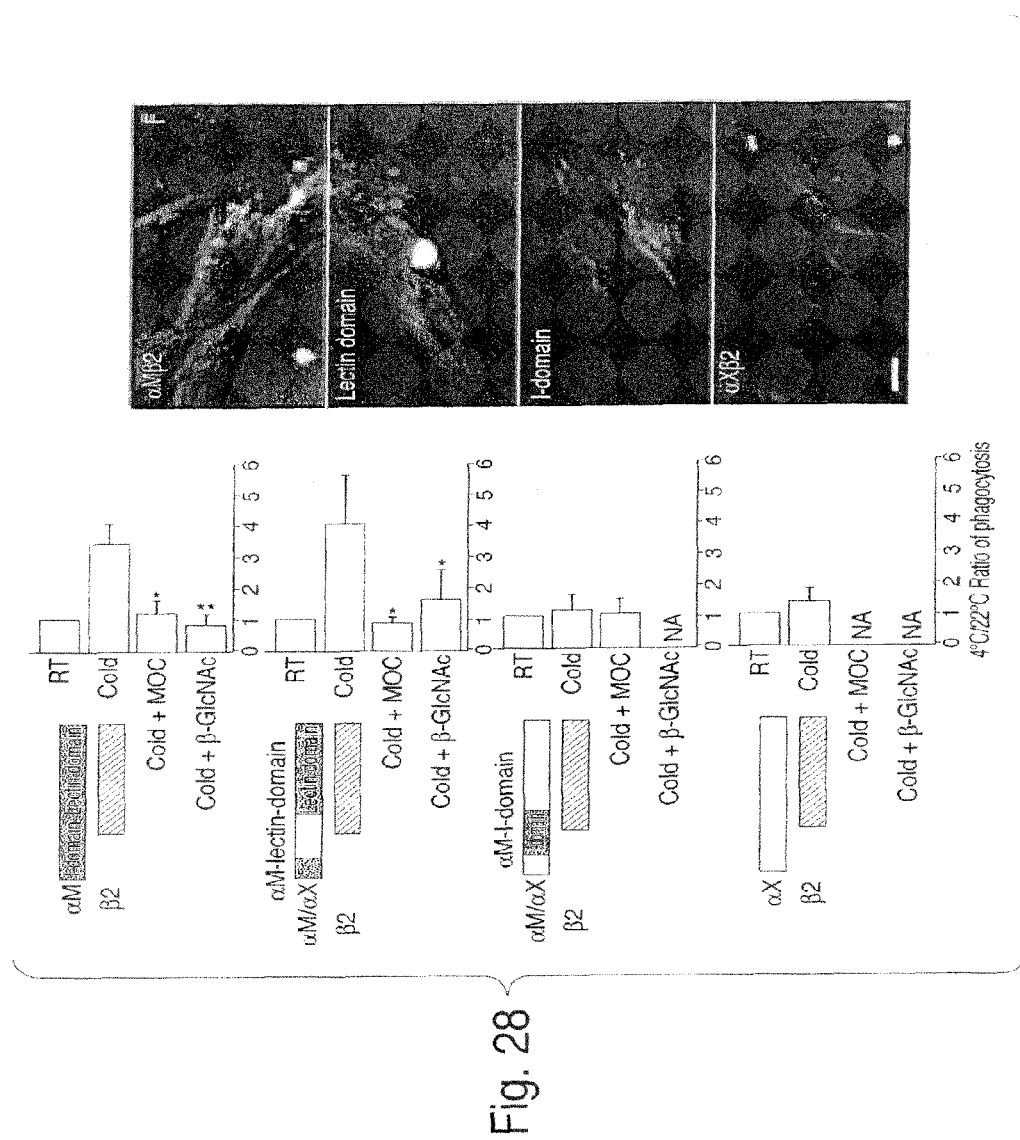
FIG. 28 shows that the αM-lectin domain mediates chilled human platelet phagocytosis.
Figure 29:
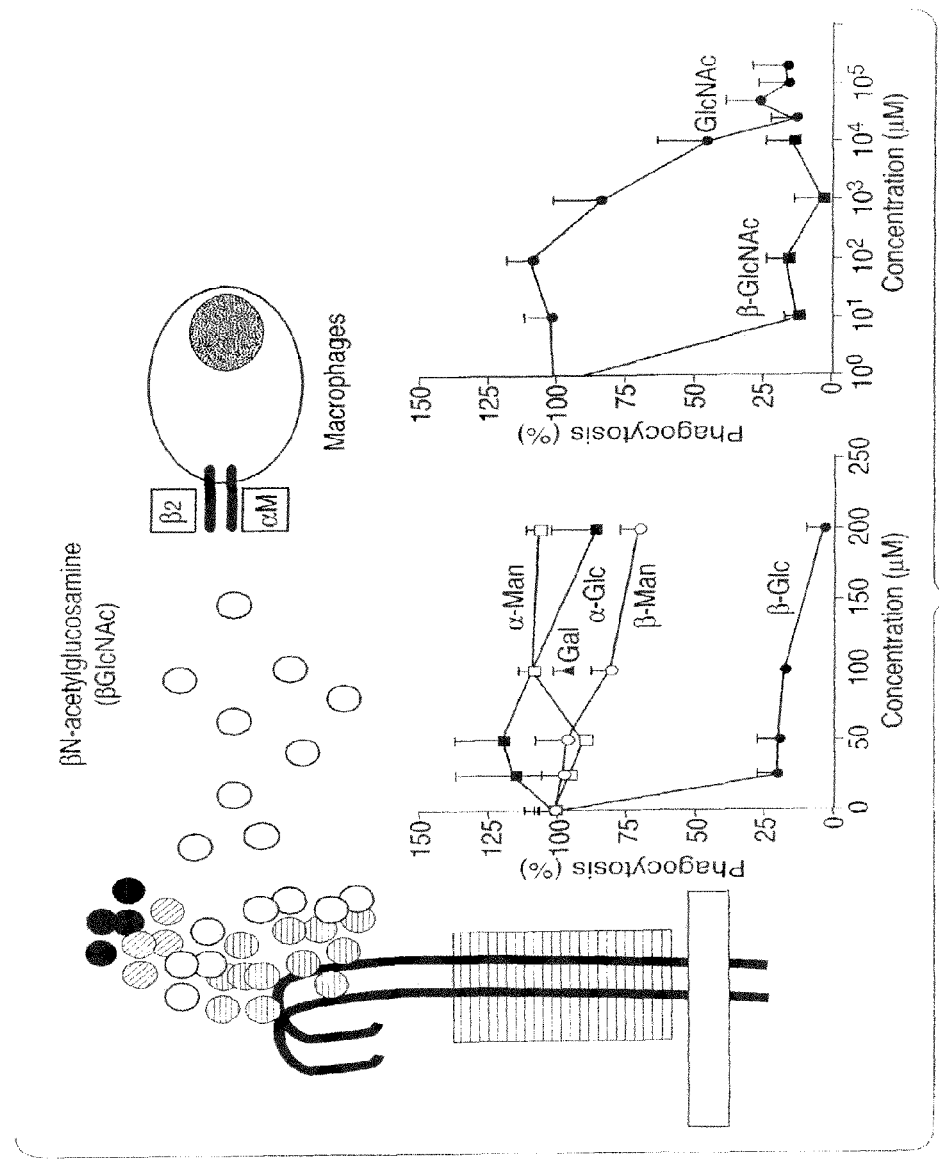
FIG. 29 shows that macrophage αM/β2 receptors recognize βGlcNAc residues on clustered GP1bα receptors of chilled platelets.
Figure 30:
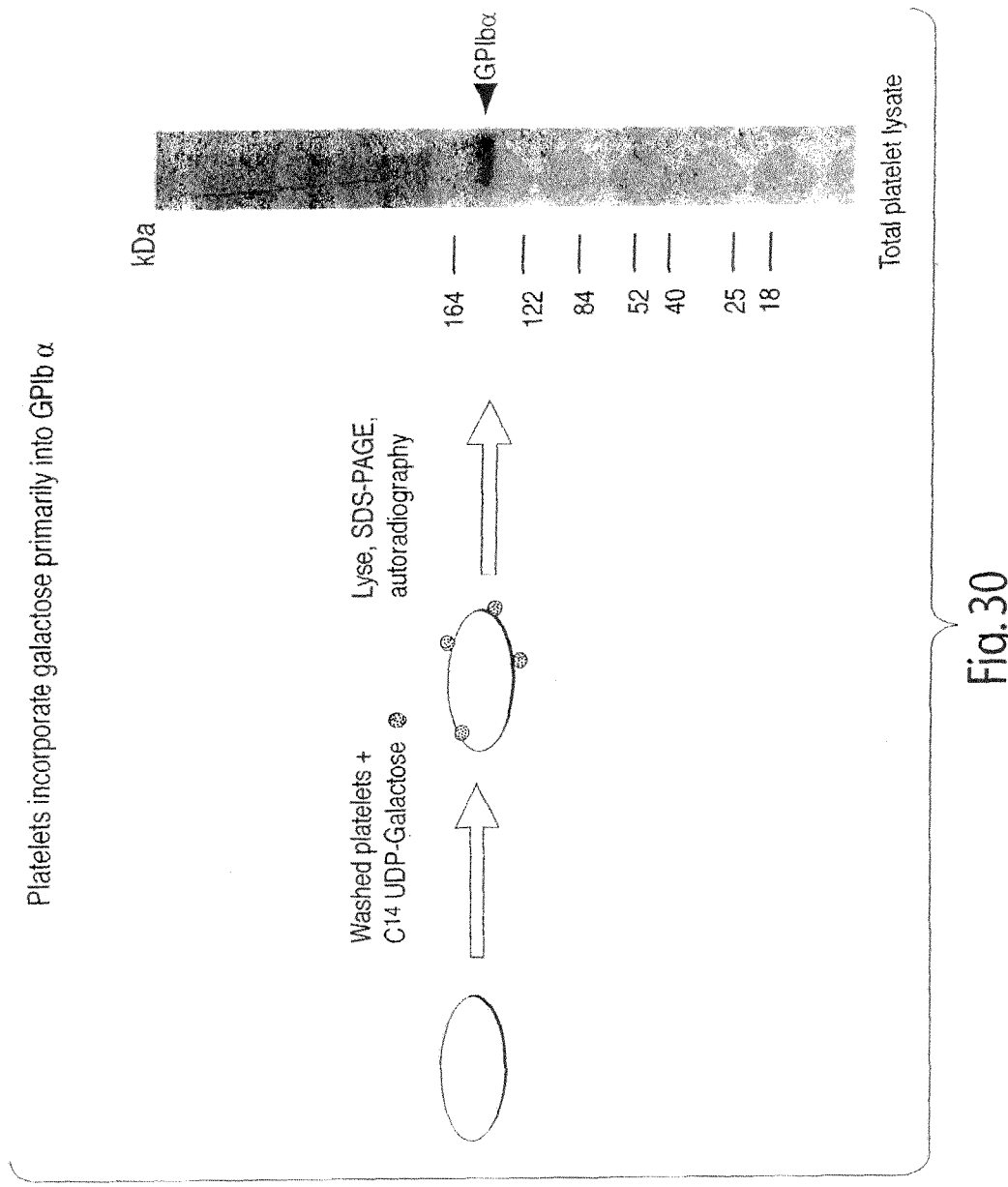
FIG. 30 illustrates the galactosylation of platelets through GP1bα.
Figure 31:
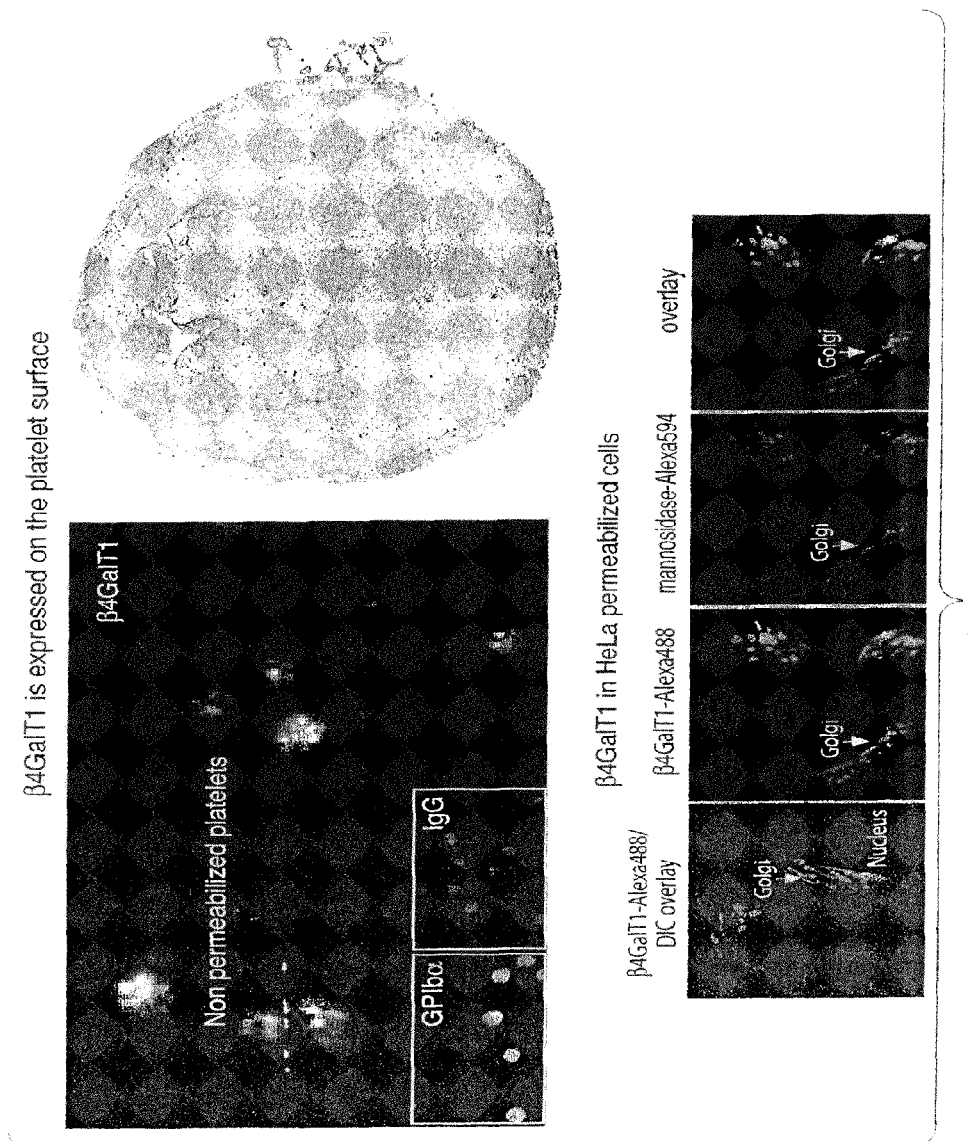
FIG. 31 shows expression of β4GalT1 on the platelet surface.
Figure 32:
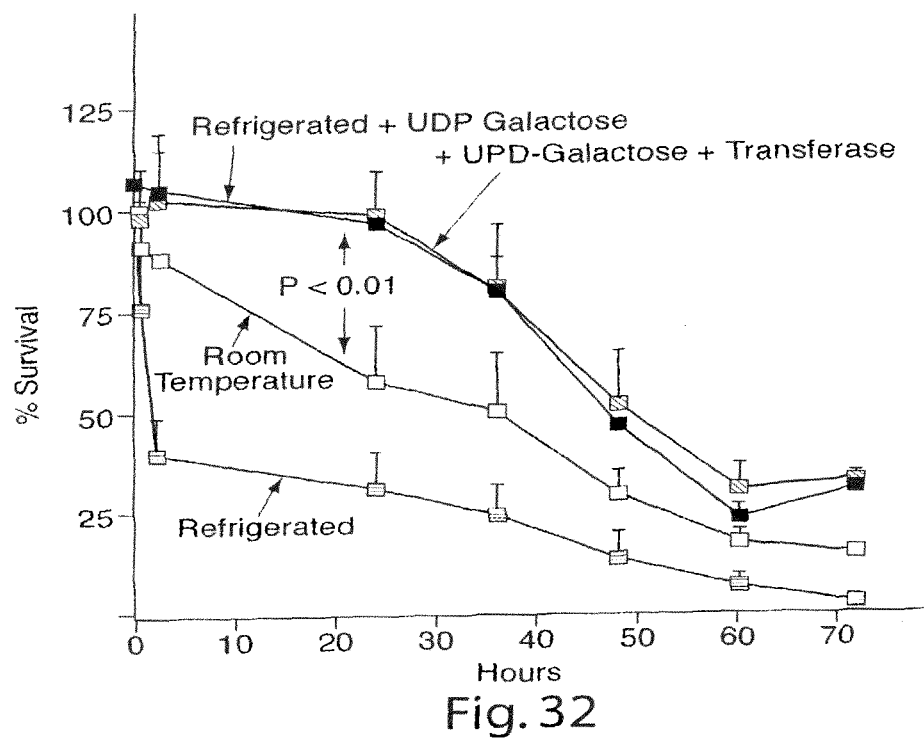
FIG. 32 illustrates that galactosylated chilled murine platelets can circulate in vivo.
Figure 33:
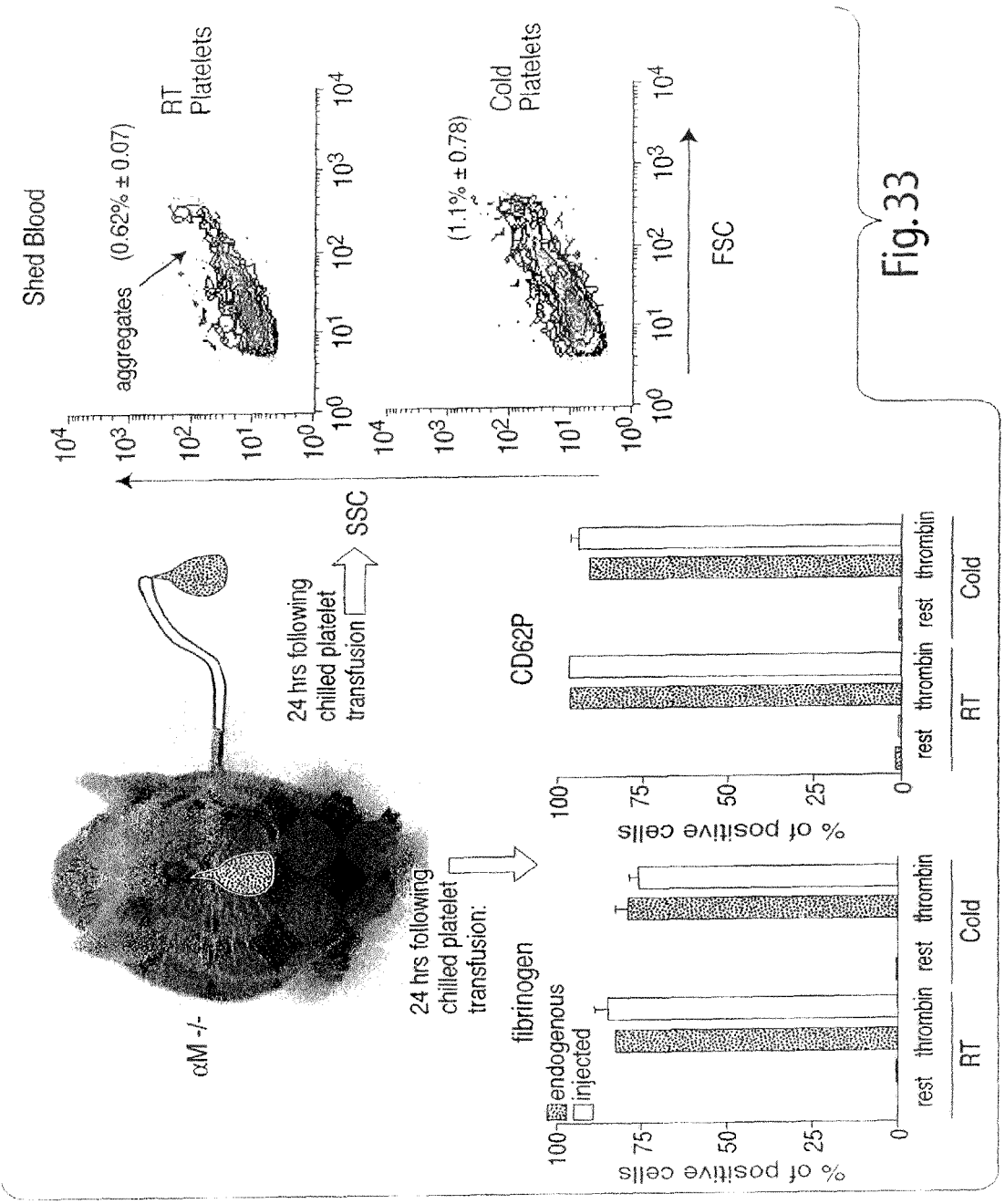
FIG. 33 illustrates that galactosylated chilled murine platelets can function normally in murine models.
Figure 35:
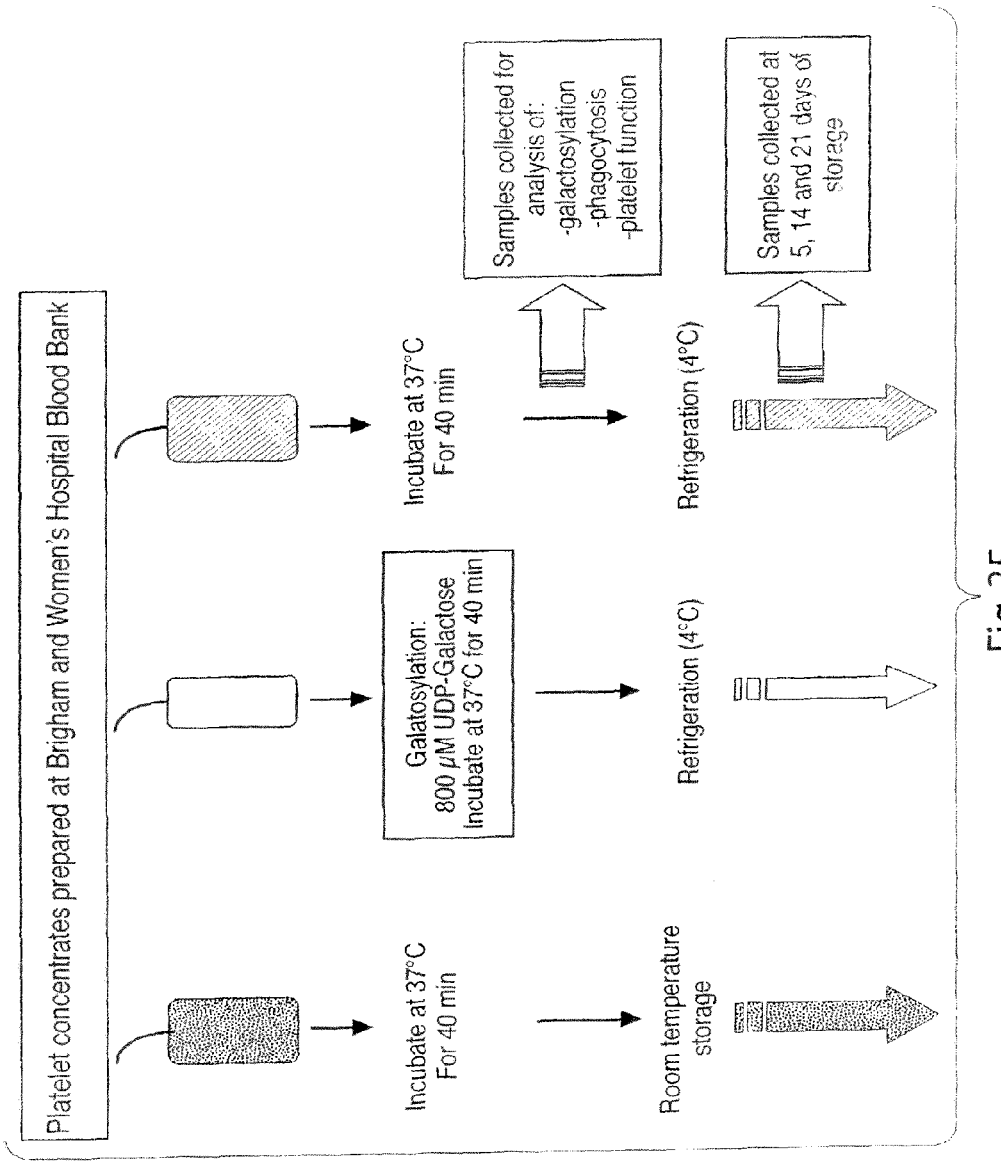
FIG. 35 illustrates a method for galactosylation of human platelet concentrates.
Figure 36:
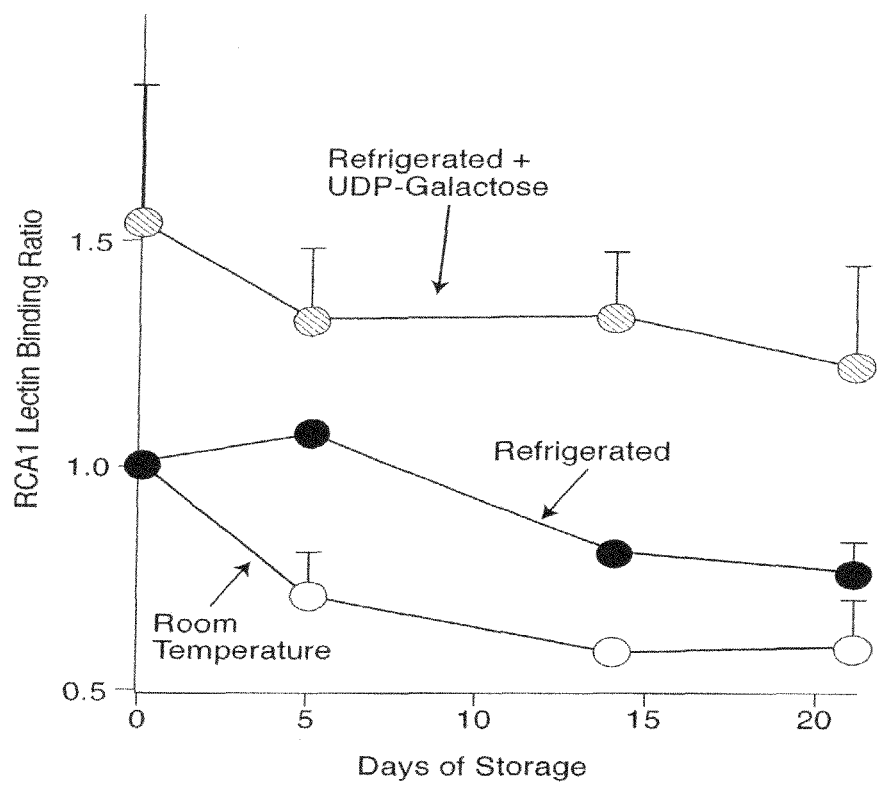
FIG. 36 shows surface galactose on platelet concentrates is stable.
Figure 37:
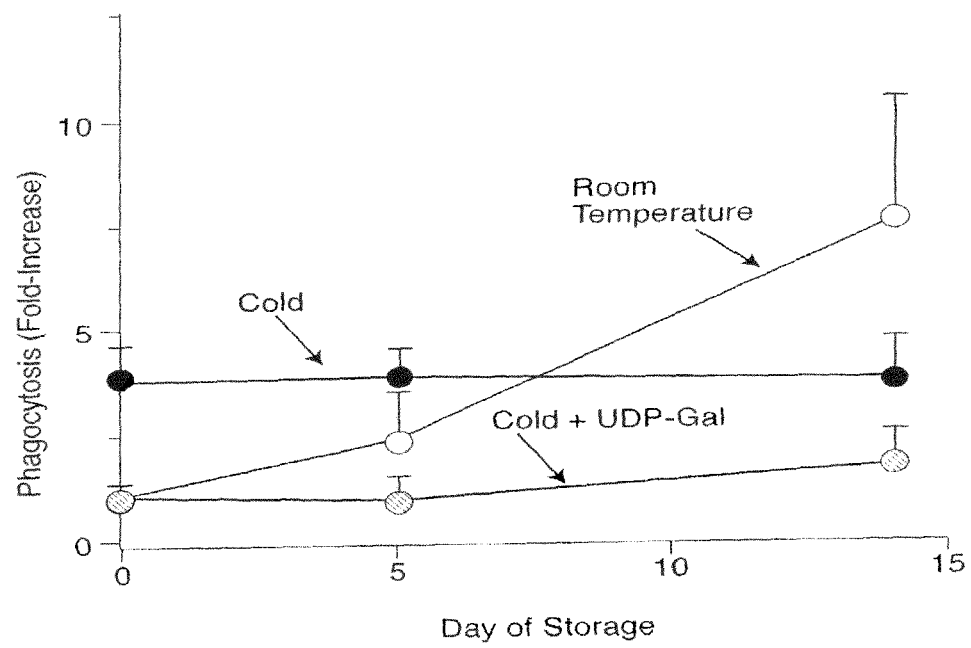
FIG. 37 shows that galactosylation inhibits phagocytosis by THP-1 macrophages of human chilled platelets.
Figure 38:
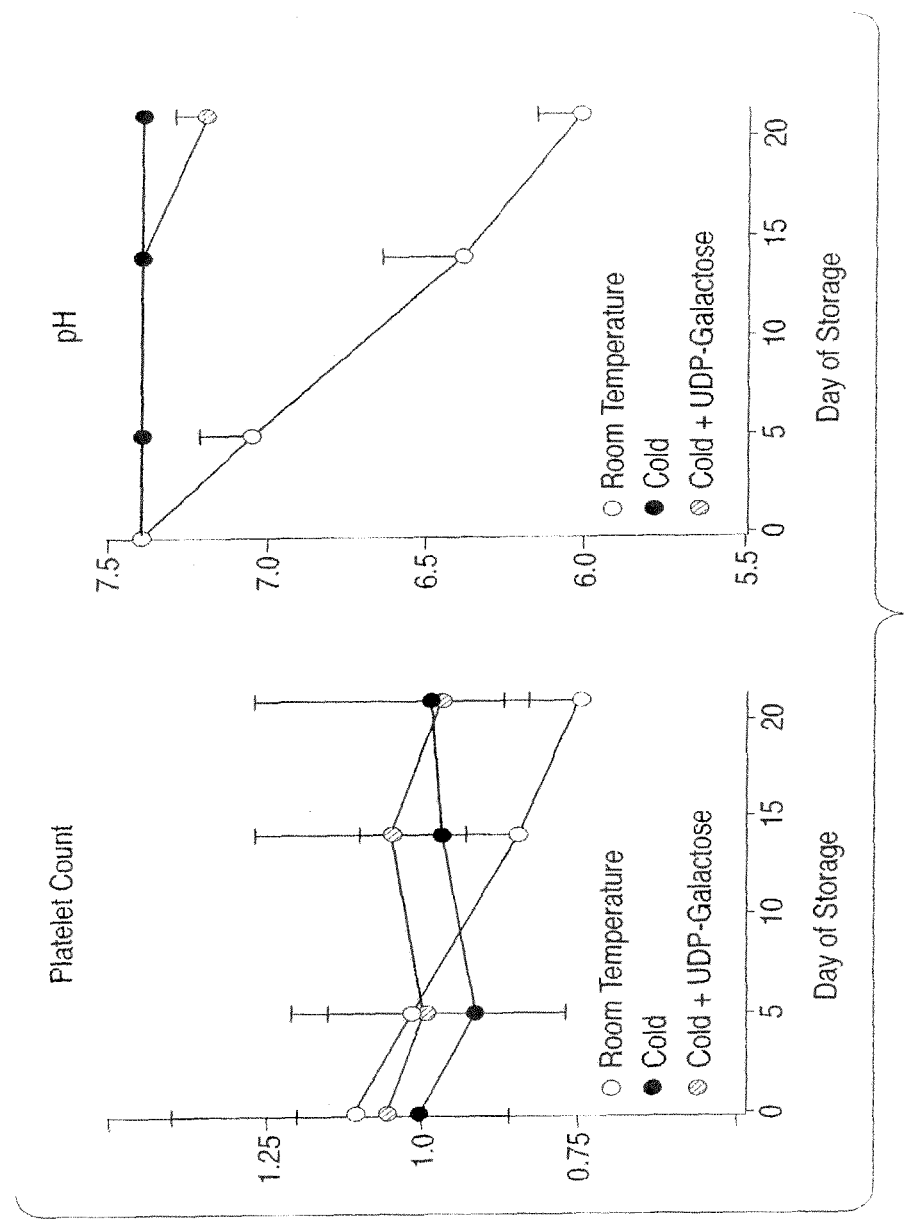
FIG. 38 shows that platelet counts and pH remain unchanged in refrigerated platelet concentrates.
Figure 39:
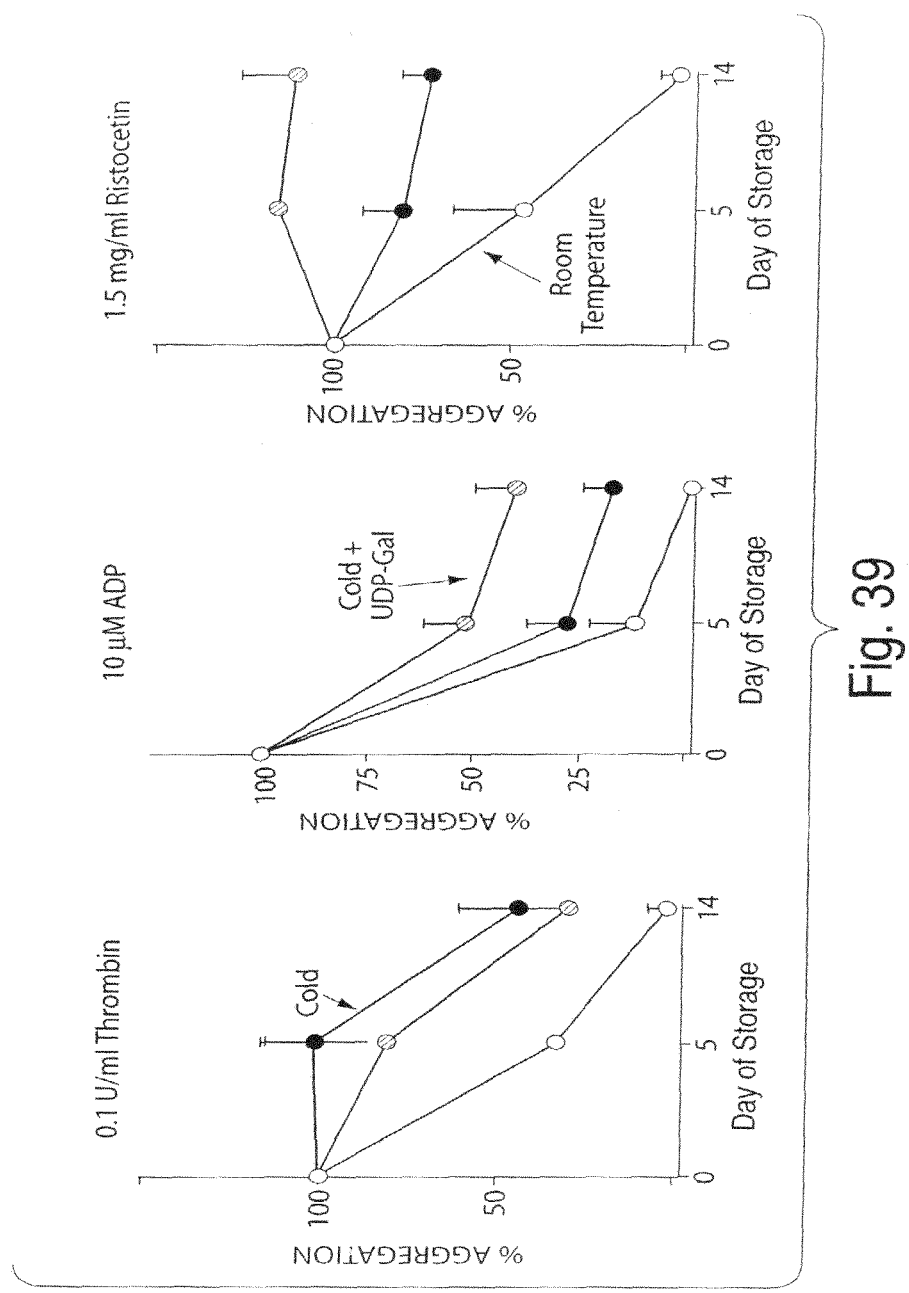
FIG. 39 shows the effects of refrigeration and galactosylation on retention of platelet responses to agonists during storage of concentrates.
Figure 40:
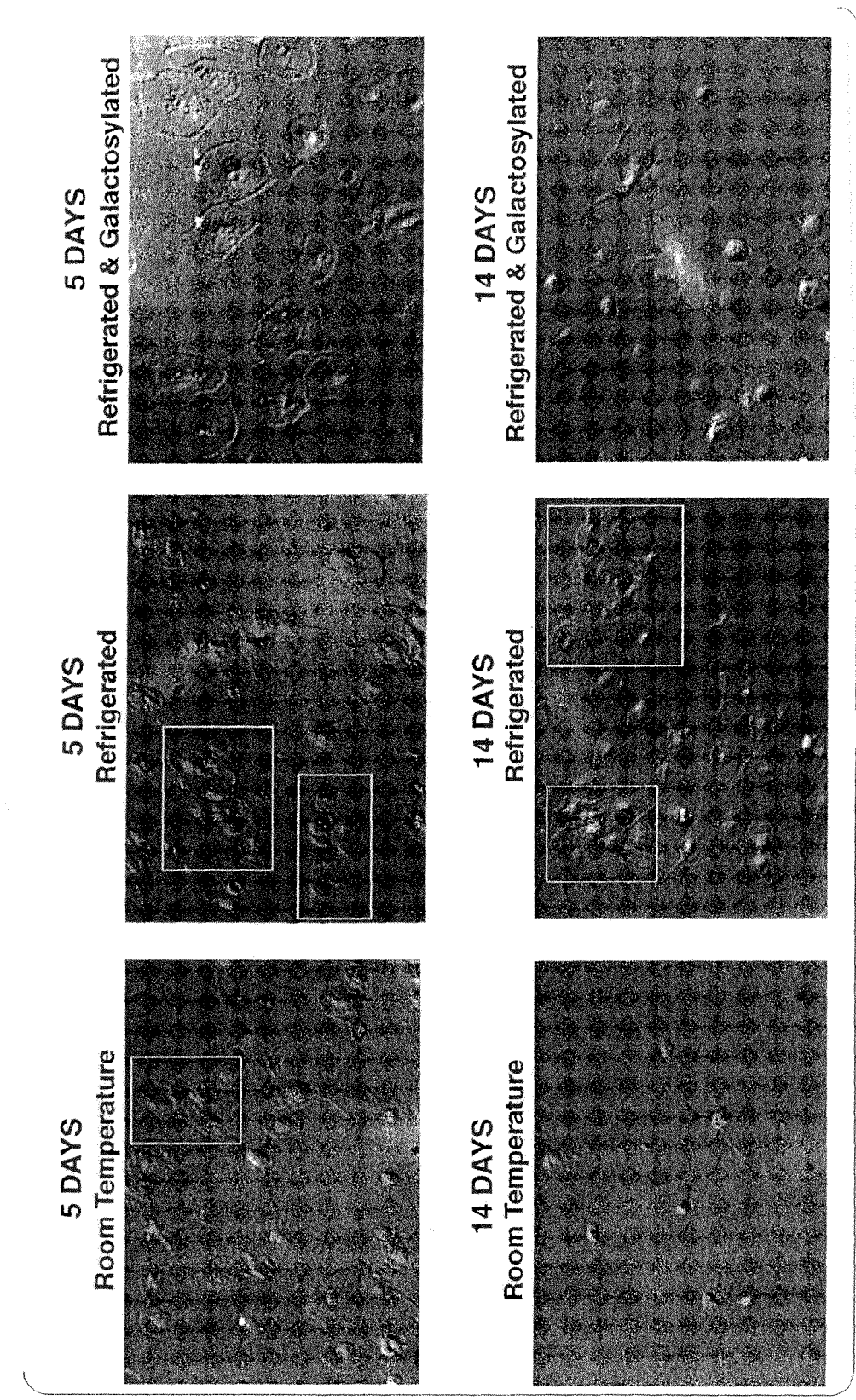
FIG. 40 shows the effect of storage conditions on shape change (spreading) and clumping of platelets in concentrates.
Figure 41:
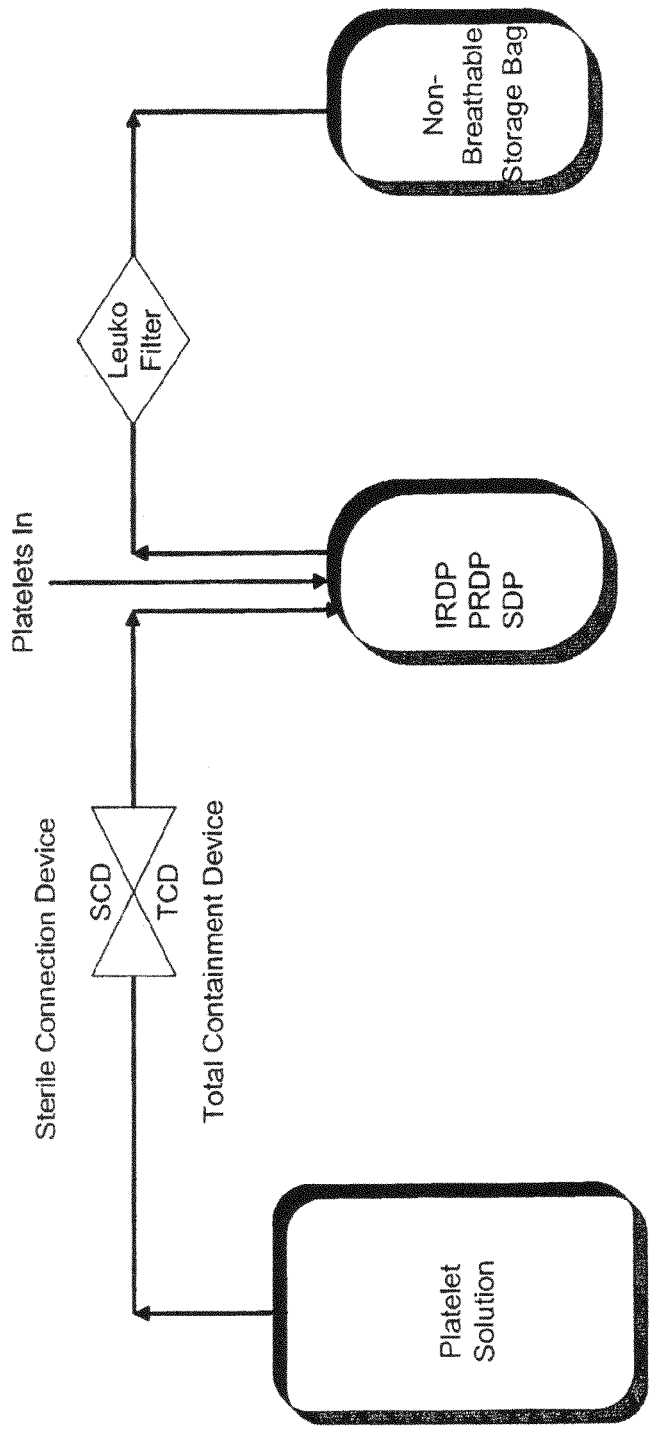
FIG. 41 illustrates an embodiment of the invention wherein a bioprocess for collecting, treating and storing platelets is described. Platelets are derived from a variety of blood sources, including IRDP—Individual Random Donor Platelets, PRDP—Pooled Random Donor Platelets and SDP—Single Donor Platelets. The container having the glycan modifying agent, e.g., a solution of UDP-Gal and/or CMP-NeuAc is sterile docked to the bag containing the platelets. A sterile dock is also referred to as a sterile connection device (SCD) or a total containment device (TCD). The sterile dock permits connection of two pieces of conduit while maintaining sterility of the system. The glycan modifying agent is mixed with the platelets and then the modified platelets are transferred to a non-breathable bag. The glycan modifying agent can be introduced to the platelets at a variety of times, e.g., before infusion, before storage, after componentization or directly to whole blood, or during the platelet apheresis procedure at the time of donation. Likewise, the glycan modifying solution may be provided in a variety of forms, such as full strength concentration liquid, concentrated liquid—diluted before use, dehydrated, freeze dried, lyophilisized, powder, frozen, viscous fluid, suspension, base and activator, or reactant and catalyst. In this embodiment, the blood is passed through a leukocyte filter. Various methods of leukocyte depletion are known in the art, e.g., glass wool or other affinity separation methods for removing leukocyte fractions from whole blood, and provide examples of means for filtering the leukocytes from the rest of the blood and specifically the platelets.
Figure 42:
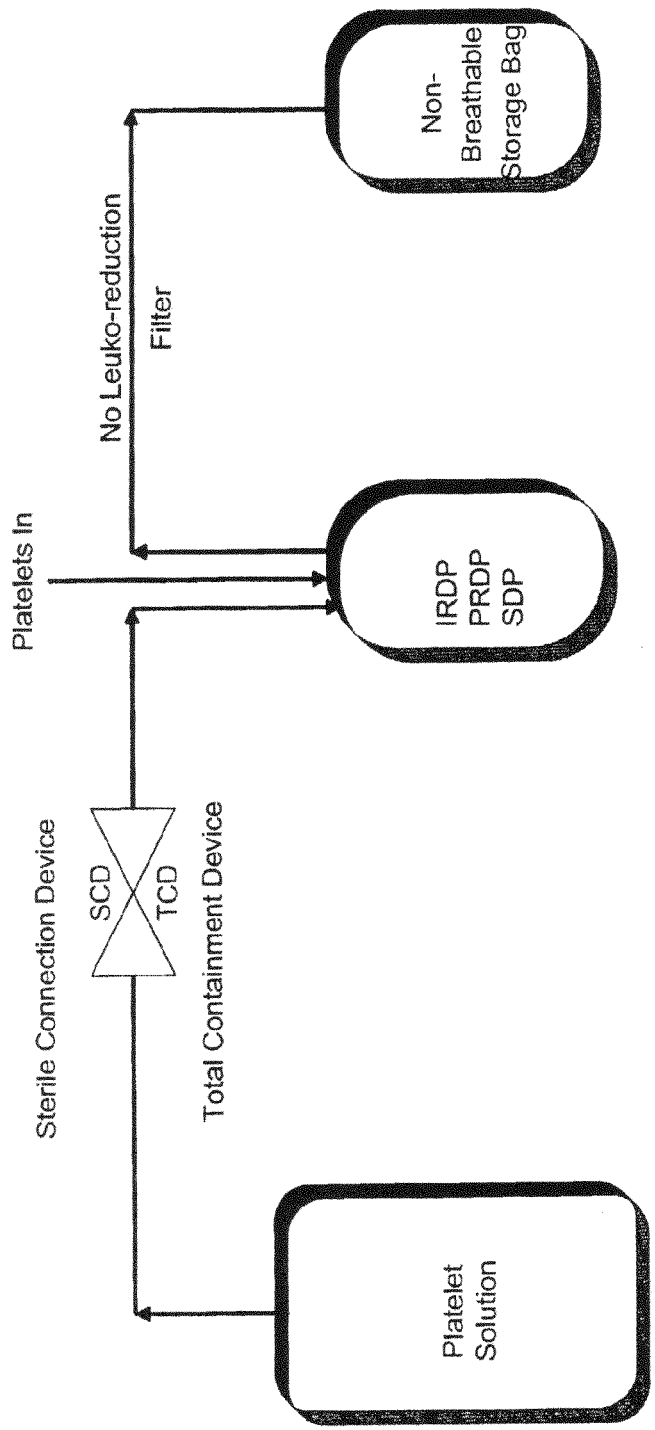
FIG. 42 illustrates another embodiment of the invention wherein a bioprocess for collecting, treating and storing platelets is described. This illustration is similar to FIG. 41 but does not include a leukocyte filter.
Figure 43:
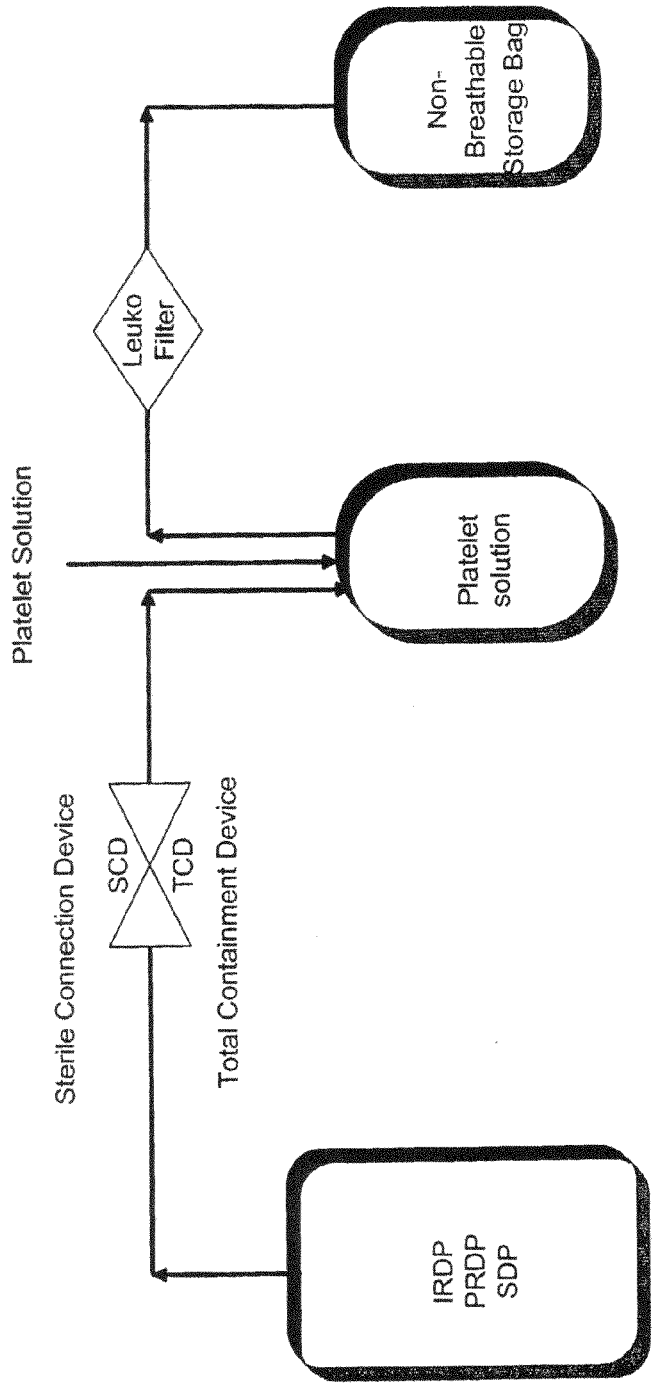
FIG. 43 illustrates another embodiment of the invention wherein a bioprocess for collecting, treating and storing platelets is described. The bag containing the platelets is sterile docked to the bag containing the platelet solution. The glycans modifying solution, also called a platelet solution, is mixed with the platelets and then transferred to a non-breathable bag and thru a leukocyte filter.
Figure 44:
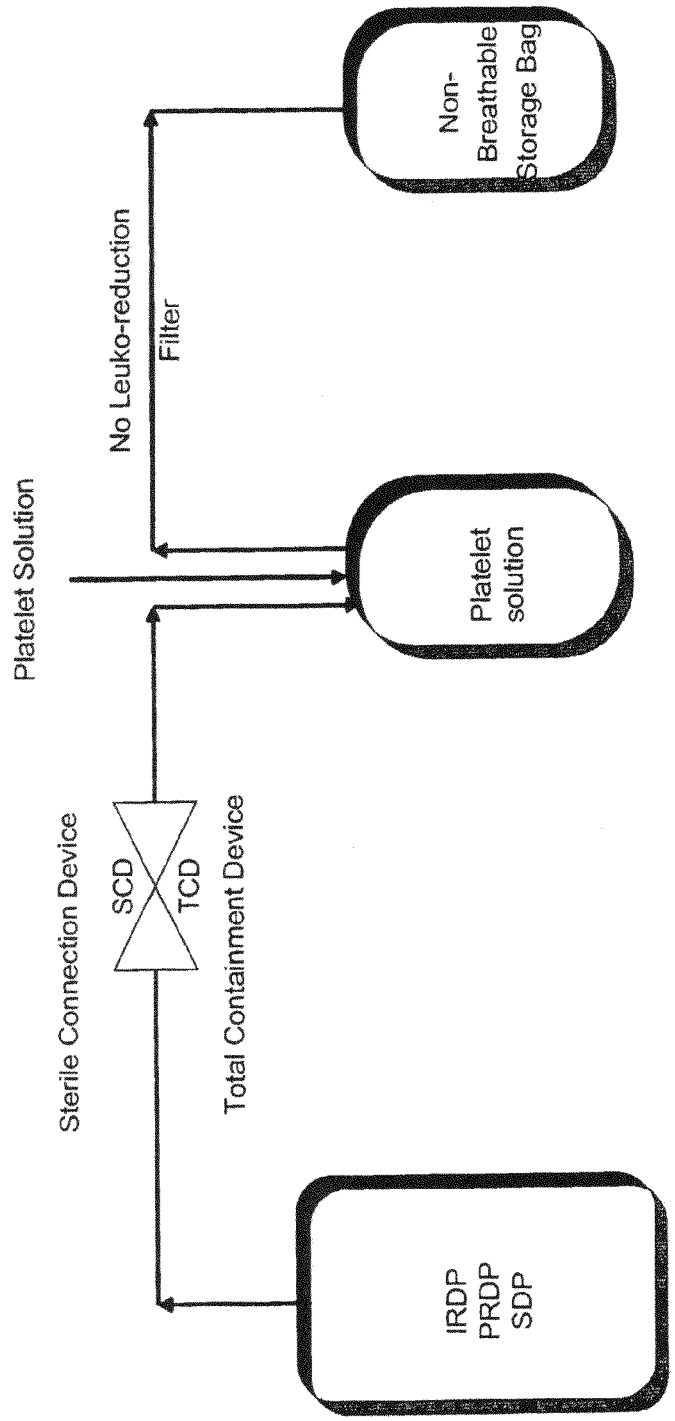
FIG. 44 illustrates a variation of FIG. 43, that does not include a leukocyte filter.
Figure 45:
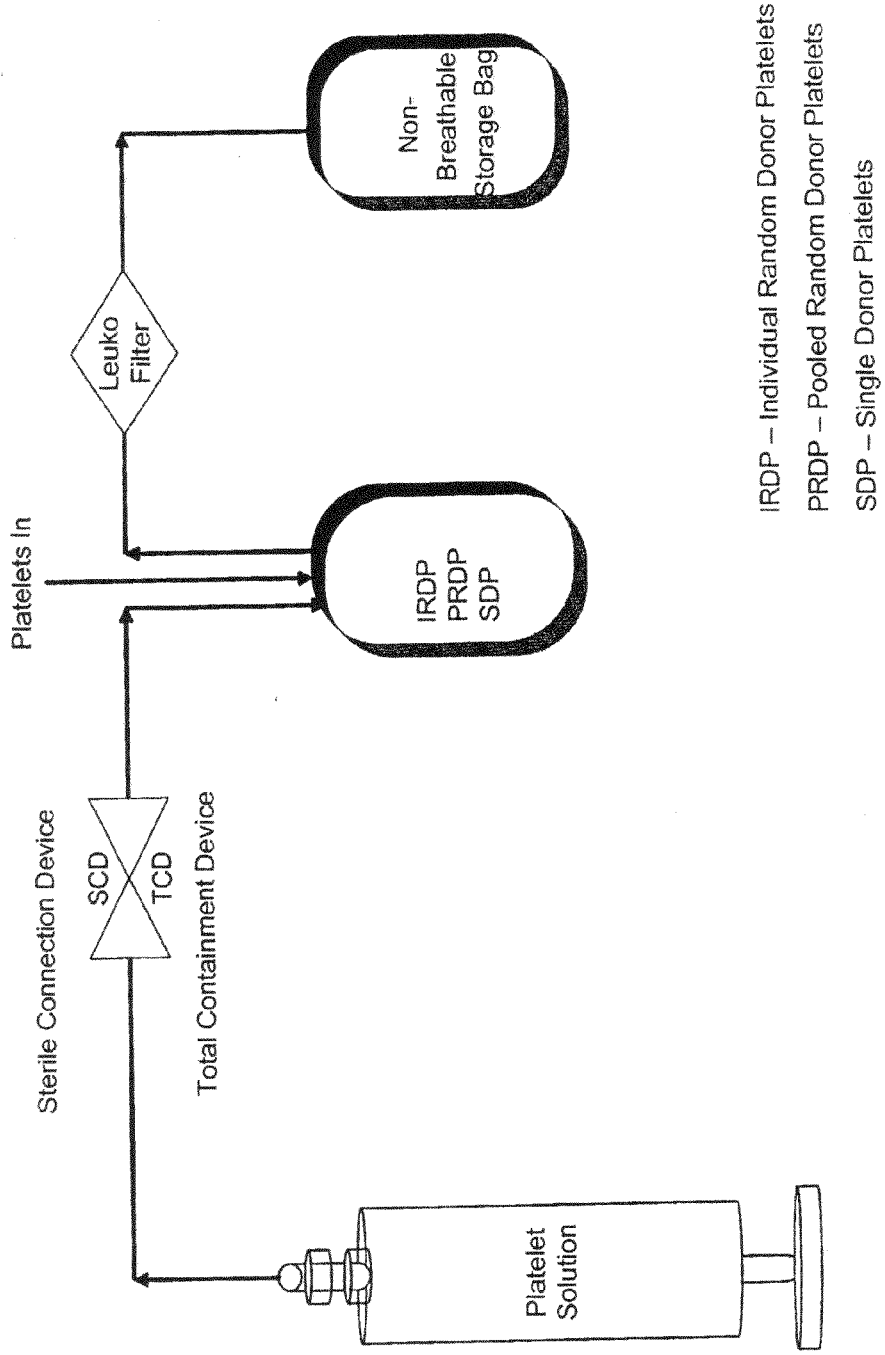
FIG. 45 illustrates another embodiment of the invention wherein a bioprocess for collecting, treating and storing platelets is described. The syringe containing the platelet solution (UDP-Gal and/or CMP-NeuAc) is sterile docked to the bag containing the platelets. The platelet solution is mixed with the platelets and then transferred to a non-breathable bag and thru a leukocyte filter.
Figure 46:
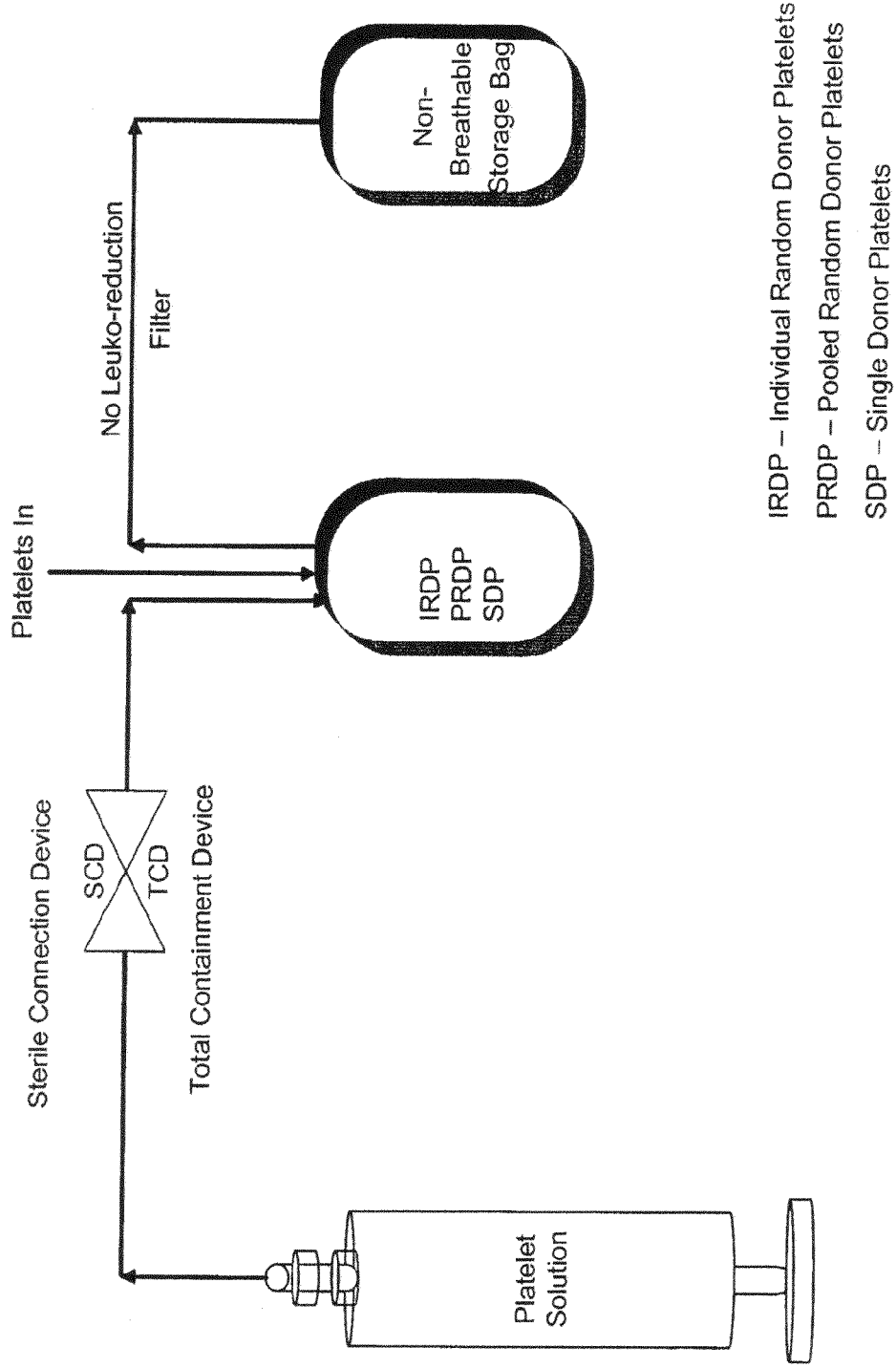
FIG. 46 illustrates a variation of FIG. 45, that does not include a leukocyte filter.
Figure 47:
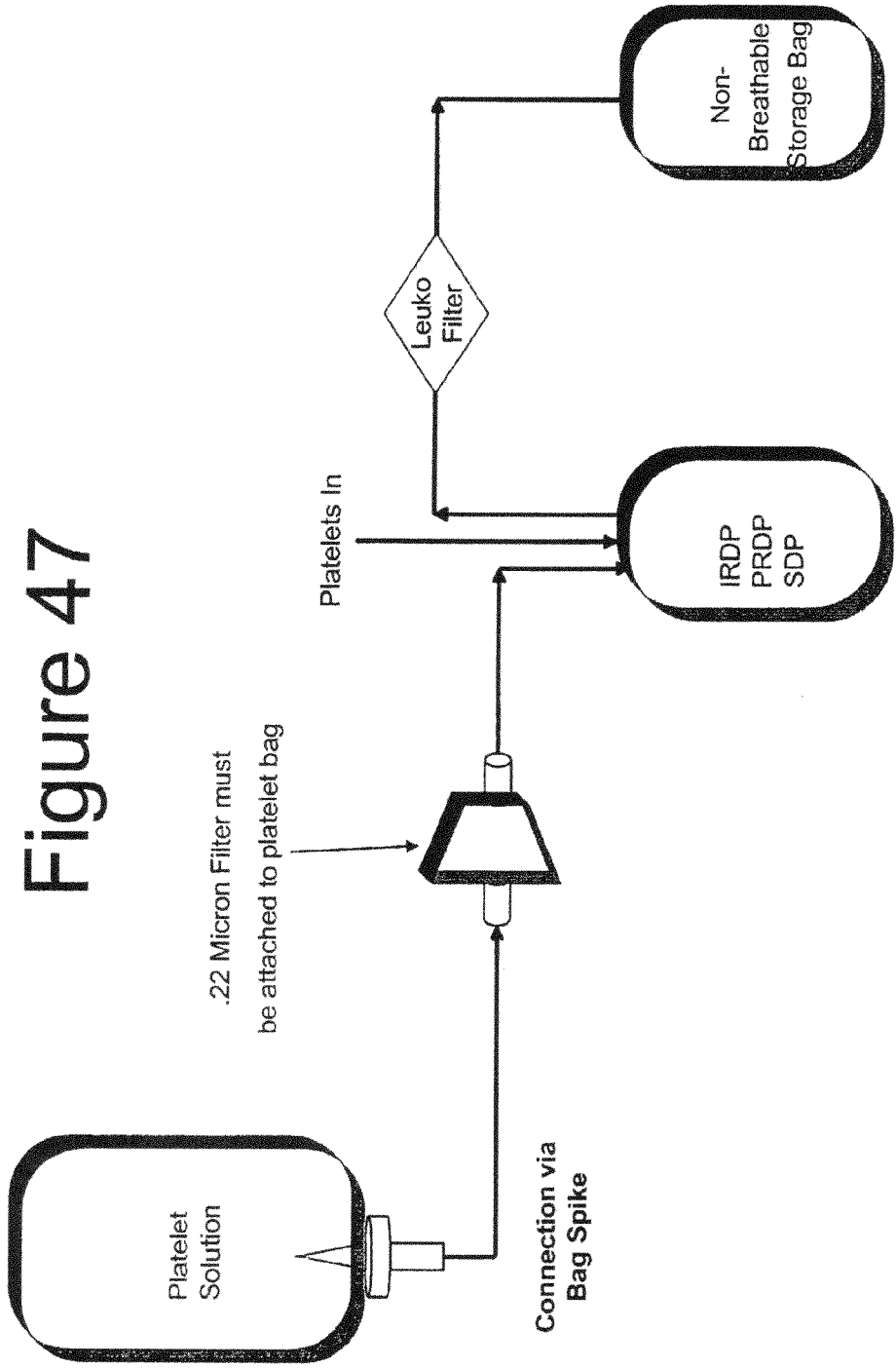
FIG. 47 illustrates another embodiment of the invention wherein a bioprocess for collecting, treating and storing platelets is described. The bag containing the platelet solution (UDP-Gal and/or CMP-NeuAc) is connected to the container port using a bag spike thru a 0.22 micron filter to the bag containing the platelets. The platelet solution is mixed with the platelets and then transferred to a non-breathable bag and thru a leukocyte filter. A 0.22 micron filter is illustrated, but larger pore diameter filters are suitable to provide increased flow rate. Median pore sizes greater than about 1 micron are not suitable for sterile filtration. Preferred sizes are less than about 0.75 microns, more preferably less than about 0.5 microns, and most preferably about 0.22 microns.
Figure 48:
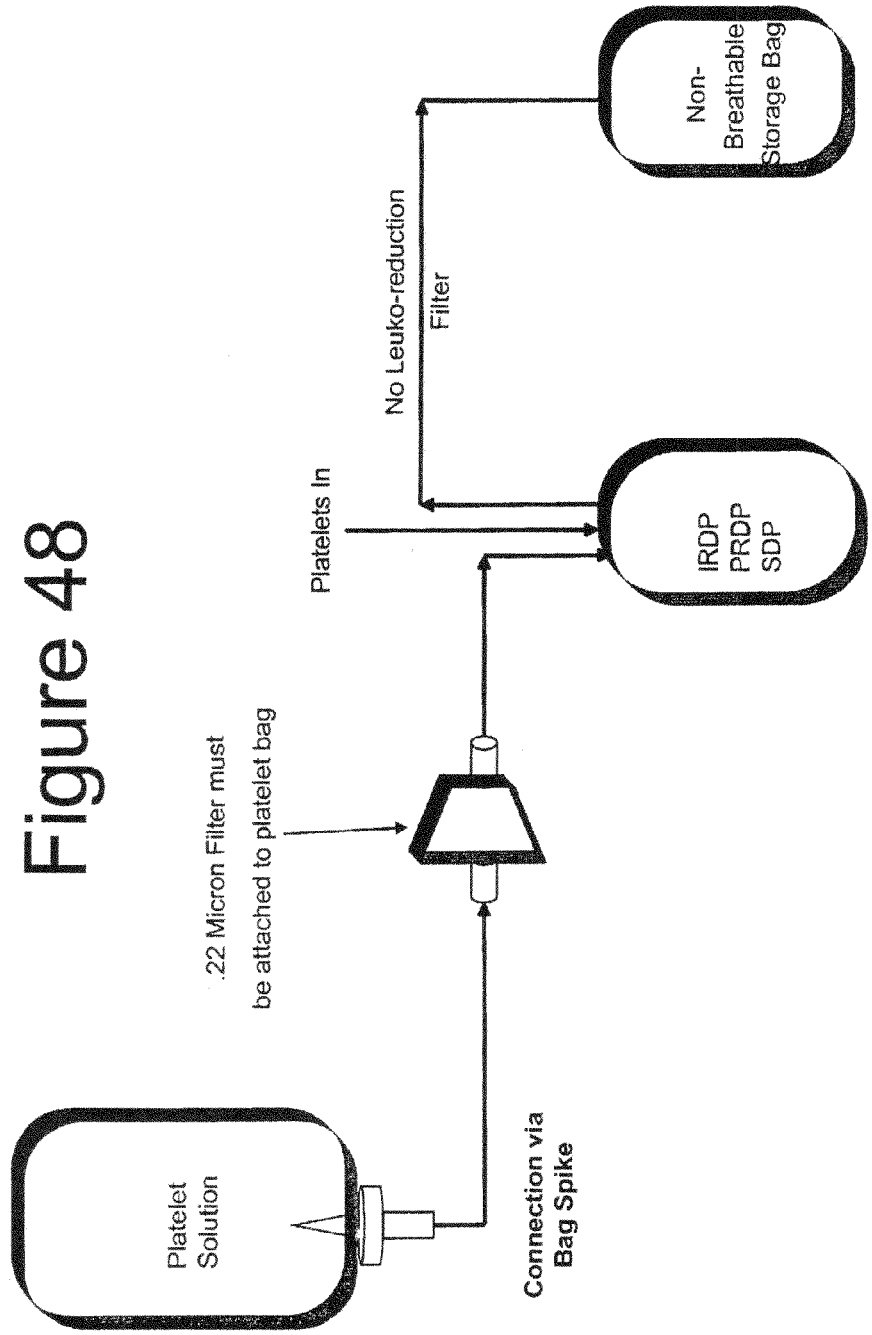
FIG. 48 illustrates a variation of FIG. 47, that does not include a leukocyte filter.
Figure 49:
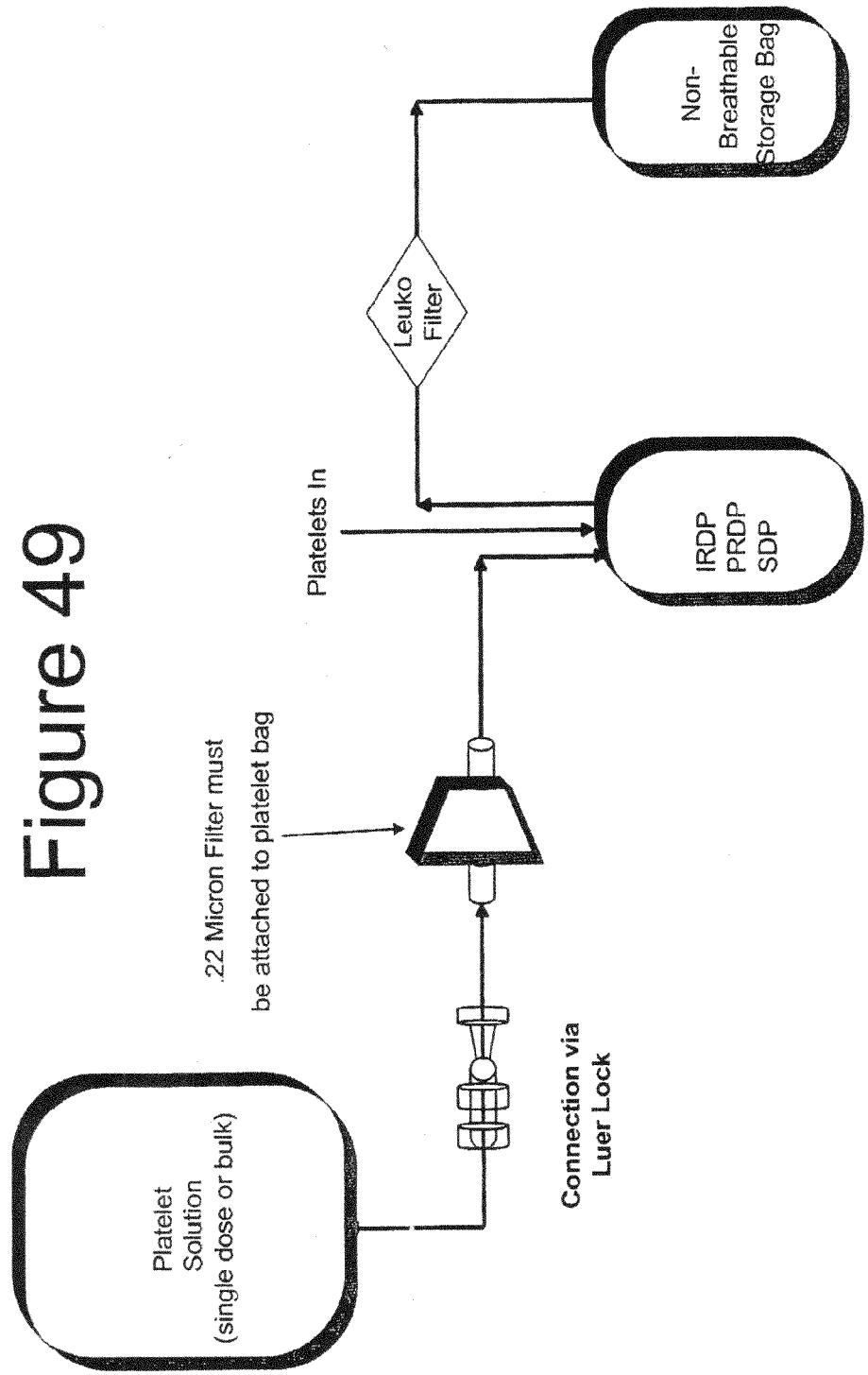
FIG. 49 illustrates another embodiment of the invention wherein a bioprocess for collecting, treating and storing platelets is described. The bag containing the platelet solution (either single dose or bulk) is connected using a luer lock thru a 0.22 micron filter to the bag containing the platelets. The platelet solution is mixed with the platelets and then transferred to a non-breathable bag and thru a leukocyte filter.
Figure 50:
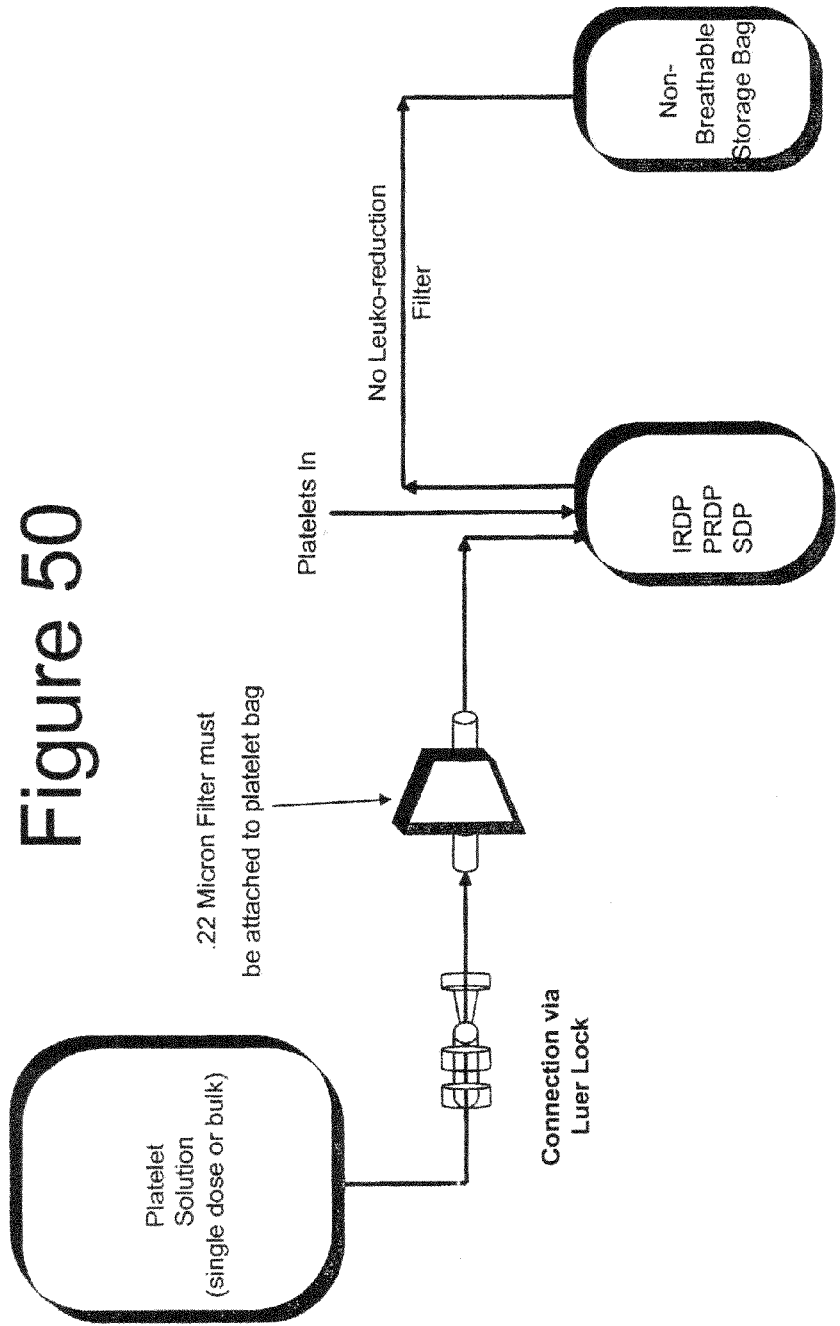
FIG. 50 illustrates a variation of FIG. 49, that does not include a leukocyte filter.
Figure 51:
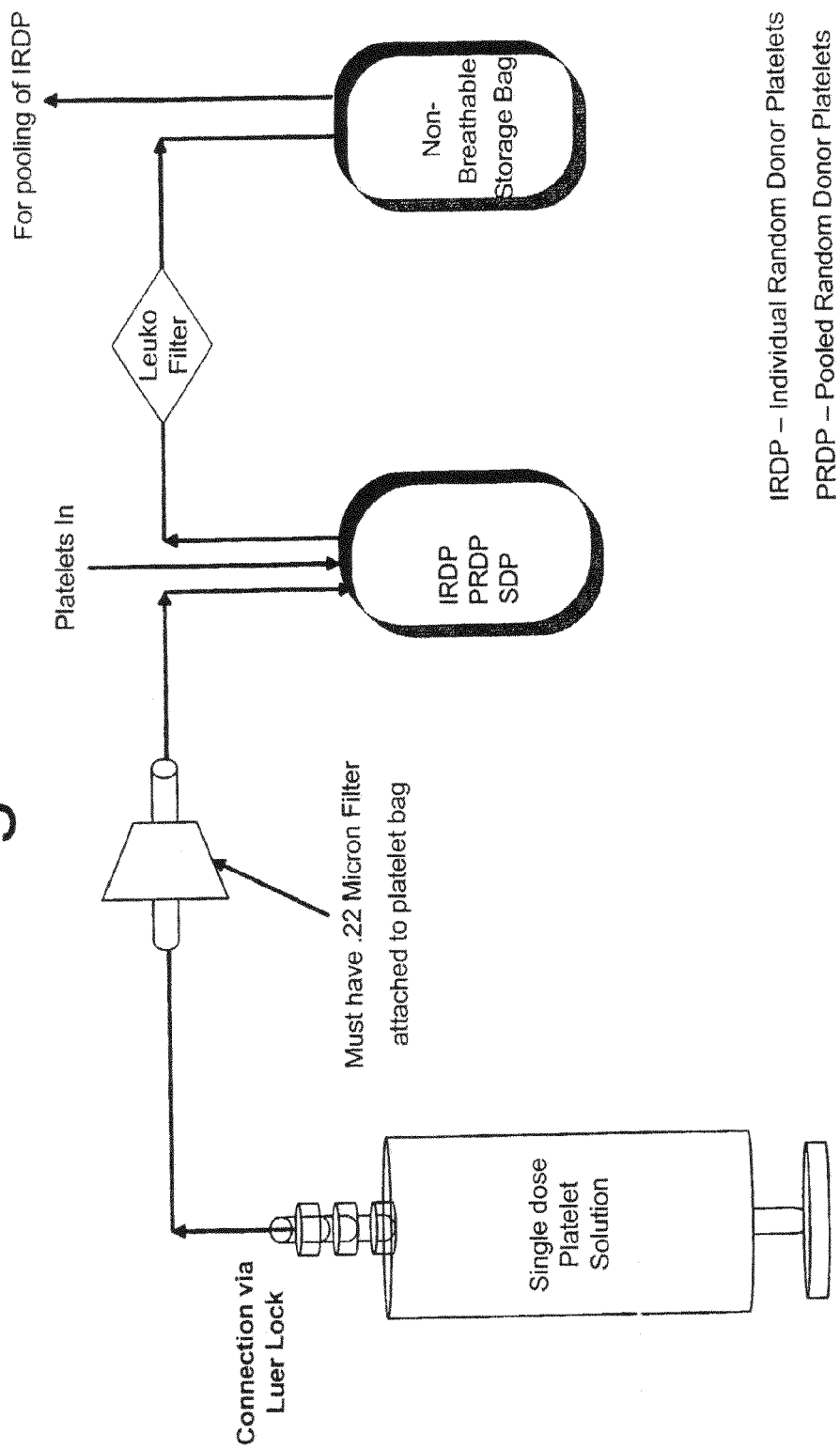
FIG. 51 illustrates another embodiment of the invention wherein a bioprocess for collecting, treating and storing platelets is described. The syringe containing the platelet solution is connected using a luer lock thru a 0.22 micron filter to the bag containing the platelets. The platelet solution is mixed with the platelets and then transferred to a non-breathable bag and thru a leukocyte filter. Also shown, IRDP can be pooled to form PRDP.
Figure 52:
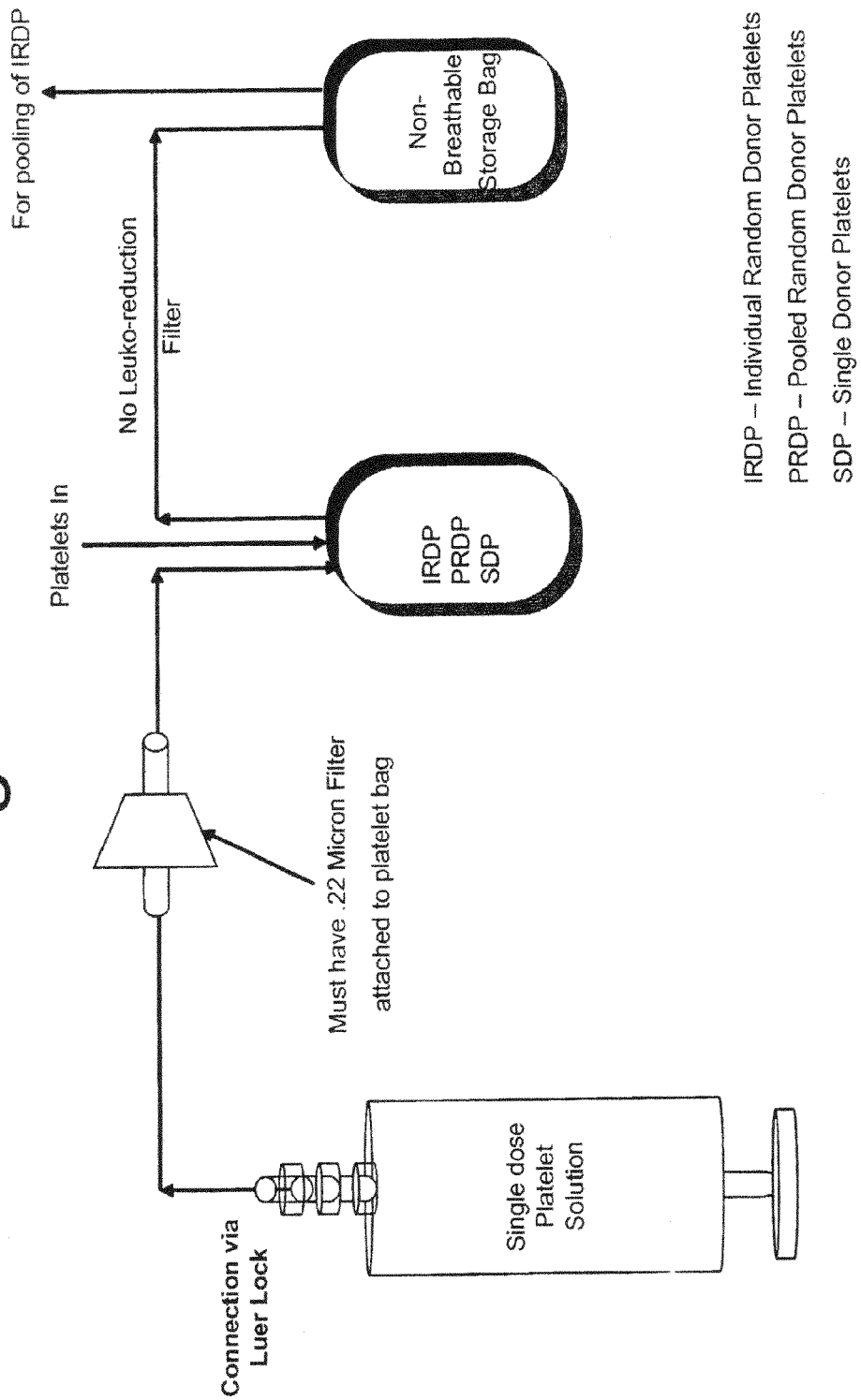
FIG. 52 illustrates a variation of FIG. 51, that does not include a leukocyte filter.
Figure 53:
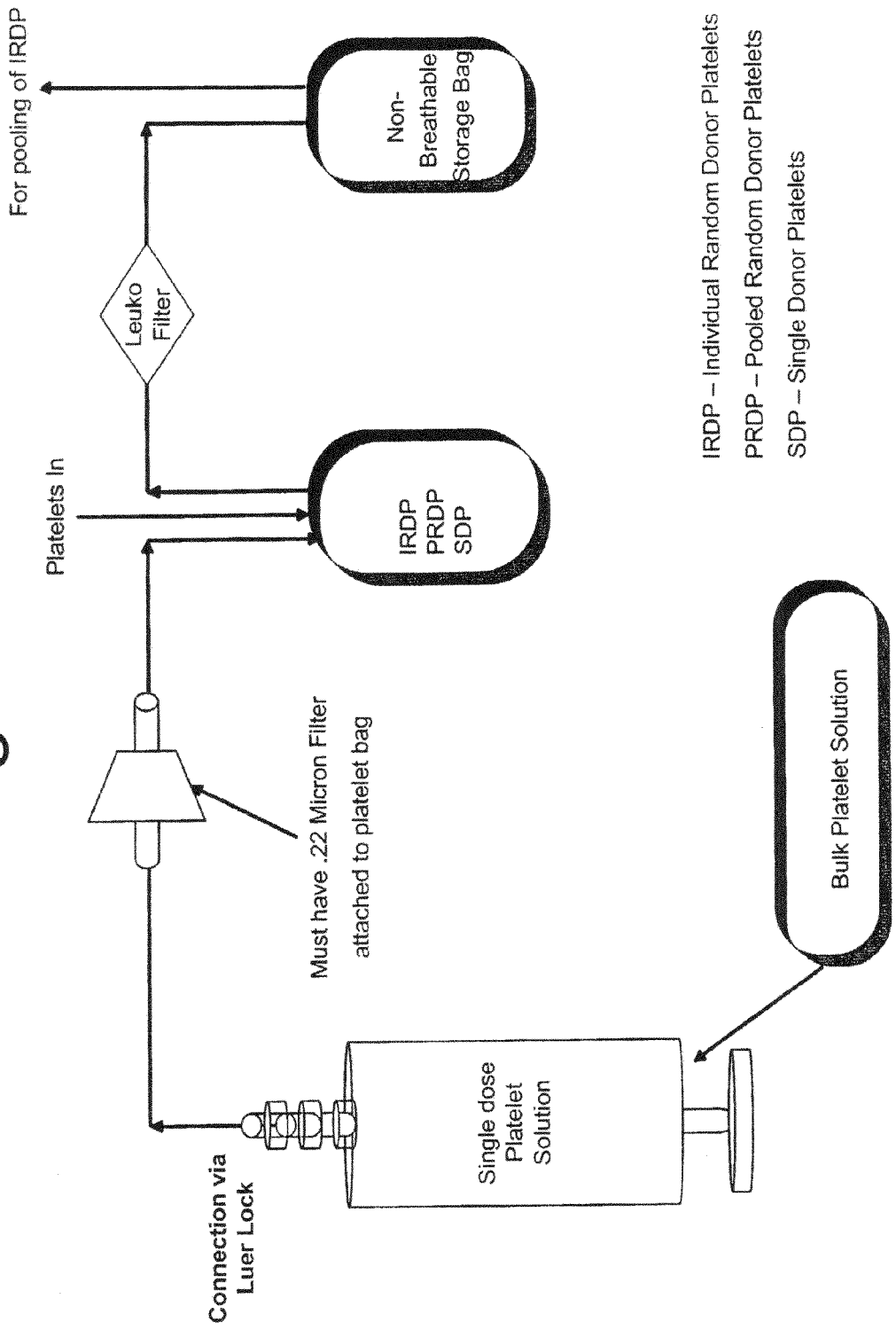
FIG. 53 illustrates another embodiment of the invention wherein a bioprocess for collecting, treating and storing platelets is described. The syringe containing the platelet solution is connected using a luer lock thru a 0.22 micron filter to the bag containing the platelets. The platelet solution is mixed with the platelets and then transferred to a non-breathable bag and thru a leukocyte filter. The syringe can be aseptically refilled from the bulk platelet solution because of the in-line filtration device.
Figure 54:
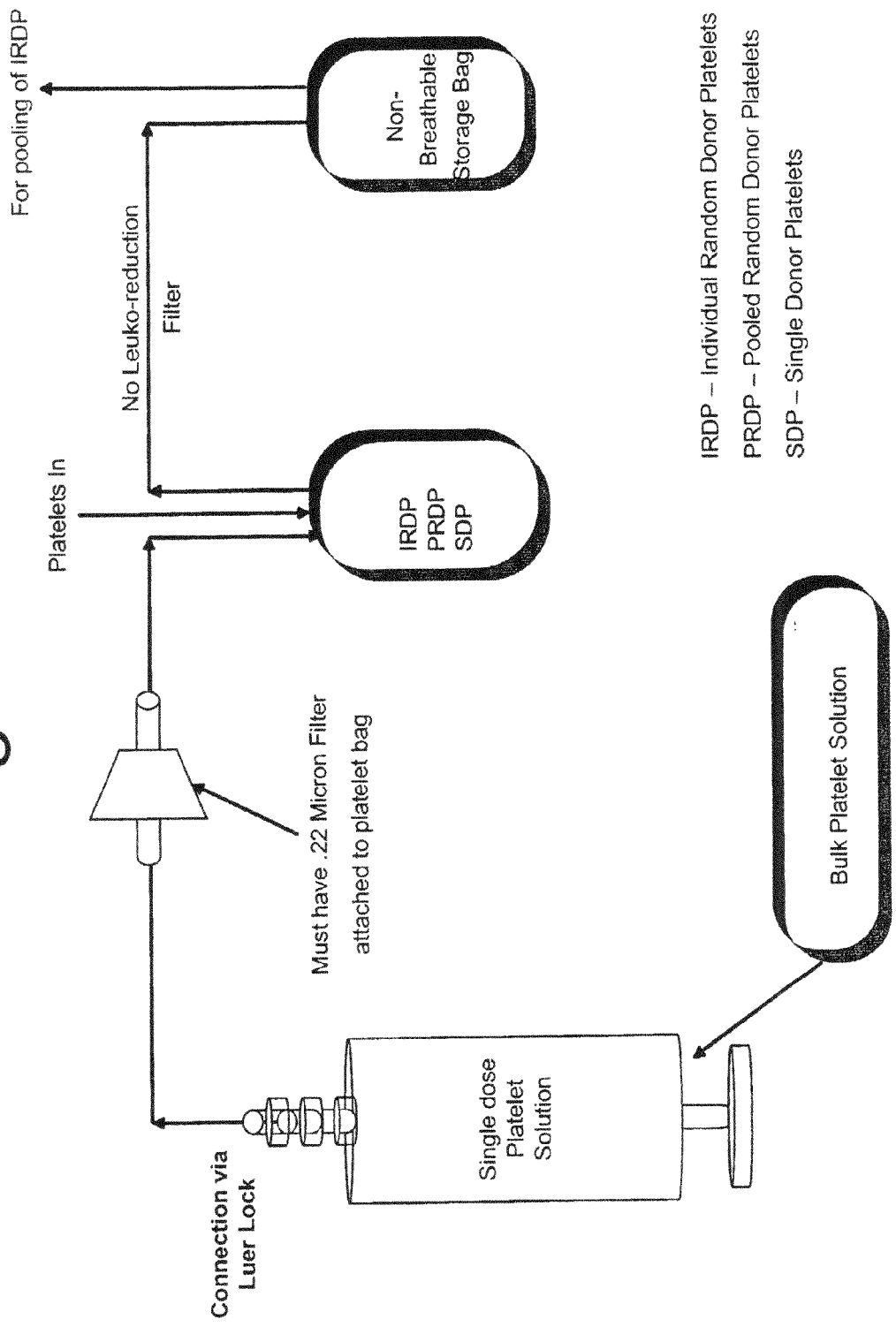
FIG. 54 illustrates a variation of FIG. 53, that does not include a leukocyte filter.
Figure 55:
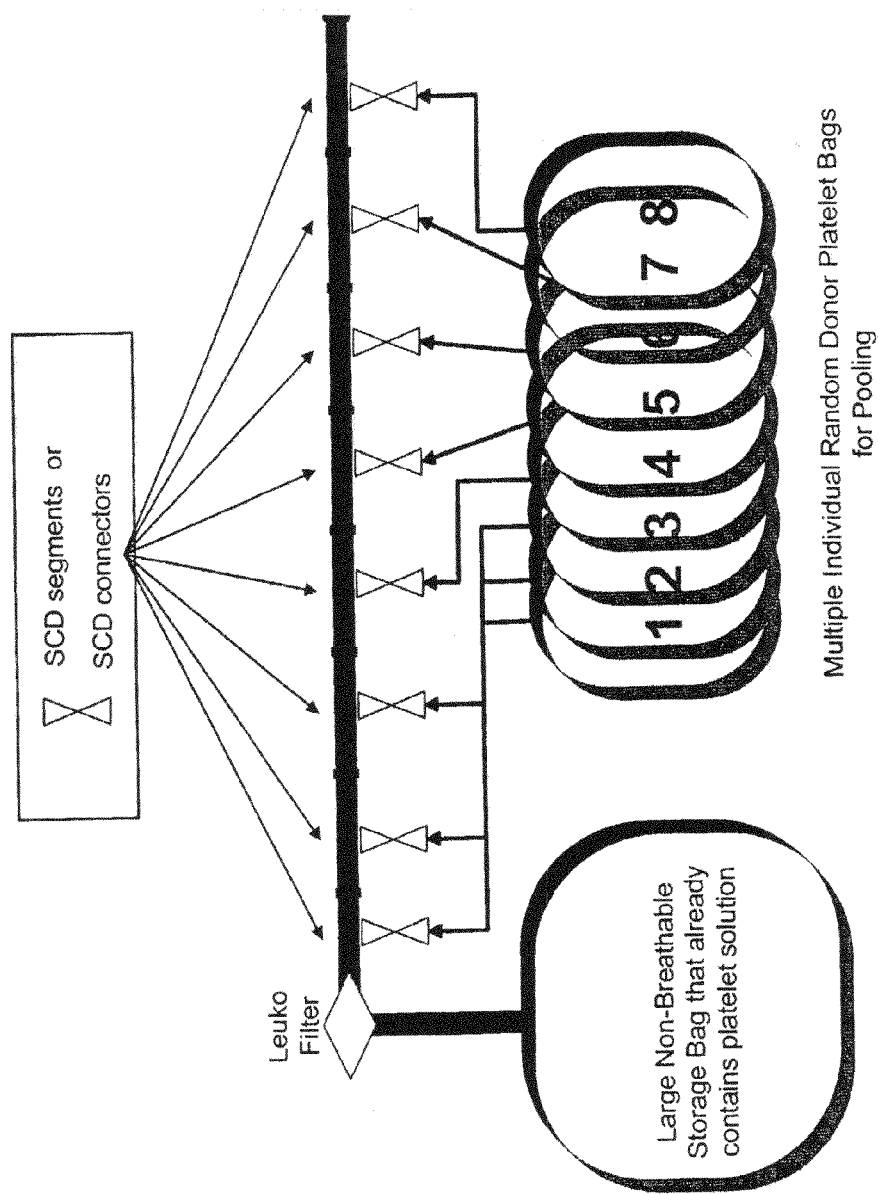
FIG. 55 illustrates another embodiment of the invention wherein a bioprocess for collecting, treating and storing platelets is described. The large non-breathable bag (final storage bag) containing the platelet solution includes an array comprising long piece of conduit and a plurality of ports to allow the sterile docking of multiple IRDP bags sequentially from the distal end of the tube (denoted #8) to the proximal end (denoted #1) thru a 0.22 micron filter to the bag containing the platelet solution. The platelet solution is mixed with the pooled platelets.
Figure 56:
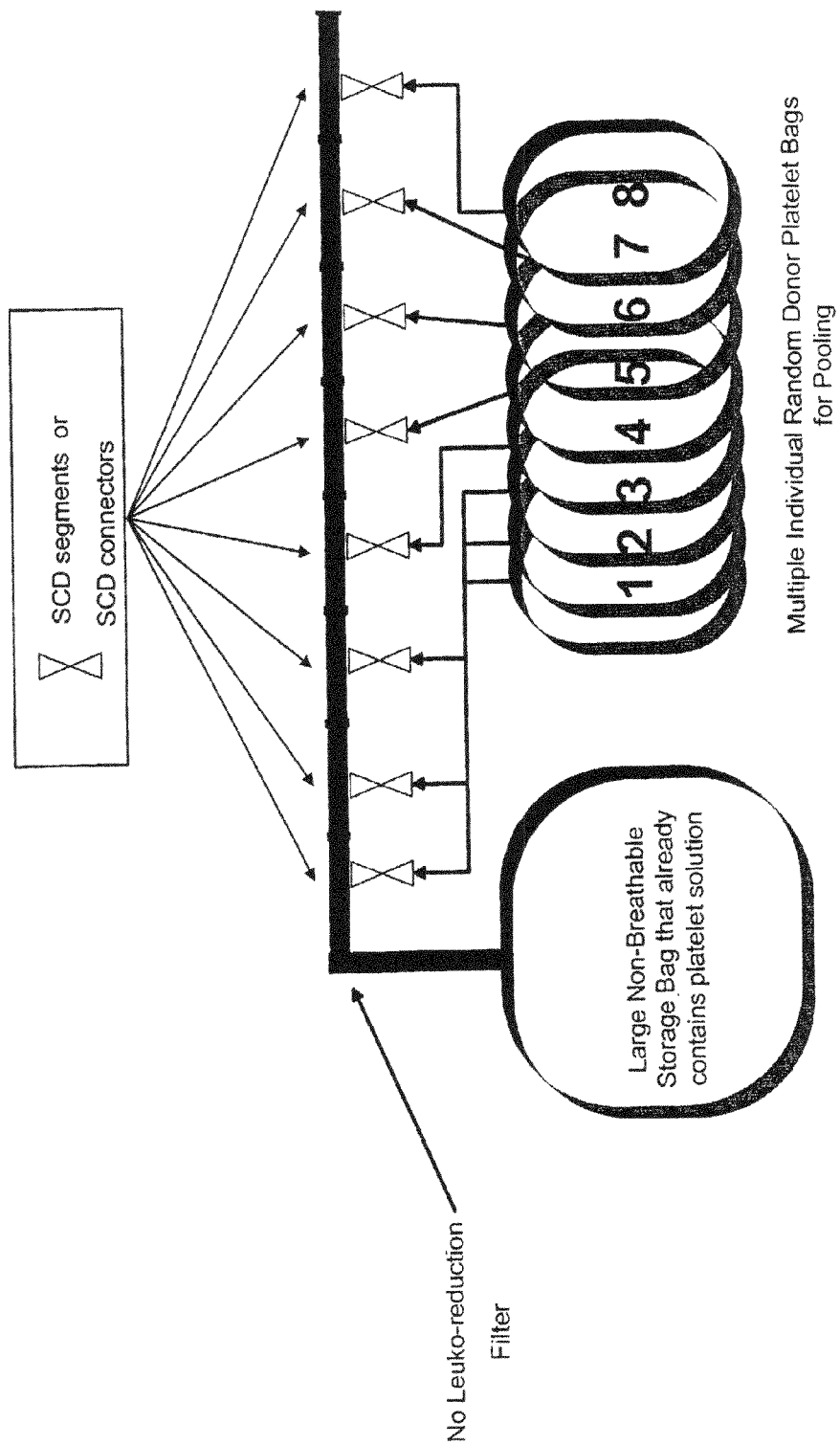
FIG. 56 illustrates a variation of FIG. 55, that does not include a leukocyte filter.
Figure 57:
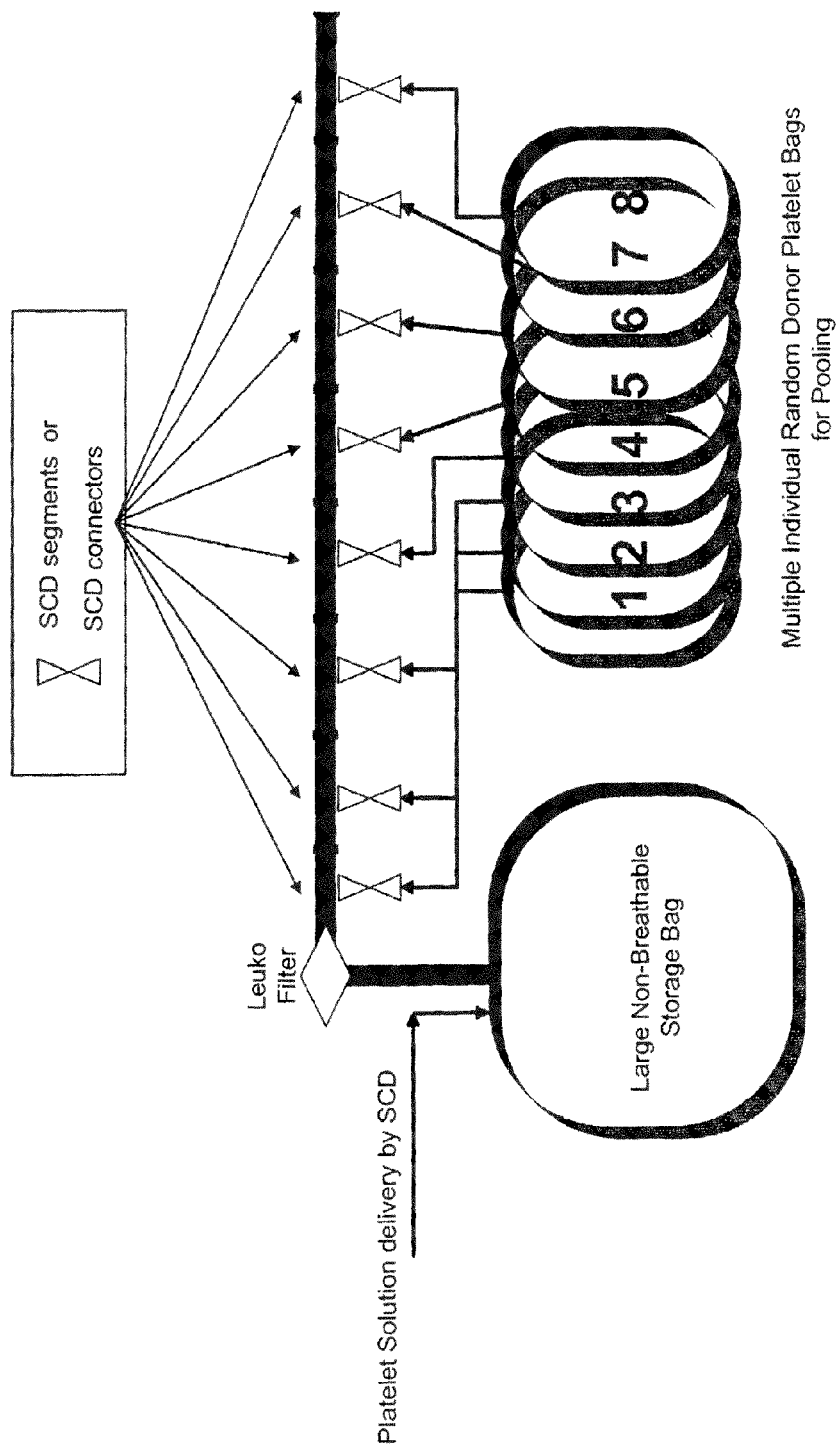
FIG. 57 illustrates another embodiment of the invention wherein a bioprocess for collecting, treating and storing platelets is described. Platelet solution delivery to the containment bag is facilitated by an SCD on the bag.
Figure 58:
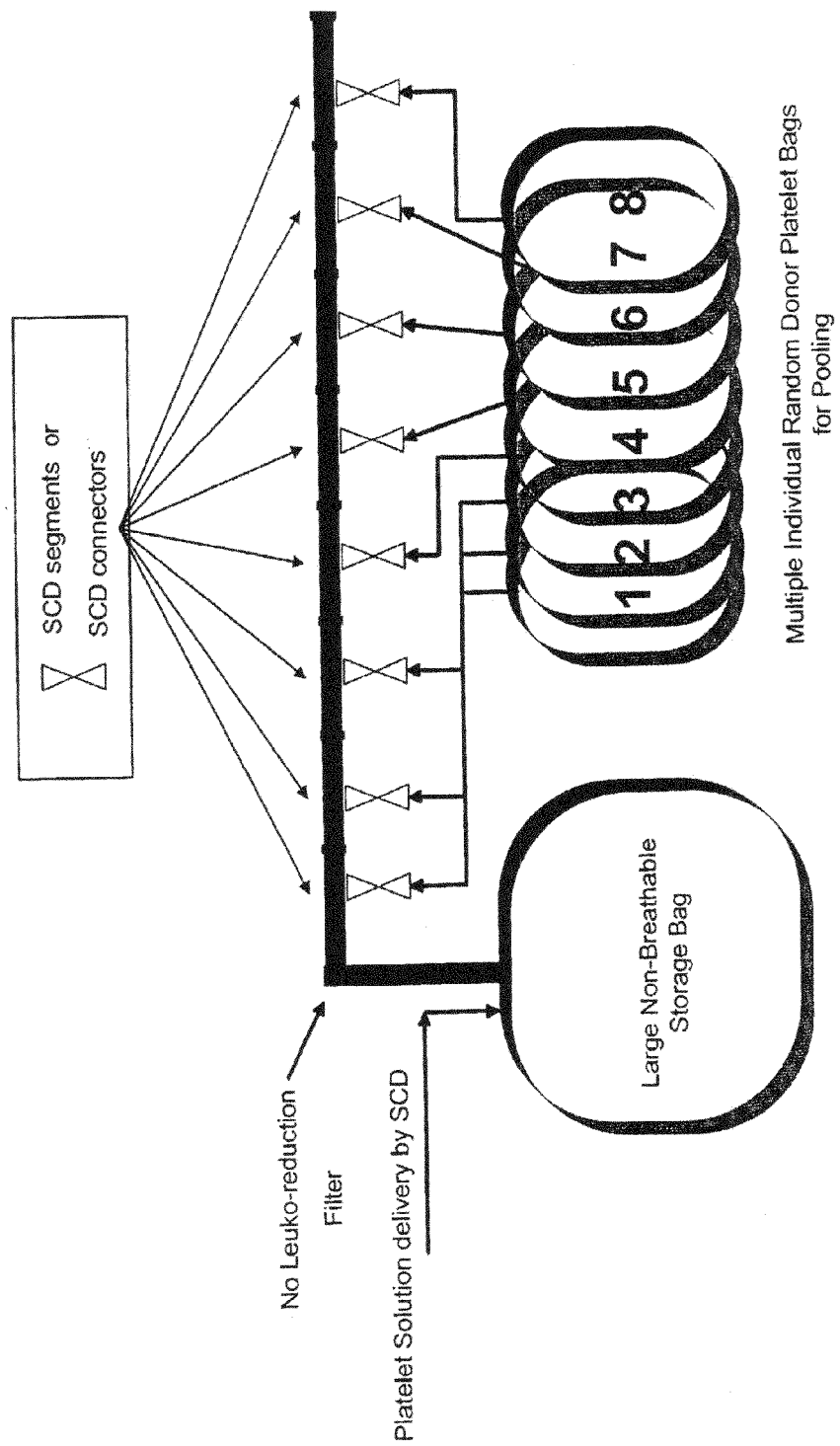
FIG. 58 illustrates a variation of FIG. 57, that does not include a leukocyte filter.
Figure 59:
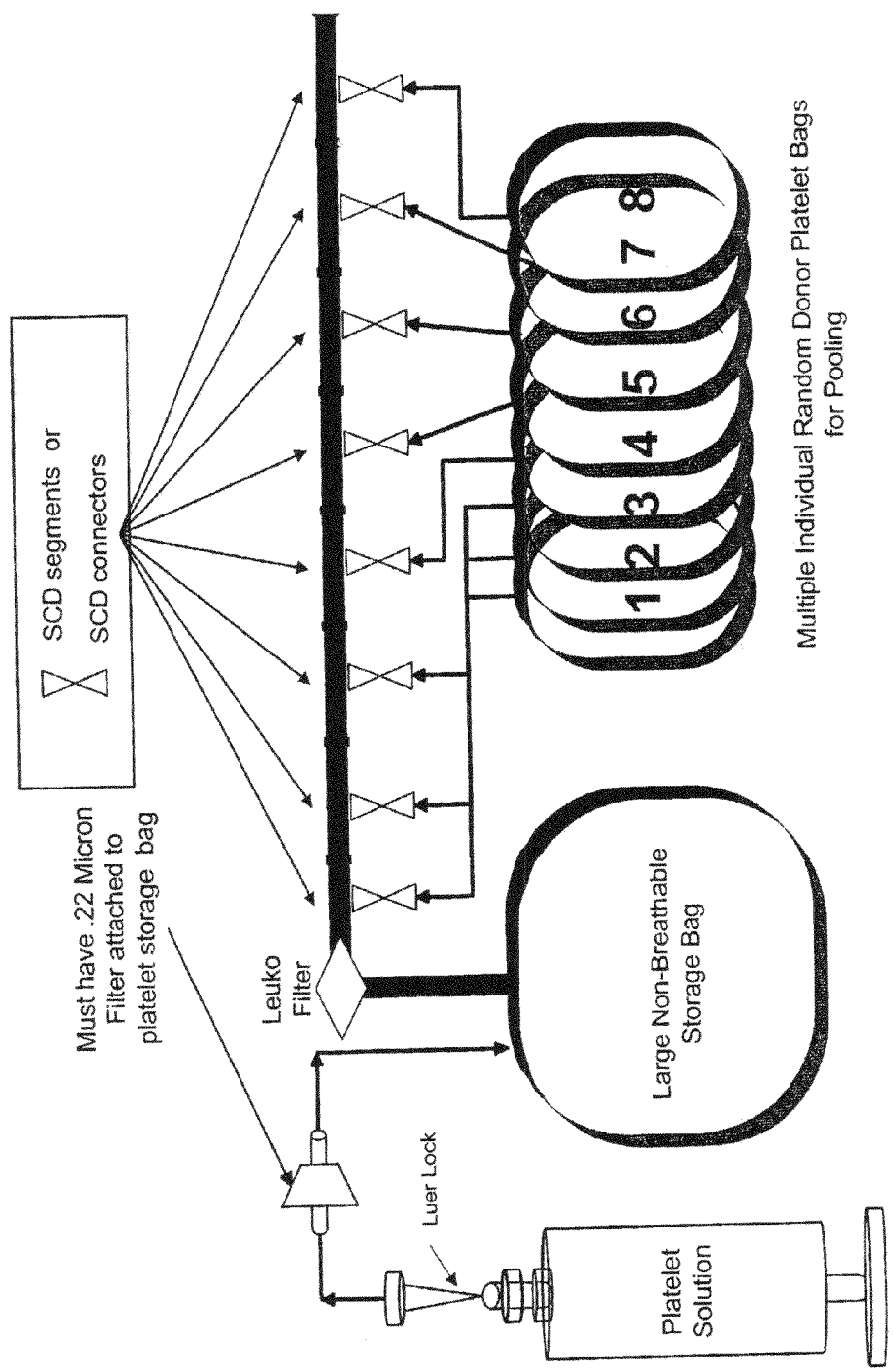
FIG. 59 illustrates a variation of FIG. 57. The large non-breathable bag (final storage bag) has the platelet solution, stored in a syringe, aseptically connected and added thru a 0.22 micron filter.
Figure 60:
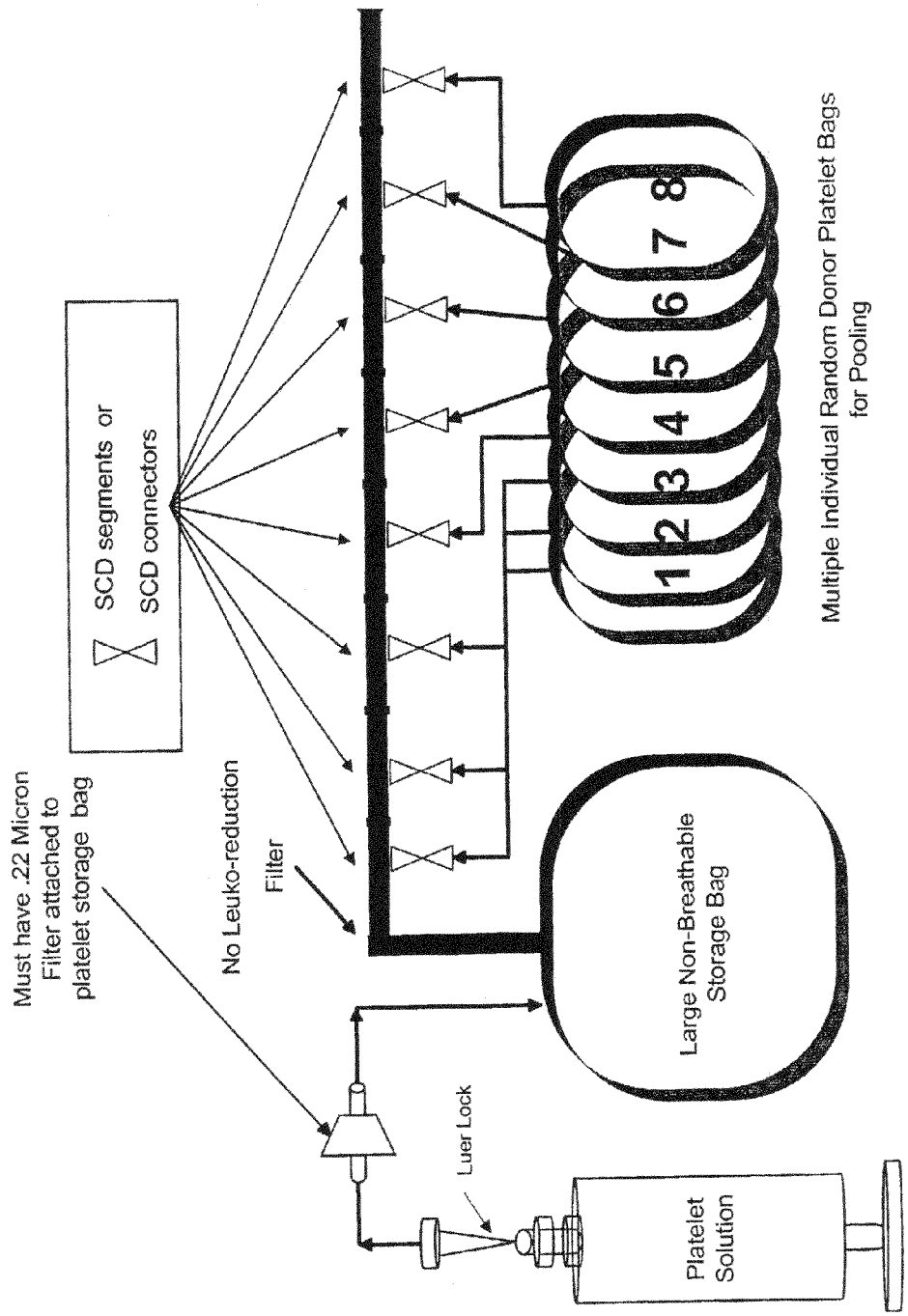
FIG. 60 illustrates a variation of FIG. 59, that does not include a leukocyte filter.
Figure 61:
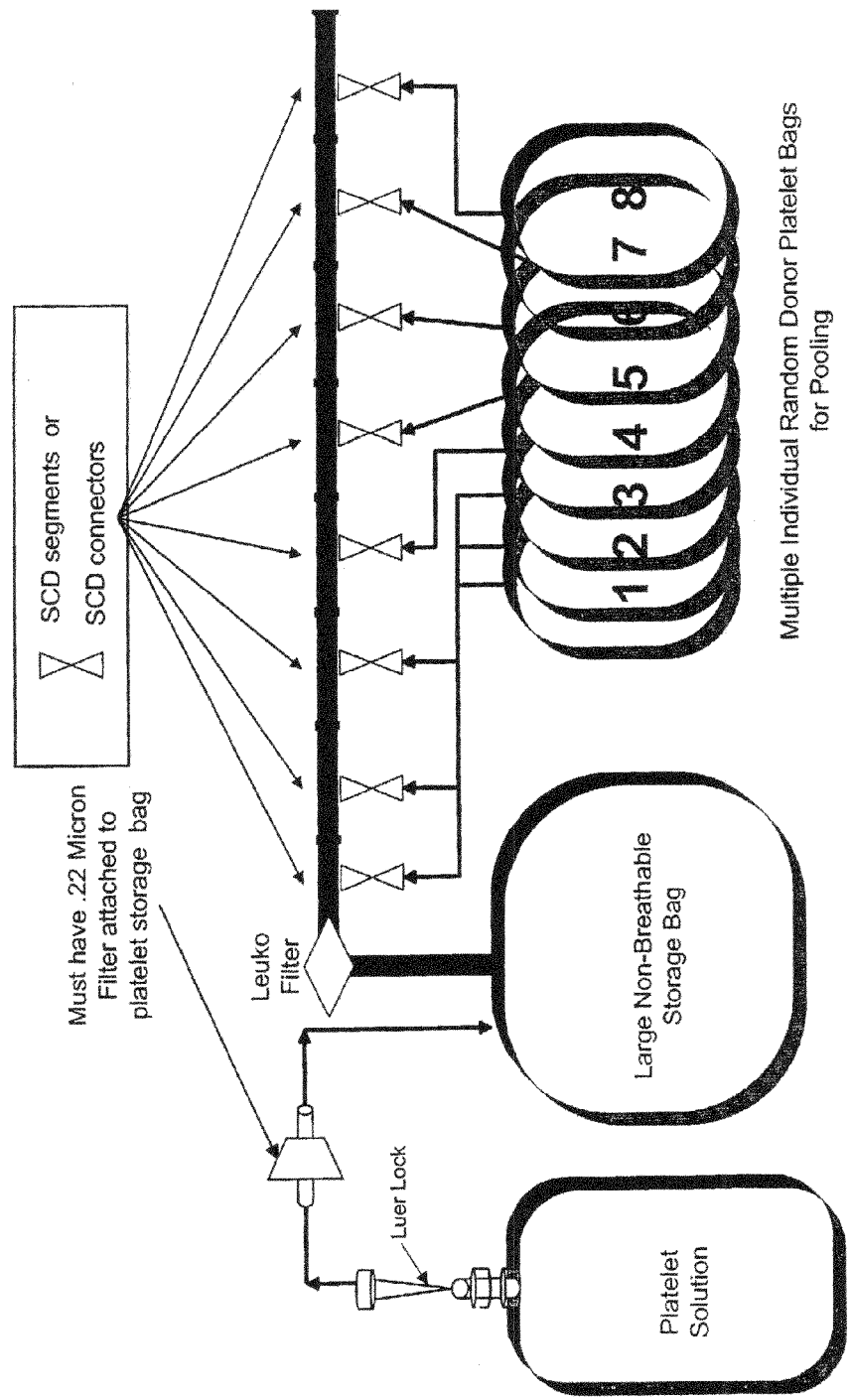
FIG. 61 illustrates a variation of the invention, wherein a container having platelet solution is adapted to the container having blood cells through a conduit attachable via a luer lock connection. The conduit has a bag spike to puncture a barrier in the container, thereby permitting withdrawal of the glycans modifying solution.
Figure 62:
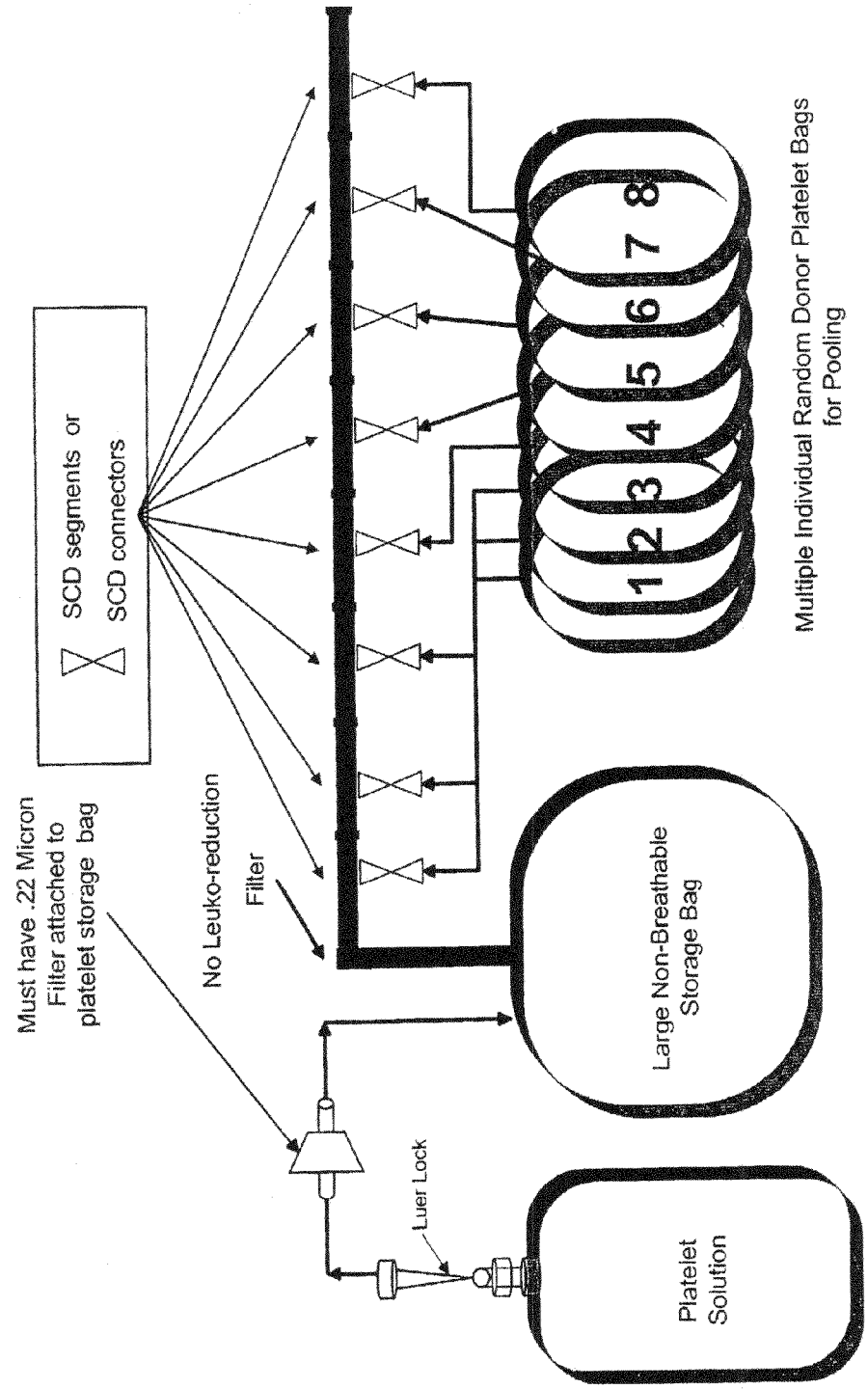
FIG. 62 illustrates a variation of FIG. 61, that does not include a leukocyte filter.
Figure 63:
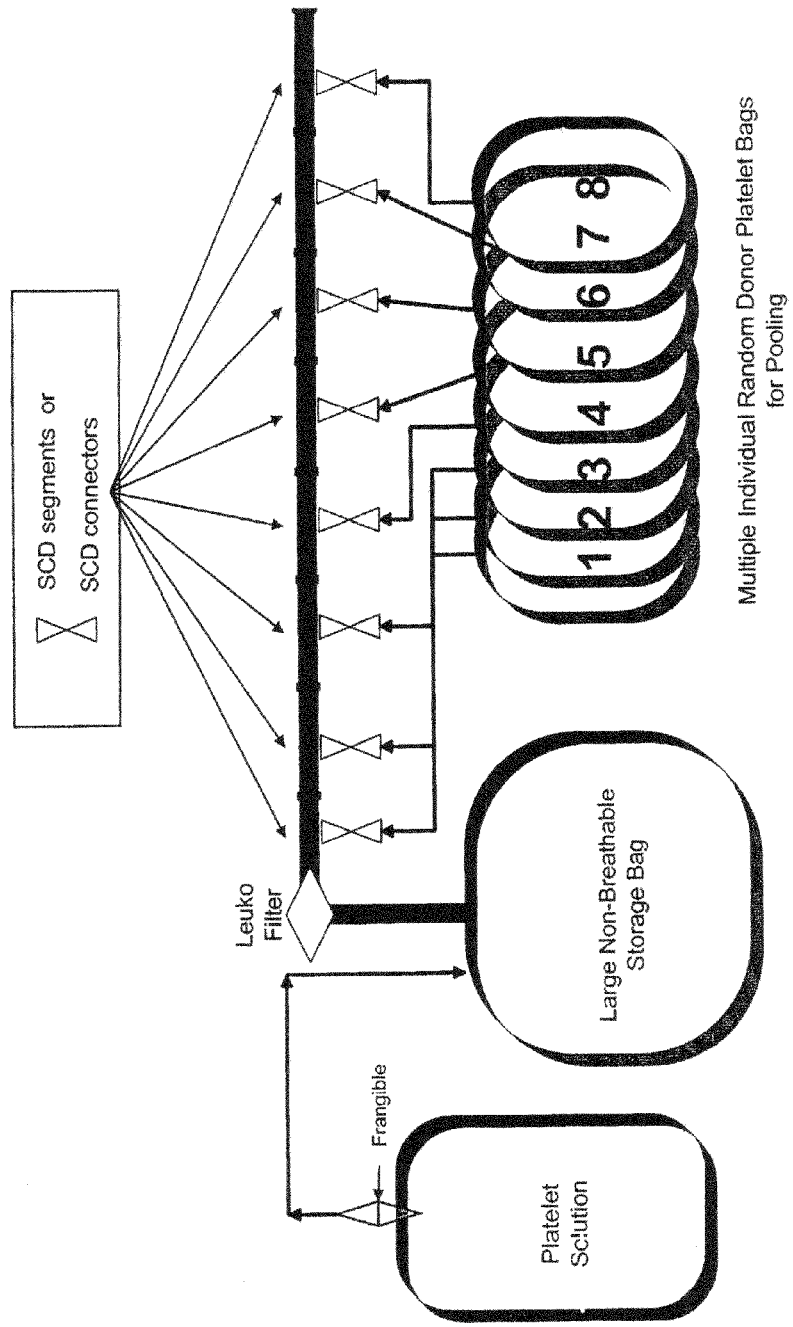
FIG. 63 illustrates another embodiment of the invention wherein a bioprocess for collecting, treating and storing platelets is described. The large non-breathable bag (final storage bag) has the platelet solution, stored in a bag, connected with a frangible plug that can be opened to deliver the platelet solution.
Figure 64:
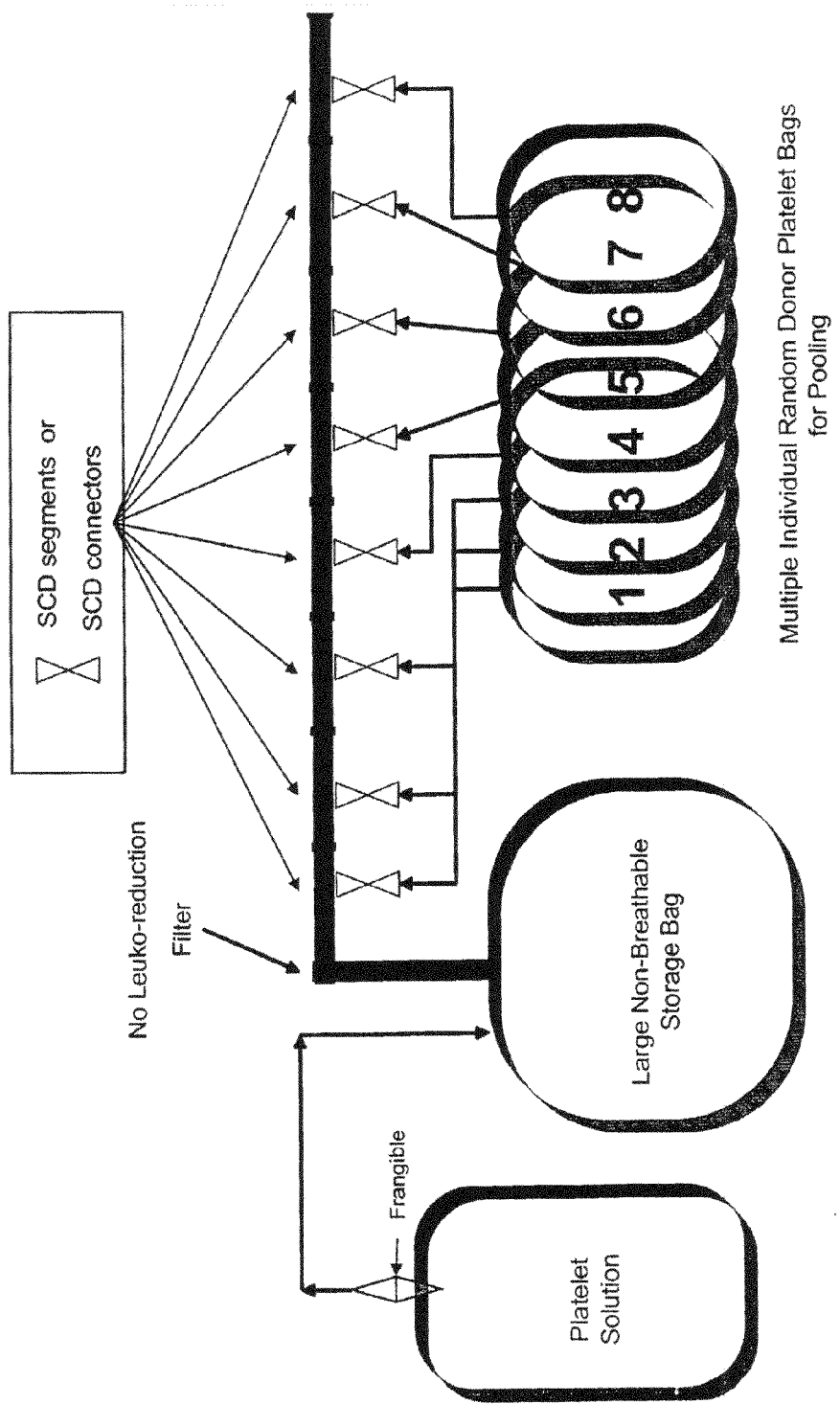
FIG. 64 illustrates a variation of FIG. 63, that does not include a leukocyte filter.
Figure 65:
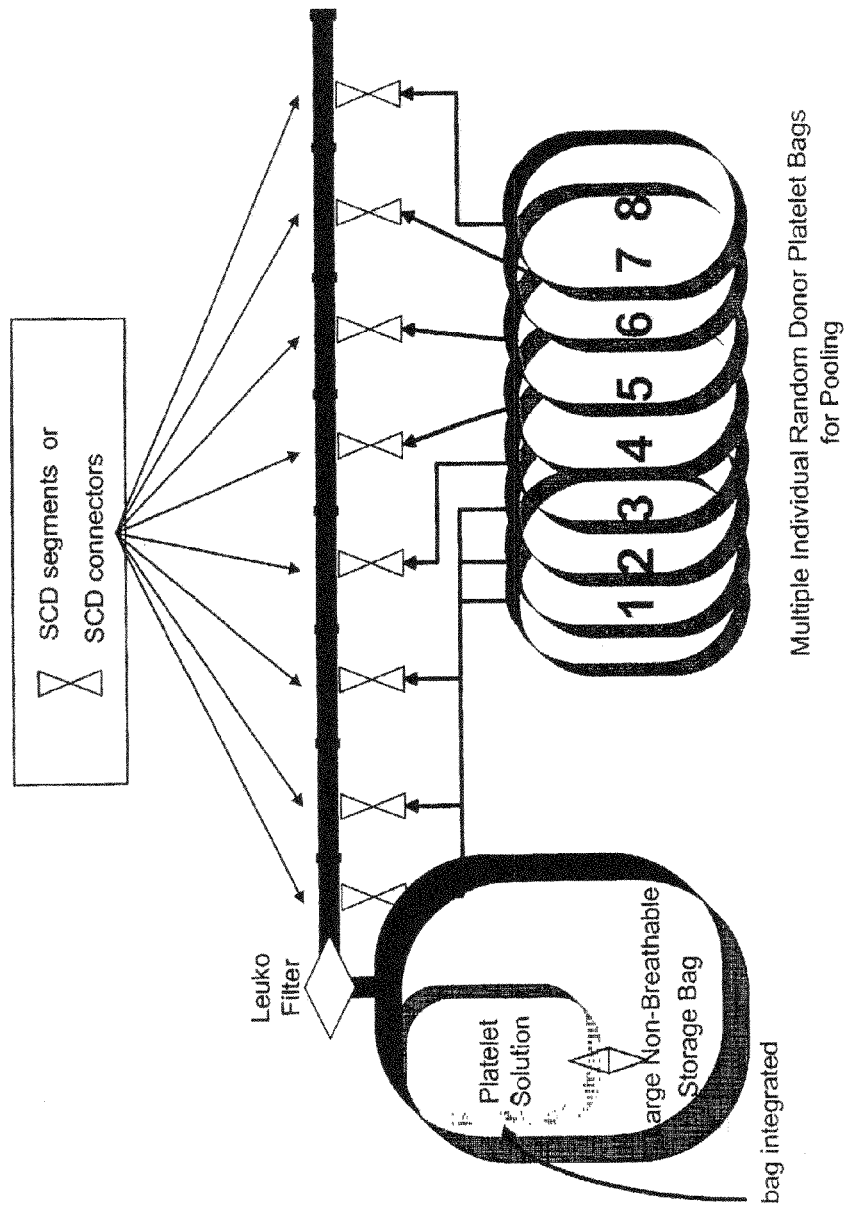
FIG. 65 illustrates another embodiment of the invention wherein a bioprocess for collecting, treating and storing platelets is described. The large non-breathable bag (final storage bag) includes an integrated bag of platelet solution having a frangible plug that can be opened to deliver the platelet solution directly into the platelet storage container.
Figure 66:
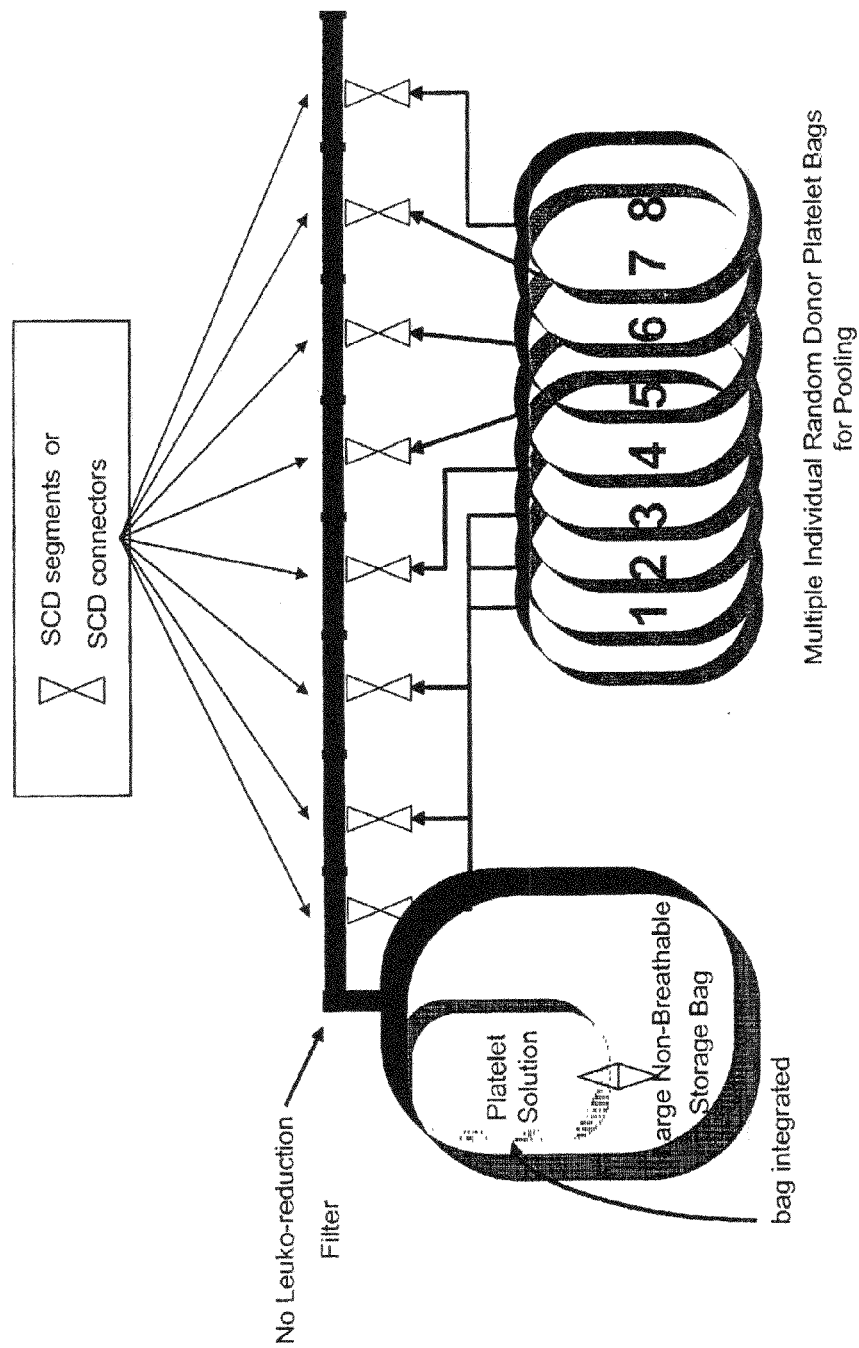
FIG. 66 illustrates a variation of the embodiment illustrated as FIG. 65. The bag having the platelet modifying solution is integrated within the storage bag. The platelet solution is released upon breaking of the frangible plug or separation membrane.

Four different platelet concentrates were treated with increasing concentrations of UDP galactose: 400 μM, 600 μM, and 800 μM. Future experiments will use between 10 μM and 5000 μM UDP galactose. RCA binding ratio measurements showed a dose dependent increase in galactosylation in the four samples tested. (FIG. 16). Our results provide evidence that galactosylation is possible in platelet concentrates.

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims. All references, patents and patent publications that are recited in this application are hereby incorporated by reference herein in their entirety.

Example 8

Evaluation of the In Vivo Survival of UDP-Galactose Treated Platelets Stored in the Cold The technology for galactosylating human platelets with the use of the activated carbohydrate substrate UDP-galactose may allow large-scale human platelet storage under refrigeration (4° C.). Untreated platelets stored at 4° C. are rapidly cleared from the circulation. In contrast, untreated platelets stored at room temperature survive for ~5-7 days following transfusion. The present study is intended to demonstrate that the galactosylated modified human platelets circulate in vivo when infused autologously into individuals.

The reason for the removal of chilled platelets from the circulation has recently been defined. Cooling of platelets causes clustering of the platelet GPIb/V/IX complex on the platelet surface. The αMβ2 integrin receptor (CR3, Mac-1) present on hepatic macrophages recognizes clustered GPIbα molecules, and platelets are ingested by the macrophages. The αMβ2 integrin receptor contains a carbohydrate binding domain (lectin domain) that is critical for the recognition of exposed β-N-acetylglucosamine (βGlcNAc) residues on the platelet surface by macrophages. Covering of exposed βGlcNAc residues by enzymatic galactosylation prevents recognition and phagocytosis of chilled platelets. This has been extensively demonstrated in a mouse model, where chilled and galactosylated murine platelets have survival superior to that of room temperature stored platelets. In vitro studies using human platelets indicate that galactosylated platelets stored at 4° C. are likely also to circulate when transfused into humans.

To determine and demonstrate that galactosylated modified human platelets survive and circulate in vivo when infused autologously into individuals. This will be determined by comparing the survival rates of radiolabeled refrigerated (2°-8° C.) platelets with or without galactosylation to radiolabeled non-galactosylated platelets stored at room temperature (22°±2° C.) and in the cold (Stored for 36 to 48 hrs).

The following describes a Phase I study in which in vivo recovery and half-life of autologously-infused galactosylated platelets in normal, healthy volunteer group subjects is determined.

Six (6) healthy donors will donate a unit of apheresis platelets. The collected apheresis product will be divided into two bags. One bag will have the platelets treated with UDP-galactose and stored under refrigeration for 36-48 hours. The other platelet bag will either be stored under refrigeration or as per current FDA guidelines at room temperature for 36-48 hours. The two bags of platelets will each be radiolabeled with a different radioactive isotope, [51]Chromium or [111]Indium and 5-10 mL of labeled platelets will be injected in the healthy volunteers. Blood samples will be drawn before and at 2 hours after the transfusion and then on days 1, 2, 3, 5, 7 and 10 after reinfusion, and the post-transfusion recovery and survival of the platelets will be determined.

The experimental material injected in the healthy volunteers will be 5-10 mL aliquots of platelets that have been taken from the study subjects, with or without modification by galactosylation and either stored at room temperature (22±2° C.) or stored in the cold (4±2° C.).

Upon confirmation of eligibility and enrollment in the study, healthy donors will be recruited to donate a unit of platelets on the Haemonetics MCS+ apheresis machine. This machine draws whole blood from a donor's arm, centrifuges the blood to separate the platelets from the plasma and the red cells, collects the platelets with a small amount of plasma and returns most of the plasma and the red cells back to the donor. The collected platelets and plasma will be divided into two bags. Each bag will be weighed and the platelet count determined on the day of collection, day 1 and day of infusion. After collection the platelets will be rested for 1 hour. After the resting period one platelet bag will be treated with a naturally occurring sugar substance, UDP-galactose. This bag will be incubated for 1 hour at 37° C. and stored under refrigeration. The other platelet bag will likewise be incubated for 1 hour at 37° C. and stored under refrigeration or as per current FDA guidelines at room temperature. On Day 1 following collection a sample from each bag will be sent to a microbiology lab for culture.

The platelet culture results will be recorded along with the results of a gram stain sample that will be sent to the lab on the day of reinfusion. If either report is positive the platelet units will not be reinfused. The two bags of platelets will each be radiolabeled with a different radioactive isotope, $^{51}$Chromium or $^{111}$Indium. Blood samples will be drawn before and at 2 hours after and then on days 1, 2, 3, 5, 7 and 10 after the reinfusion. The blood samples will be analyzed for radioactivity to determine the post-transfusion recovery and survival of the platelets. Since the two units of platelets have been tagged with different radioactive isotopes, we will be able to distinguish between the platelets that were subjected to the UDP Galactose and those that are untreated.

UDP-galactose (Uridine-5'-diphosphogalactose) is a natural sugar compound found in the human body. It is used in this study as a donor for the addition of galactose to the surface of the human platelets to be transfused. The UDP-galactose was manufactured by Roche Diagnostics GmbH and is over 97% pure. It contains trace quantities of by-products of the manufacturing process. It was formulated and filled into syringes by a licensed filling facility, and tested for sterility and pyrogenicity.

Blood samples taken from each study subject will be tested for platelet count and anti-platelet antibodies before and at two weeks and three months after the platelet infusion.

Between 5 and 10 mL of platelets radiolabeled with the two different radioactive isotope, $^{51}$Chromium or $^{111}$Indium, will be injected at day 0. Blood samples will be drawn before and at 2 hours and on days 1, 2, 3, 5, 7 and 10 after reinfusion.

During each reinfusion, the subject will be carefully monitored for adverse reactions, most usually fever, chills, dyspnea, urticaria or pain (infusion site, chest pain or other), or significant changes in vital signs. In addition, each subject will be queried during the follow up period visits up to three months after the infusion to obtain information on any occurrence of adverse events during that time. Non-modified and modified platelets will be characterized by a number of in vitro analyses including but not limited to: pH, pO2, pCO2, bicarbonate, hypotonic shock response, morphology, extent of shape change, ATP levels, glucose, O2 consumption, p-Selectin, and Annexin V binding.

REFERENCES

Incorporated Herein in their Entirety

1. Becker, Tucecelli et al. G. Transfusion 13, 61 (1973).
2. Hoffmeister, Felbinger et al. Cell 10, 87 (2003).
3. Valeri, Ragno et al. Transfusion 44(6):865-70 (2004).
4. Murphy S, Oski F A et al N Engl J. Med. 1969 16; 281(16): 857-62
5. Dumont, VandenBroeke et al. Transfus Med. Rev. 13(1): 31-42 (1999).
6. Michelson, Adelman et al. J Clin Invest. 81(6):1734-40 (1988).
7. Ribeiro, Swarm et al. Thromb Res. 66(6):619-27 (1992).
8. Jaremo, Rubach-Dahlberg et al. Thromb Res. 69(5):467-77 (1993).
9. Hoffmeister, Josefsson et al. Science September 12; 301 (5639):1531-4 (2003).
10. J Pediatr Gastroent Nutr 13:260-266 (1991).
11. J Pediatr Gastroent Nutr 19:100-108 (1994).
12. Mizoguchi, Ono et al., Eur J Pediatr 159: 851-853 (2000).
13. Lancet 346:1073-1074 (1995).
14. Acta Medica Scandinav Suppl 177:1-125 (1947).
15. Lazarowski, Shea et al. Mol Pharmacol 63: 1190-1197 (2003).
16. Josefsson et al J Biol. Chem. 2005 Mar. 1; [Epub ahead of print]
17. Puget Sound Blood Center SOP, "Radiolabeling Fresh Platelets with $^{111}$Indium Oxine or $^{51}$Chromium", Rev. Jan. 12, 2005
18. Puget Sound Blood Center SOP, "Radiolabeling Stored Apheresis Platelets with $^{51}$Chromium", Rev. Jan. 12, 2005
19. Puget Sound Blood Center SOP, "Radiolabeling Stored Apheresis Platelets with $^{111}$Indium Oxine", Rev. Jan. 12, 2005

What is claimed is:

1. A method for treating a platelet using an apparatus, wherein the apparatus comprises a first sterile container having one or more ports and containing a preparation of blood cells comprising platelets; and a second sterile container having one or more ports and containing two or more blood cell modifying agents; wherein the first sterile container is adapted to the second sterile container through a sterile conduit reversibly attached to a first container port and to a second container port, wherein the conduit further comprises a valve; wherein the steps of the method comprise:
   processing the platelets using the apparatus such that the platelets are exposed to the two or more blood cell modifying agents that include UDP-galactose and cytidine 5'-monophospho-N-acetylneuraminic acid;
wherein the platelets are rendered cold-storage competent after being contacted with the two or more blood cell modifying agents.

2. The method of claim 1, further comprising separating leukocytes from the blood cells prior to exposing the blood cells to the two or more blood cell modifying agents.

3. The method of claim 1, wherein the blood cells are contacted with the two or more blood cell modifying agents before infusion of the treated blood cells into a patient.

4. The method of claim 1, wherein the blood cells are contacted with the two or more blood cell modifying agents before cold storage of the blood cells.

5. The method of claim 1, wherein the blood cells are contacted with the two or more blood cell modifying agents at the time of blood collection from a blood donor.

6. The method of claim 1, further including separating the blood cells into subpopulations of platelets, plasma, red blood cells, and white blood cells.

7. The method of claim 1, wherein the blood cells are contacted with the two or more blood cell modifying agents after the blood cells have been separated by apheresis.

8. A method for treating a platelet using an apparatus, wherein the apparatus comprises a first sterile container having one or more ports and containing a preparation of blood cells comprising platelets; and a second sterile container having one or more ports and containing two or more blood cell modifying agents; wherein the first sterile container is adapted to the second sterile container through a sterile conduit reversibly attached to a first container port and to a second container port; wherein the steps of the method comprise:

contacting the platelets with the two or more blood cell modifying agents, wherein the two or more blood cell modifying agents comprise UDP-galactose and cytidine 5'-monophospho-N-acetylneuraminic acid, to thereby obtain treated platelets.

9. The method of claim 8, wherein an amount of each of the two or more blood cell modifying agents is between about 1 micromolar and about 10 millimolar.

10. The method of claim 8, wherein an amount of each of the two or more blood cell modifying agents is between about 1 micromolar and about 1200 micromolar.

11. The method of claim 8, further comprising storing the treated platelets for a period of time ranging between about 24 hours and about 20 days.

12. The method of claim 8, further comprising storing the treated platelets for a period of time ranging between about 24 hours and about 7 days.

13. The method of claim 8, further comprising storing the treated platelets for a period of time ranging between about 24 hours and about 5 days.

14. The method of claim 8, further comprising storing the treated platelets at a temperature ranging between about 0° C. and about 4° C.

15. The method of claim 8, further comprising storing the treated platelets at a temperature ranging between about 4° C. and about 15° C.

16. The method of claim 8, further comprising storing the treated platelets at a temperature ranging between about 15° C. and about 37° C.

17. The method of claim 8, wherein the platelets are contacted with the UDP-galactose and cytidine 5'-monophospho-N-acetylneuraminic acid simultaneously or sequentially.

* * * * *